United States Patent
Kimura

(10) Patent No.: US 9,023,993 B2
(45) Date of Patent: *May 5, 2015

(54) ANTI-CANCER AGENT COMPRISING ANTI-HB-EGF ANTIBODY AS ACTIVE INGREDIENT

(75) Inventor: Naoki Kimura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1083 days.

This patent is subject to a terminal disclaimer.

(21) Appl. No.: 12/311,950

(22) PCT Filed: Oct. 19, 2007

(86) PCT No.: PCT/JP2007/070466
§ 371 (c)(1),
(2), (4) Date: Aug. 19, 2009

(87) PCT Pub. No.: WO2008/047914
PCT Pub. Date: Apr. 24, 2008

(65) Prior Publication Data
US 2010/0273988 A1 Oct. 28, 2010

(30) Foreign Application Priority Data
Oct. 20, 2006 (JP) ................................ 2006-286824

(51) Int. Cl.
*C07K 16/00* (2006.01)
*C07K 16/22* (2006.01)
*C07K 16/30* (2006.01)
*A61K 39/00* (2006.01)

(52) U.S. Cl.
CPC ........... *C07K 16/22* (2013.01); *A61K 2039/505* (2013.01); *C07K 16/30* (2013.01); *C07K 2316/96* (2013.01); *C07K 2317/56* (2013.01); *C07K 2317/565* (2013.01); *C07K 2317/73* (2013.01); *C07K 2319/30* (2013.01)

(58) Field of Classification Search
CPC ...................................................... C07K 16/00
See application file for complete search history.

(56) References Cited

U.S. PATENT DOCUMENTS

| | | | |
|---|---|---|---|
| 6,342,219 | B1 | 1/2002 | Thorpe et al. |
| 2005/0272634 | A1 | 12/2005 | Bahlmann et al. |
| 2010/0061933 | A1 | 3/2010 | Kimura |
| 2010/0266502 | A1 | 10/2010 | Kimura |
| 2012/0177649 | A1 | 7/2012 | Mekada et al. |

FOREIGN PATENT DOCUMENTS

| | | |
|---|---|---|
| EP | 2 039 704 | 3/2009 |
| EP | 2 078 731 | 7/2009 |
| EP | 2 093 237 | 8/2009 |
| WO | WO 2005066348 A2 | 7/2005 |
| WO | WO 2007/142277 | 12/2007 |
| WO | WO 2008/047914 | 4/2008 |
| WO | WO 2008/047914 A1 | 4/2008 |
| WO | WO 2008/047925 | 4/2008 |
| WO | WO 2008148884 A1 | 12/2008 |
| WO | WO 2009/040134 | 4/2009 |
| WO | WO 2009/072628 | 6/2009 |

OTHER PUBLICATIONS

Blotnick et al. (PNAS, vol. 91 (1994), pp. 2890-2894; A13 cited on IDS filed Jul. 13, 2009).*
Yagi et al. (British Journal of Cancer, vol. 92, pp. 1737-1745, Apr. 2005).*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Falkenberg et al. (Falkenberg (J. Clin. Chem. Clin. Biochem. 1984, 22:867-882).*
S. Blotnick et al., "T lymphocytes synthesize and export heparin-binding epidermal growth-factor like growth factor and basic fibroblast growth factor, mitogens for vascular cells and fibroblasts: Differential production and release by CD4+ and CD8+ T Cells," *Proc Natl. Acad. Sci* USA, 91,1994, pp. 2890-2894.
K. Hashimoto et al. "Heparin-binding Epidermal Growth Factor-like Growth Factor is an Autocrine Growth Factor for Human Keratinocytes," *The Journal of Biological Chemistry*, 269(31), 1994, pp. 20060-20066.
Y. D. Wang et al. "Cooperation between heparin-binding EGF-like growth factor and interleukin-6 in promoting the growth of human myeloma cells," *Oncogene*, 21, 2002, pp. 2584-2592.
Y. Myoken et al. "Monoclonal Antibodies Against Heparin-Binding Growth Factor-1: Neutralization of Biological Activity and Recognition of Specific Amino Acid Sequences," *Biochemical and Biophysical Research Communications*, 1970, 1993, pp. 1450-1457.
Iwamoto, Ryo et al., "Heparin-binding EGF-like growth factor and ErbB signaling is essential for heart function," *Proc. Natl. Acad. Sci. USA*,; vol. 100, No. 6, (2003), pp. 3221-3226.
Abraham, Judith A., "Heparin-Binding EGF-Like Growth Factor: Characterization of Rat and Mouse cDNA Clones, Protein Domain Conservation Across Species, and Transcript Expression in Tissues," *Biochemical and Biophysical Research Communications*, vol. 190, No. 1, (1993), pp. 125-133.

(Continued)

*Primary Examiner* — Laura B Goddard
*Assistant Examiner* — Meera Natarajan
(74) *Attorney, Agent, or Firm* — Sterne, Kessler, Goldstein & Fox P.L.L.C.

(57) ABSTRACT

A monoclonal antibody having a neutralizing activity on HB-EGF is disclosed. The monoclonal antibody of the present invention is preferably an antibody that does not bind to the HB-EGF protein on the cell surface of HB-EGF-expressing cells. Also provided are an anti-cancer agent and a cell proliferation inhibitor, which comprise the monoclonal antibody of the present invention as an active ingredient, and a method of treating cancer, the method comprising administering the monoclonal antibody of the present invention. Cancers that can be treated by the anti-cancer agent of the present invention include pancreatic cancer, liver cancer, esophageal cancer, melanoma, colorectal cancer, gastric cancer, ovarian cancer, bladder cancer, and brain tumors.

13 Claims, 11 Drawing Sheets

(56) References Cited

OTHER PUBLICATIONS

Davids-Fleischer, Karen M et al., Structure and Function of Heparin-Binding EGF-like Growth Factor (HB-EGF), *Frontiers in Bioscience*, 3, (1998), pp. 288-299.
Raab, Gerhard et al., "Heparin-Binding EGF-like Growth Factor," *Biochemica et Biophysica Acta*, 1333, (1997), pp. F179-F199.
Yamazaki, Satoru et al., "Mice with Defects in HB-EGF Ectodomain Shedding Show Severe Developmental Abnormalities," *J Cell Biol*, vol. 163, No. 3, (2003), pp. 469-475.
Ongusaha, Pat P. et al., "HB-EGF is a Potent Inducer of Tumor Growth and Angiogenesis," *Cancer Research*, 64, (2004), pp. 5283-5290.
Iwamoto, Ryo et al., "Heparin-binding EGF-like Growth Factor, Which Acts as the Diphtheria Toxin Receptor, Forms a Complex with Membrane Protein DRAP27/CD9, which Up-Regulates Functional Receptors and Diphtheria Toxin Sensitivity," *EMBO J.*, vol. 13, No. 10, (1994), pp. 2322-2330.
Naglich, Joseph G. et al., "Expression Cloning of a Diphtheria Toxin Receptor: Identity with a Heparin-Binding EGF-like Growth Factor Precursor," *Cell*, vol. 69, (1992), pp. 1051-1061.
Iwamoto, Ryo et al., "Contact-Dependent Growth Inhibition and Apoptosis of Epidermal Growth Factor (EGF) Receptor-Expressing Cells by the Membrane-Anchored Form of Heparin-Binding EGF-like Growth Factor," *J. Biol. Chem.*, vol. 274, No. 36, (1999), pp. 25906-25912.
Miyamoto, Shingo et al., "Heparin-Binding Epidermal Growth Factor-like Growth Factor as a Novel Targeting Molecule for Cancer Therapy," *Cancer Sci.*, vol. 97, No. 5, (2006), pp. 341-347.
Blotnick, Sully et al., "T Lymphocytes Synthesize and Export Heparin-Binding Epidermal Growth Factor-like Growth Factor and Basic Fibroblast Growth Factor, Mitogens for Vascular Cells and Fibroblasts: Differential Production and Release by CD4+ and CD8+ T Cells," *Proc. Natl. Acad. Sci. USA*, vol. 91, (1994) 2890-2894.
Hashimoto, Koji et al., "Heparin-Binding Epidermal Growth Factor-like Growth Factor is an Autocrine Growth Factor for Human Keratinocytes," *J. Biol. Chem.*, vol. 269, No. 31, (1994), pp. 20060-20066.
Mishima, Kazuhiko et al., "Heparin-Binding Epidermal Growth Factor-like Growth Factor Stimulates Mitogenic Signaling and is Highly Expressed in Human Malignant Gliomas," *Acta Neuropathol.*, 96, (1998), pp. 322-328.
Wang, Yue Dan, "Cooperation Between Heparin-Binding EGF-like Growth Factor and Interleukin-6 in Promoting the Growth of Human Myeloma Cells," *Oncogene*, 21, (2002), pp. 2584-2592.
Miyamoto, Shingo, "Heparin-Binding EGF-like Growth Factor is a Promising Target for Ovarian Cancer Therapy," *Cancer Res.*, 64, (2004) pp. 5720-5727.
Buzzi, Silvio et al., "CRM197 (nontoxic diphtheria toxin): Effects on Advanced Cancer Patients," *Cancer Immunol Immunother*, 53, (2004), pp. 1041-1048.
Y. Myoken et al. "Monoclonal Antibodies Against Heparin-Binding Growth Factor-1: Neutralization of Biological Activity and Recognition of Specific Amino Acid Sequences," *Biochemical and Biophysical Research Communications*, 197(3), 1993, pp. 1450-1457.
International Preliminary Report on Patentability and Written Opinion of the International Searching Authority dated Apr. 30, 2009 issued in corresponding International Patent Application No. PCT/JP2007/070466.
Japanese Office Action, dated Nov. 6, 2012, issued in connection with corresponding Japanese Application No. 2008-539894.
Tee Fern Khong, et al. Kidney International, 2000, vol. 58, pp. 1098-1107.
Pieter J Gaillard, et al. International Congress Series, Apr. 2005 vol. 1277, pp. 185-198.
Japanese Office Action, dated Nov. 6, 2012, issued in connection with corresponding Japanese Application No. 2008-539888.
"Funakoshi General Catalog of Antibody 2004 Part I Antibody", Funakoshi Co., 2004, p. 405, xiii.
Office Action issued on Nov. 21, 2012, in connection with corresponding European Patent Application No. 07830200.7.

McKay Brown, et al.: "Tolerance to single; but not multiple, amino acid replacements in antibody V-H CDR2: A means of minimizing B cell wastage from somatic hypermutation?", The Journal of Immunology, the American Association of Immunologists, US, vol. 156, No. 9, Jan. 1, 1996, pp. 3285-3291.
Office Action dated Feb. 6, 2013, from the Chinese Patent Office concerning the corresponding Chinese Application No. 200780045144.7.
Introduction of Immunology,1999, pp. 49, table 3-3 and pp. 224, section 2.
U.S. Appl. No. 13/391,171, filed May 3, 2012, Kimura.
International Search Report, dated Jun. 28, 2012, issued in connection with corresponding European Application No. 07830221.3.
International Search Report, dated May 30, 2012, issued in connection with corresponding European Application No. 07830200.7.
International Search Report, dated Sep. 28, 2010, issued in connection with International Patent Application No. PCT/JP2010/005074, which corresponds to commonly owned U.S. Appl. No. 12/311,960.
White et al, (2001, Ann. Rev. Med., 2001 , 52:125-145).
Toki et al. (J. of Cellular Physiology, vol. 202:839-848, 2005).
Office Action, dated Aug. 2, 2011, issued in connection with Russian Patent Applic.ation No. 2008152746/15(069532), which corresponds to commonly owned U.S. Appl. No. 12/311,960.
Huang, P. P., et al., "Autologous Transplantation of Peripheral Blood Stem Cells as an Effective Therapeutic Approach for Severe Arteriosclerosis Obliterans of Lower Extremities", Thrombosis and Haemostasis, Dec. 2003, vol. 91, No. 3, pp. 606-609.
Office Action from the Chinese Patent Office dated Sep. 7, 2011, issued in connection with Chinese Application No. 200780045144.7, which corresponds to commonly owned U.S. Appl. No. 12/311,960.
Goishi, K., et al., "Phorbol Ester induces the Rapid Processing of Cell Surface Heparin-binding EGF-like Growth Factor: Conversion from Juxtacrine to Paracrine Growth Factor Activity", Molecular Biology of the Cell, vol. 6, pp. 967-980; Aug. 31, 1995.
Von Mehren, M., et al., "Monoclonal Antibody Therapy for Cancer", Annu. Rev. Med., vol. 54, pp. 343-369; Feb. 28, 2003.
Office Action from the Australian Patent Office dated Oct. 28, 2011, issued in connection with Australian Application No. 2007311957, which corresponds to commonly owned U.S. Appl. No. 12/311,960.
Nielsen, U. B., et al., "Internalizing Antibodies and Targeted Cancer Therapy: Direct Selection from Phage Display Libraries", *Pharmaceutical Science & Technology Today*, 2000, vol. 3, No. 8, pp. 282-291; Aug. 2000.
International Preiimiriary Report on Patentability and Written Opinion of the International Searching Authority issued in corresponding international Patent Application No. PCT/JP2007/070487 dated Apr. 19, 2009.
Miyamoto, S., et al., "Potential for Molecularly Targeted Therapy Against Epidermal Growth Factor Receptor Ligands", Anticancer Research, Mar. 2009, vol. 29, No. 3, pp. 823-830.
Poul, Marie-Aiix et al., "Selection of Tumor-Specific Internalizing Human Antibodies from Phage Libraries," Journal of Molecular Biology, vol. 301 (2000), pp. 1149-1161.
International Search Report issued in connection with corresponding International Application No. PCT/JP2009/003915.
E. Tagliabue et al. "Selection of Monoclonal Antibodies which Induce Internalization and Phosphorylation of p185$^{HEH2}$ and Growth Inhibition of Cells with HER2/*NEU* Gene Amplification," *Int. J. Cancer*, 47(6), 1991, pp. 933-937.
C.J. Wikstrand et al. "Cell Surface Localization and Density of Tumor associated Variant of the Epidermal Growth Factor Receptor, EGFRvIII," *Cancer Research*, 57(18), 1997, pp. 4130-4140.
Asakura, Masanori, et al. "Cardiac hypertrophy is inhibited by antagonism of ADAM12 proceeding of HB-EGF: Metalloproteinase inhibitors as a new therapy," Nature Medicine, vol. 8, No. 1, Jan. 2002, pp. 35-40.
Chinese Office Action, dated Aug. 22, 2012, issued in connection with corresponding Chinese Application No. 200780045023.2.
Hamaoka, M., et al. "Anti-human HB-EGF monoclonal antibodies inhibiting ectodomain shedding of HB-EGF and diphtheria toxin binding." J. Biochem. (2010) vol. 148 (1) pp. 55-69.

(56) References Cited

OTHER PUBLICATIONS

Murata, T., et al. "HB-EGF and PDGF Mediate Reciprocal Interactions of Carcinoma Cells with Cancer-Associated Fibroblasts to Support Progression of Uterine Cervical Cancers." Cancer Res. (2011) vol. 71, pp. 6633-6642.

Murata, T., et al. "HB-EGF and PDGF Mediate Reciprocal Interactions of Carcinoma Cells with Cancer-Associated Fibroblasts to Support Progression of Uterine Cervical Cancers." Cancer Res. (2011) vol. 71, pp. 6633-6642. Supplementary Materials and Methods.

Kusano, et al. "Immunocytochemical study on internalization of anti-carbohydrate monoclonal antibodies." Anticancer Research (1993), vol. 13, pp. 2207-2212.

Extended European Search Report, dated May 6, 2013, from the European Patent Office concerning the corresponding European Application No. 10809728,8.

Collet TA, et al. "A binary plasmid system for shuffling combinatorial antibody libraries." Proc. Natl. Acad. Sci. USA vol. 89: pp. 10026-10030 (1992).

Japanese Written Interrogation directed to related Japanese Patent Application No. 2008-539888, Appeal No. 2013-12560, mailed May 27, 2014; 4 pages.

Yu et al., "CD44 anchors the assembly of matrilysin/MMP-7 with heparin-binding epidermal growth factor precursor and ErbB4 and regulates female reproductive organ remodeling," *Genes & Development*; 16(3): 307-323; (Feb. 2002).

\* cited by examiner

Fig. 4a

(1) HEAVY CHAIN VARIABLE REGIONS

VH Segments

```
       FR1                                          CDR1       FR2                CDR2
       1234567890123456789012345678901234567890     12345AB    678901234567890    012A345678901234
                ----1----           ----2----      ---3--     -----4-----       ------5------  ------6------
MA20   QVQLQQPGAELVKPGASVKLSCKASGYTFT              SYHWN      WVKQRPGQGLEWIG     EINPSNGRTWYNEKFKS
MB20   QAQLKESGPGGLVAPSQSLSICTVSGFSLT              GYGIN      WVRQPPCKGLEWLG     MIW-GDGSADYNSALKS
MC15   EVQLQQSGPELVKPGASVKISCKASGYSFT              GYKMN      WVKQSPEKRLEWIG     EINPRTGITYYNQKFKA
```

```
       FR3                                                    CDR3
       67890123456789012abc345678901234                       5678904ABCDEFGHIJK12     3567890ABCDEFGHLJK12    35678901234
       ----7----  ----8----  ----9----                        ----10----               -----11------
MA20   KATLTVDKSSSTAYMQLSSLTSEDSAVYYCVW                       SLFDY                                            WGQGTLVTVSS
MB20   RLSIRKDNSKSQVFLKMNSLQTDDTARYYCAR                       GDYYGYRFSY                                       WGQGTLVTVSA
MC15   KATLTVDKSSSTAFMQLRSLTSEDSAVYYCAR                       VGSSHFFTI                                        WGQGTLVTVSA
```

JH Segments

(2) LIGHT CHAIN VARIABLE REGIONS

VK Segments

```
       FR1                                          CDR1                FR2                CDR2
       123456789012345678901234567890123            4567890LABCDE234    56789012345678     0123456
       ----1----  ----2----  ----3----              ------3------       -----4-----        ---5---
MA20   EIVLTQSPTTMAASPGEKITITC                      SASSSISSWYLH        WYQQKPGFSPKLLIY    RTSNLAS
MB20   NIMLTQSPSSLAVSAGEKVTMSC                      KSSQSVLYSSNQKHFLA   WYQQRPGQSPKLLIY    WASTRES
MC15   DIQMTQSPSSLSASLGERVSLTC                      RASQDIMGYLN         LFQQKPGETIKRLLIY   ETSMLDS
```

```
       FR3                                                    CDR3
       7890123456789012345678                                 90123414ABCDEF67    8901234567
       ----6----  ----7----  ----8----                        -----9-----         ----10----
MA20   GVPARFSGSGSGTSYSLTIGNEAEDVATYYC                        QQGSSIPFT           FGSGTRLEIK
MB20   GVPDRFAGSGSGTDFTLTISSVQTEDLAVYYC                       MQYLSSYY            FGGGTKLEIK
MC15   GVPKRFSGSRSGSDYSLIIGSLESEDFADYYC                       LQYASSLT            FGAGTKLELK
```

JK Segments
FR4

Fig. 4b

| ANTIBODIES | CHAINS | VARIABLE REGIONS | NUCLEOTIDE SEQUENCES (SEQ ID NOs:) | AMINO ACID SEQUENCES (SEQ ID NOs:) |
|---|---|---|---|---|
| HA20 | H CHAIN | FULL LENGTH (aa 1-19 IS SIGNAL) | 37 | 38 |
| | | CDR1 | 1 | 2 |
| | | CDR2 | 3 | 4 |
| | | CDR3 | 5 | 6 |
| HA20 | L CHAIN | FULL LENGTH (aa 1-18 IS SIGNAL) | 39 | 40 |
| | | CDR1 | 7 | 8 |
| | | CDR2 | 9 | 10 |
| | | CDR3 | 11 | 12 |
| HB20 | H CHAIN | FULL LENGTH (aa 1-19 IS SIGNAL) | 41 | 42 |
| | | CDR1 | 13 | 14 |
| | | CDR2 | 15 | 16 |
| | | CDR3 | 17 | 18 |
| HB20 | L CHAIN | FULL LENGTH (aa 1-20 IS SIGNAL) | 43 | 44 |
| | | CDR1 | 19 | 20 |
| | | CDR2 | 21 | 22 |
| | | CDR3 | 23 | 24 |
| HC15 | H CHAIN | FULL LENGTH (aa 1-19 IS SIGNAL) | 45 | 46 |
| | | CDR1 | 25 | 26 |
| | | CDR2 | 27 | 28 |
| | | CDR3 | 29 | 30 |
| HC15 | L CHAIN | FULL LENGTH (aa 1-22 IS SIGNAL) | 47 | 48 |
| | | CDR1 | 31 | 32 |
| | | CDR2 | 33 | 34 |
| | | CDR3 | 35 | 36 |

US 9,023,993 B2

SEQUENCE LISTING

<160> NUMBER OF SEQ ID NOS: 93

<210> SEQ ID NO 1
<211> LENGTH: 15
<212> TYPE: DNA
<213> ORGANISM: Mus musculus

<400> SEQUENCE: 1
agctactgga tgcac                                                    15

<210> SEQ ID NO 2
<211> LENGTH: 5
<212> TYPE: PRT
<213> ORGANISM: Mus musculus

<400> SEQUENCE: 2

Ser Tyr Trp Met His
1               5

<210> SEQ ID NO 3
<211> LENGTH: 51
<212> TYPE: DNA
<213> ORGANISM: Mus musculus

<400> SEQUENCE: 3
gagattaatc ctagcaacgg tcgtactaac tacaatgaga agttcaagag c         51

<210> SEQ ID NO 4
<211> LENGTH: 17
<212> TYPE: PRT
<213> ORGANISM: Mus musculus

<400> SEQUENCE: 4

Glu Ile Asn Pro Ser Asn Gly Arg Thr Asn Tyr Asn Glu Lys Phe Lys
1               5                   10                  15

Ser

<210> SEQ ID NO 5
<211> LENGTH: 15
<212> TYPE: DNA
<213> ORGANISM: Mus musculus

<400> SEQUENCE: 5
tccctctttg actac                                                  15

<210> SEQ ID NO 6
<211> LENGTH: 5
<212> TYPE: PRT
<213> ORGANISM: Mus musculus

<400> SEQUENCE: 6

Ser Leu Phe Asp Tyr
1               5

<210> SEQ ID NO 7
<211> LENGTH: 990
<212> TYPE: DNA
<213> ORGANISM: Mus musculus

<400> SEQUENCE: 7

| | |
|---|---|
| acaacaacag ccccatctgt ctatcccttg gtccctggct gcagtgacac atctggatcc | 60 |
| tcggtgacac tgggatgcct tgtcaaaggc tacttccctg agccggtaac tgtaaaatgg | 120 |
| aactatggag ccctgtccag cggtgtgcgc acagtctcat ctgtcctgca gtctgggttc | 180 |
| tattccctca gcagcttggt gactgtaccc tccagcacct ggcccagcca gactgtcatc | 240 |
| tgcaacgtag cccacccagc cagcaagact gagttgatca gagaatcga gcctagaata | 300 |
| cccaagccca gtaccccccc aggttcttca tgcccacctg taacatctt gggtggacca | 360 |
| tccgtcttca tcttcccccc aaagcccaag gatgcactca tgatctccct aaccccaag | 420 |
| gttacgtgtg tggtggtgga tgtgagcgag gatgacccag atgtccatgt cagctggttt | 480 |
| gtggacaaca agaagtaca cacagcctgg acacagcccc gtgaagctca gtacaacagt | 540 |
| accttccgag tggtcagtgc cctccccatc cagcaccagg actggatgag gggcaaggag | 600 |
| ttcaaatgca aggtcaacaa caaagccctc ccagcccca tcgagagaac catctcaaaa | 660 |

```
cccaaaggaa gagcccagac acctcaagta taccccatac ccccacctcg tgaacaaatg      720
tccaagaaga aggttagtct gacctgcctg gtcaccaact tcttctctga agccatcagt      780
gtggagtggg aaaggaacgg agaactggag caggattaca agaacactcc acccatcctg      840
gactcagatg ggacctactt cctctacagc aagctcactg tggatacaga cagttggttg      900
caaggagaaa tttttacctg ctccgtggtg catgaggctc tccataacca ccacacacag      960
aagaacctgt ctcgctcccc tggtaaatga                                       990
```

<210> SEQ ID NO 8
<211> LENGTH: 329
<212> TYPE: PRT
<213> ORGANISM: Mus musculus

<400> SEQUENCE: 8

```
Thr Thr Thr Ala Pro Ser Val Tyr Pro Leu Val Pro Gly Cys Ser Asp
  1               5                  10                  15

Thr Ser Gly Ser Ser Val Thr Leu Gly Cys Leu Val Lys Gly Tyr Phe
             20                  25                  30

Pro Glu Pro Val Thr Val Lys Trp Asn Tyr Gly Ala Leu Ser Ser Gly
         35                  40                  45

Val Arg Thr Val Ser Ser Val Leu Gln Ser Gly Phe Tyr Ser Leu Ser
     50                  55                  60

Ser Leu Val Thr Val Pro Ser Ser Thr Trp Pro Ser Gln Thr Val Ile
 65                  70                  75                  80

Cys Asn Val Ala His Pro Ala Ser Lys Thr Glu Leu Ile Lys Arg Ile
                 85                  90                  95

Glu Pro Arg Ile Pro Lys Pro Ser Thr Pro Pro Gly Ser Ser Cys Pro
            100                 105                 110

Pro Gly Asn Ile Leu Gly Gly Pro Ser Val Phe Ile Phe Pro Pro Lys
        115                 120                 125

Pro Lys Asp Ala Leu Met Ile Ser Leu Thr Pro Lys Val Thr Cys Val
    130                 135                 140

Val Val Asp Val Ser Glu Asp Asp Pro Asp Val His Val Ser Trp Phe
145                 150                 155                 160

Val Asp Asn Lys Glu Val His Thr Ala Trp Thr Gln Pro Arg Glu Ala
                165                 170                 175

Gln Tyr Asn Ser Thr Phe Arg Val Val Ser Ala Leu Pro Ile Gln His
            180                 185                 190

Gln Asp Trp Met Arg Gly Lys Glu Phe Lys Cys Lys Val Asn Asn Lys
        195                 200                 205

Ala Leu Pro Ala Pro Ile Glu Arg Thr Ile Ser Lys Pro Lys Gly Arg
    210                 215                 220

Ala Gln Thr Pro Gln Val Tyr Thr Ile Pro Pro Arg Glu Gln Met
225                 230                 235                 240

Ser Lys Lys Lys Val Ser Leu Thr Cys Leu Val Thr Asn Phe Phe Ser
                245                 250                 255

Glu Ala Ile Ser Val Glu Trp Glu Arg Asn Gly Glu Leu Glu Gln Asp
            260                 265                 270

Tyr Lys Asn Thr Pro Pro Ile Leu Asp Ser Asp Gly Thr Tyr Phe Leu
        275                 280                 285

Tyr Ser Lys Leu Thr Val Asp Thr Asp Ser Trp Leu Gln Gly Glu Ile
    290                 295                 300

Phe Thr Cys Ser Val Val His Glu Ala Leu His Asn His His Thr Gln
```

```
                305                 310                 315                 320
Lys Asn Leu Ser Arg Ser Pro Gly Lys
                325

<210> SEQ ID NO 9
<211> LENGTH: 984
<212> TYPE: DNA
<213> ORGANISM: Homo sapiens

<400> SEQUENCE: 9
gcctccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa atga                                            984

<210> SEQ ID NO 10
<211> LENGTH: 327
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 11
<211> LENGTH: 36
<212> TYPE: DNA
<213> ORGANISM: Mus musculus

<400> SEQUENCE: 11
agtgccagct caagtataag ttccaattac ttgcat                             36

<210> SEQ ID NO 12
<211> LENGTH: 12
<212> TYPE: PRT
<213> ORGANISM: Mus musculus

<400> SEQUENCE: 12

Ser Ala Ser Ser Ser Ile Ser Ser Asn Tyr Leu His
1               5                   10

<210> SEQ ID NO 13
<211> LENGTH: 21
<212> TYPE: DNA
<213> ORGANISM: Mus musculus

<400> SEQUENCE: 13
aggacatcca atctggcttc t                                             21

<210> SEQ ID NO 14
<211> LENGTH: 7
<212> TYPE: PRT
<213> ORGANISM: Mus musculus

<400> SEQUENCE: 14

Arg Thr Ser Asn Leu Ala Ser
```

<210> SEQ ID NO 15
<211> LENGTH: 27
<212> TYPE: DNA
<213> ORGANISM: Mus musculus

<400> SEQUENCE: 15
cagcagggta gtagtatacc attcacg                                          27

<210> SEQ ID NO 16
<211> LENGTH: 9
<212> TYPE: PRT
<213> ORGANISM: Mus musculus

<400> SEQUENCE: 16

Gln Gln Gly Ser Ser Ile Pro Phe Thr
1               5

<210> SEQ ID NO 17
<211> LENGTH: 324
<212> TYPE: DNA
<213> ORGANISM: Mus musculus

<400> SEQUENCE: 17
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga cgacaaaaat ggcgtcctga acagttggac tgatcaggac     180
agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg ttag                                            324

<210> SEQ ID NO 18
<211> LENGTH: 107
<212> TYPE: PRT
<213> ORGANISM: Mus musculus

<400> SEQUENCE: 18

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 19
<211> LENGTH: 324
<212> TYPE: DNA
<213> ORGANISM: Homo sapiens

<400> SEQUENCE: 19

```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttga                                            324
```

```
<210> SEQ ID NO 20
<211> LENGTH: 107
<212> TYPE: PRT
<213> ORGANISM: Homo sapiens

<400> SEQUENCE: 20
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 21
<211> LENGTH: 15
<212> TYPE: DNA
<213> ORGANISM: Mus musculus

<400> SEQUENCE: 21
ggctatggta taaac                                                       15

<210> SEQ ID NO 22
<211> LENGTH: 5
<212> TYPE: PRT
<213> ORGANISM: Mus musculus

<400> SEQUENCE: 22
```

Gly Tyr Gly Ile Asn
1               5

```
<210> SEQ ID NO 23
<211> LENGTH: 48
<212> TYPE: DNA
<213> ORGANISM: Mus musculus

<400> SEQUENCE: 23
atgatctggg gtgatggaag cgcagactat aattcagctc tcaaatcc                   48

<210> SEQ ID NO 24
<211> LENGTH: 16
<212> TYPE: PRT
<213> ORGANISM: Mus musculus
```

<400> SEQUENCE: 24

Met Ile Trp Gly Asp Gly Ser Ala Asp Tyr Asn Ser Ala Leu Lys Ser
1               5                   10                  15

<210> SEQ ID NO 25
<211> LENGTH: 30
<212> TYPE: DNA
<213> ORGANISM: Mus musculus

<400> SEQUENCE: 25
ggggattact acggctacag gttttcttac                                      30

<210> SEQ ID NO 26
<211> LENGTH: 10
<212> TYPE: PRT
<213> ORGANISM: Mus musculus

<400> SEQUENCE: 26

Gly Asp Tyr Tyr Gly Tyr Arg Phe Ser Tyr
1               5                   10

<210> SEQ ID NO 27
<211> LENGTH: 975
<212> TYPE: DNA
<213> ORGANISM: Mus musculus

<400> SEQUENCE: 27

| | |
|---|---|
| gccaaaacga cacccccatc tgtctatcca ctggcccctg gatctgctgc ccaaactaac | 60 |
| tccatggtga ccctgggatg cctggtcaag ggctatttcc ctgagccagt gacagtgacc | 120 |
| tggaactctg gatccctgtc cagcggtgtg cacaccttcc cagctgtcct gcagtctgac | 180 |
| ctctacactc tgagcagctc agtgactgtc ccctccagca cctggcccag ccagaccgtc | 240 |
| acctgcaacg ttgcccaccc ggccagcagc accaaggtgg acaagaaaat tgtgcccagg | 300 |
| gattgtggtt gtaagccttg catatgtaca gtcccagaag tatcatctgt cttcatcttc | 360 |
| cccccaaagc ccaaggatgt gctcaccatt actctgactc taaggtcac gtgtgttgtg | 420 |
| gtagacatca gcaaggatga tcccgaggtc cagttcagct ggtttgtaga tgatgtggag | 480 |
| gtgcacacag ctcagacaaa accccgggag gagcagttca acagcacttt ccgttcagtc | 540 |
| agtgaacttc ccatcatgca ccaggactgg ctcaatggca aggagttcaa atgcagggtc | 600 |
| aacagtgcag ctttccctgc ccccatcgag aaaaccatct ccaaaaccaa aggcagaccg | 660 |
| aaggctccac aggtgtacac cattccacct cccaaggagc agatggccaa ggataaagtc | 720 |
| agtctgacct gcatgataac agacttcttc cctgaagaca ttactgtgga gtggcagtgg | 780 |
| aatgggcagc cagcggagaa ctacaagaac actcagccca tcatgg acac agatggctct | 840 |
| tacttcgtct acagcaagct caatgtgcag aagagcaact gggaggcagg aaatactttc | 900 |
| acctgctctg tgttacatga gggcctgcac aaccaccata ctgagaagag cctctcccac | 960 |
| tctcctggta aatga | 975 |

<210> SEQ ID NO 28
<211> LENGTH: 324
<212> TYPE: PRT
<213> ORGANISM: Mus musculus

<400> SEQUENCE: 28

Ala Lys Thr Thr Pro Pro Ser Val Tyr Pro Leu Ala Pro Gly Ser Ala
1               5                   10                  15

```
Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 29
<211> LENGTH: 51
<212> TYPE: DNA
<213> ORGANISM: Mus musculus

<400> SEQUENCE: 29
aagtccagtc aaagtgtttt atacagttca aatcagaaga acttcttggc c          51

<210> SEQ ID NO 30
<211> LENGTH: 17
<212> TYPE: PRT
<213> ORGANISM: Mus musculus

<400> SEQUENCE: 30

Lys Ser Ser Gln Ser Val Leu Tyr Ser Ser Asn Gln Lys Asn Phe Leu
1               5                   10                  15
```

Ala

<210> SEQ ID NO 31
<211> LENGTH: 21
<212> TYPE: DNA
<213> ORGANISM: Mus musculus

<400> SEQUENCE: 31
tgggcatcca ctagggaatc t                                              21

<210> SEQ ID NO 32
<211> LENGTH: 7
<212> TYPE: PRT
<213> ORGANISM: Mus musculus

<400> SEQUENCE: 32

Trp Ala Ser Thr Arg Glu Ser
1               5

<210> SEQ ID NO 33
<211> LENGTH: 24
<212> TYPE: DNA
<213> ORGANISM: Mus musculus

<400> SEQUENCE: 33
catcaatacc tctcctcgta tacg                                           24

<210> SEQ ID NO 34
<211> LENGTH: 8
<212> TYPE: PRT
<213> ORGANISM: Mus musculus

<400> SEQUENCE: 34

His Gln Tyr Leu Ser Ser Tyr Thr
1               5

<210> SEQ ID NO 35
<211> LENGTH: 15
<212> TYPE: DNA
<213> ORGANISM: Mus musculus

<400> SEQUENCE: 35
ggctactaca tgcac                                                     15

<210> SEQ ID NO 36
<211> LENGTH: 5
<212> TYPE: PRT
<213> ORGANISM: Mus musculus

<400> SEQUENCE: 36

Gly Tyr Tyr Met His
1               5

<210> SEQ ID NO 37
<211> LENGTH: 51
<212> TYPE: DNA
<213> ORGANISM: Mus musculus

<400> SEQUENCE: 37
gagattaatc ctagaactgg tattactacc tacaaccaga gttcaaggc c              51

<210> SEQ ID NO 38
<211> LENGTH: 17

<210> SEQ ID NO 38
<211> LENGTH: 16
<212> TYPE: PRT
<213> ORGANISM: Mus musculus

<400> SEQUENCE: 38

Glu Ile Asn Pro Arg Thr Gly Ile Thr Thr Tyr Asn Gln Lys Phe Lys
1               5                   10                  15

Ala

<210> SEQ ID NO 39
<211> LENGTH: 27
<212> TYPE: DNA
<213> ORGANISM: Mus musculus

<400> SEQUENCE: 39
gttggcagct cgggcccttt tacgtac                                    27

<210> SEQ ID NO 40
<211> LENGTH: 9
<212> TYPE: PRT
<213> ORGANISM: Mus musculus

<400> SEQUENCE: 40

Val Gly Ser Ser Gly Pro Phe Thr Tyr
1               5

<210> SEQ ID NO 41
<211> LENGTH: 33
<212> TYPE: DNA
<213> ORGANISM: Mus musculus

<400> SEQUENCE: 41
cgggcaagtc aggacattca tggttattta aac                             33

<210> SEQ ID NO 42
<211> LENGTH: 11
<212> TYPE: PRT
<213> ORGANISM: Mus musculus

<400> SEQUENCE: 42

Arg Ala Ser Gln Asp Ile His Gly Tyr Leu Asn
1               5                   10

<210> SEQ ID NO 43
<211> LENGTH: 21
<212> TYPE: DNA
<213> ORGANISM: Mus musculus

<400> SEQUENCE: 43
gaaacatcca atttagattc t                                          21

<210> SEQ ID NO 44
<211> LENGTH: 7
<212> TYPE: PRT
<213> ORGANISM: Mus musculus

<400> SEQUENCE: 44

Glu Thr Ser Asn Leu Asp Ser
1               5

<210> SEQ ID NO 45
<211> LENGTH: 24
<212> TYPE: DNA
<213> ORGANISM: Mus musculus

<400> SEQUENCE: 45
ctacaatatg ctagttcgct cacg                                              24

<210> SEQ ID NO 46
<211> LENGTH: 8
<212> TYPE: PRT
<213> ORGANISM: Mus musculus

<400> SEQUENCE: 46

Leu Gln Tyr Ala Ser Ser Leu Thr
1               5

<210> SEQ ID NO 47
<211> LENGTH: 399
<212> TYPE: DNA
<213> ORGANISM: Mus musculus

<400> SEQUENCE: 47
atgggatgga gctatatcat cctcttttg gtagcaacag ctacagatgt ccactcccag        60
gtccaactgc agcagcctgg ggctgaactg gtgaagcctg ggcttcagt gaagctgtcc       120 tgcaaggctt ctggctacac cttcaccagc tactggatgc actgggtgaa gcagaggcct     180
ggacaaggcc ttgagtggat tggagagatt aatcctagca acggtcgtac taactacaat     240
gagaagttca agagcaaggc cacactgact gtagacaaat cctccagcac agcctacatg     300
caactcagca gcctgacatc tgaggactct gcggtctatt actgtgtatg gtccctcttt     360
gactactggg gccaaggcac cactctcaca gtctcctca                             399

<210> SEQ ID NO 48
<211> LENGTH: 133
<212> TYPE: PRT
<213> ORGANISM: Mus musculus

<400> SEQUENCE: 48

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
        50                  55                  60

Glu Trp Ile Gly Glu Ile Asn Pro Ser Asn Gly Arg Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Val Trp Ser Leu Phe Asp Tyr Trp Gly Gln Gly Thr Thr
        115                 120                 125

Leu Thr Val Ser Ser
    130

<210> SEQ ID NO 49
<211> LENGTH: 378
<212> TYPE: DNA
<213> ORGANISM: Mus musculus

<400> SEQUENCE: 49

```
atgcagatta tcagcttgct gctaatcagt gtcacagtca tagtgtctaa tggagaaatt    60
gtgctcaccc agtctccaac caccatggct gcatctcccg gggagaagat cactatcacc   120
tgcagtgcca gctcaagtat aagttccaat tacttgcatt ggtatcagca gaagccagga   180
ttctccccta aactcttgat ttataggaca tccaatctgg cttctggagt cccagctcgc   240
ttcagtggca gtgggtctgg gacctcttac tctctcacaa ttggcaccat ggaggctgaa   300
gatgttgcca cttactactg ccagcaggga gtagtatac cattcacgtt cggctcgggg    360
acaaagttgg aaataaaa                                                 378
```

<210> SEQ ID NO 50
<211> LENGTH: 126
<212> TYPE: PRT
<213> ORGANISM: Mus musculus

<400> SEQUENCE: 50

```
Met Gln Ile Ile Ser Leu Leu Leu Ile Ser Val Thr Val Ile Val Ser
1               5                   10                  15

Asn Gly Glu Ile Val Leu Thr Gln Ser Pro Thr Thr Met Ala Ala Ser
            20                  25                  30

Pro Gly Glu Lys Ile Thr Ile Thr Cys Ser Ala Ser Ser Ser Ile Ser
        35                  40                  45

Ser Asn Tyr Leu His Trp Tyr Gln Gln Lys Pro Gly Phe Ser Pro Lys
    50                  55                  60

Leu Leu Ile Tyr Arg Thr Ser Asn Leu Ala Ser Gly Val Pro Ala Arg
65                  70                  75                  80

Phe Ser Gly Ser Gly Ser Gly Thr Ser Tyr Ser Leu Thr Ile Gly Thr
                85                  90                  95

Met Glu Ala Glu Asp Val Ala Thr Tyr Tyr Cys Gln Gln Gly Ser Ser
            100                 105                 110

Ile Pro Phe Thr Phe Gly Ser Gly Thr Lys Leu Glu Ile Lys
        115                 120                 125
```

<210> SEQ ID NO 51
<211> LENGTH: 411
<212> TYPE: DNA
<213> ORGANISM: Mus musculus

<400> SEQUENCE: 51

```
atggctgtcc tggcattact cttctgcctg gtaacattcc caagctgtat cctttcccag    60
gtgcagctga aggagtcagg acctggcctg gtggcgccct cacagagcct gtccatcaca   120
tgcaccgtct cagggttctc attaaccggc tatggtataa actgggttcg ccagcctcca   180
ggaaagggtc tggagtggct gggaatgatc tgggtgatg aagcgcaga ctataattca     240 gctctcaaat ccagactgag catccgcaag gacaactcca gagccaagt tttcttagaa    300 atgaacagtc tgcaaactga tgacacagcc aggtactact gtgccagagg ggattactac   360
ggctacaggt tttcttactg gggccaaggg actctggtca ctgtctctgc a            411
```

<210> SEQ ID NO 52
<211> LENGTH: 137
<212> TYPE: PRT
<213> ORGANISM: Mus musculus

<400> SEQUENCE: 52

```
Met Ala Val Leu Ala Leu Leu Phe Cys Leu Val Thr Phe Pro Ser Cys
1               5                   10                  15
```

Ile Ser Gln Val Gln Leu Lys Glu Ser Gly Pro Gly Leu Val Ala
        20                  25                  30

Pro Ser Gln Ser Leu Ser Ile Thr Cys Thr Val Ser Gly Phe Ser Leu
            35                  40                  45

Thr Gly Tyr Gly Ile Asn Trp Val Arg Gln Pro Pro Gly Lys Gly Leu
    50                  55                  60

Glu Trp Leu Gly Met Ile Trp Gly Asp Gly Ser Ala Asp Tyr Asn Ser
65                  70                  75                  80

Ala Leu Lys Ser Arg Leu Ser Ile Arg Lys Asp Asn Ser Lys Ser Gln
                85                  90                  95

Val Phe Leu Glu Met Asn Ser Leu Gln Thr Asp Asp Thr Ala Arg Tyr
            100                 105                 110

Tyr Cys Ala Arg Gly Asp Tyr Tyr Gly Tyr Arg Phe Ser Tyr Trp Gly
        115                 120                 125

Gln Gly Thr Leu Val Thr Val Ser Ala
    130                 135

<210> SEQ ID NO 53
<211> LENGTH: 396
<212> TYPE: DNA
<213> ORGANISM: Mus musculus

<400> SEQUENCE: 53
atggaatcac agactcaggt cttcctctcc ctgctgctct gggtatctgg tacctttggg      60
aacattatgc tgacacagtc gccatcatct ctggctgtgt ctgcaggaga aaaggtcact     120
atgagctgta agtccagtca agtgttttta tacagttcaa atcagaagaa cttcttggcc     180
tggtaccagc agaaaccagg gcagtctcct aaactgctga tctactgggc atccactagg     240
gaatctggtg tccctgatcg cttcgcaggc agtggatctg gacagatttt actcttacc     300 atcagcagtg tacaaactga agacctggca gtttattact gtcatcaata cctctcctcg     360
tatacgttcg agggggggac caagctggaa ataaaa                              396

<210> SEQ ID NO 54
<211> LENGTH: 132
<212> TYPE: PRT
<213> ORGANISM: Mus musculus

<400> SEQUENCE: 54

Met Glu Ser Gln Thr Gln Val Phe Leu Ser Leu Leu Trp Val Ser
1               5                   10                  15

Gly Thr Phe Gly Asn Ile Met Leu Thr Gln Ser Pro Ser Ser Leu Ala
            20                  25                  30

Val Ser Ala Gly Glu Lys Val Thr Met Ser Cys Lys Ser Ser Gln Ser
        35                  40                  45

Val Leu Tyr Ser Ser Asn Gln Lys Asn Phe Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ala Gly Ser Gly Ser Gly Thr Asp
                85                  90                  95

Phe Thr Leu Thr Ile Ser Ser Val Gln Thr Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Lys
    130

<210> SEQ ID NO 55
<211> LENGTH: 411
<212> TYPE: DNA
<213> ORGANISM: Mus musculus

<400> SEQUENCE: 55
atgggatgga actggatctt tattttaatc ctgtcagtaa ctacaggtgt ccactctgag      60
gtccagctgc agcagtctgg acctgagctg gtgaagcctg gggcttcagt gaagatatcc     120
tgcaaggctt ctggttactc attcactggc tactacatgc actgggtgaa gcaaagtcct     180 gaaagagac ttgagtggat tggagagatt aatcctagaa ctggtattac tacctacaac     240
cagaagttca aggccaaggc cacattgact gtagacaaat cctccagcac agcctacatg     300
cagctcaaga gcctgacatc tgaggactct gcagtctatt actgtgcaag agttggcagc    360
tcgggccctt ttacgtactg gggccaaggg actctggtca ctgtctctgc a             411

<210> SEQ ID NO 56
<211> LENGTH: 137
<212> TYPE: PRT
<213> ORGANISM: Mus musculus

<400> SEQUENCE: 56

Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Tyr Met His Trp Val Lys Gln Ser Pro Glu Lys Arg Leu
    50                  55                  60

Glu Trp Ile Gly Glu Ile Asn Pro Arg Thr Gly Ile Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Val Gly Ser Ser Gly Pro Phe Thr Tyr Trp Gly
        115                 120                 125

Gln Gly Thr Leu Val Thr Val Ser Ala
    130                 135

<210> SEQ ID NO 57
<211> LENGTH: 384
<212> TYPE: DNA
<213> ORGANISM: Mus musculus

<400> SEQUENCE: 57
atggacatga gggctcctgc tcaggttttt ggcttcttgt tgctctggtt tccaggtgcc     60
agatgtgaca tccagatgac ccagtctcca tcctccttat ctgcctctct gggagaaaga    120
gtcagtctca cttgccgggc aagtcaggac attcatggtt atttaaactt gtttcagcag    180
aaaccaggtg aaactattaa acacctgatc tatgaaacat ccaatttaga ttctggtgtc    240
ccgaaaaggt tcagtggcag taggtctggg tcagattatt ctctcattat cggcagcctt    300
gagtctgaag attttgcaga ctattactgt ctacaatatg ctagttcgct cacgttcggt    360
gctgggacca agctggagct gaaa                                              384

<210> SEQ ID NO 58
<211> LENGTH: 128
<212> TYPE: PRT
<213> ORGANISM: Mus musculus

<400> SEQUENCE: 58

Met Asp Met Arg Ala Pro Ala Gln Val Phe Gly Phe Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile His Gly Tyr Leu Asn Leu Phe Gln Gln Lys Pro Gly Glu
    50                  55                  60

Thr Ile Lys His Leu Ile Tyr Glu Thr Ser Asn Leu Asp Ser Gly Val
65                  70                  75                  80

Pro Lys Arg Phe Ser Gly Ser Arg Ser Gly Ser Asp Tyr Ser Leu Ile
                85                  90                  95

Ile Gly Ser Leu Glu Ser Glu Asp Phe Ala Asp Tyr Tyr Cys Leu Gln
            100                 105                 110

Tyr Ala Ser Ser Leu Thr Phe Gly Ala Gly Thr Lys Leu Glu Leu Lys
        115                 120                 125

<210> SEQ ID NO 59
<211> LENGTH: 627
<212> TYPE: DNA
<213> ORGANISM: Homo sapiens

<400> SEQUENCE: 59
atgaagctgc tgccgtcggt ggtgctgaag ctctttctgg ctgcagttct ctcggcactg    60
gtgactggcg agagcctgga gcggcttcgg agagggctag ctgctggaac cagcaacccg   120
gaccctccca ctgtatccac ggaccagctg ctacccctag gaggcggccg ggaccggaaa   180
gtccgtgact tgcaagaggc agatctggac cttttgagag tcactttatc ctccaagcca   240
caagcactgg ccacaccaaa caaggaggag cacgggaaaa gaaagaagaa aggcaagggg   300
ctagggaaga gagggacccc atgtcttcgg aaatacaagg acttctgcat ccatggagaa   360
tgcaaatatg tgaaggagct ccgggctccc tcctgcatct gccacccggg ttaccatgga   420
gagaggtgtc atgggctgag cctcccagtg gaaaatcgct tatataccta tgaccacaca   480
accatcctgg ccgtggtggc tgtggtgctg tcatctgtct gtctgctggt catcgtgggg   540
cttctcatgt ttaggtacca taggagagga ggttatgatg tggaaaatga agagaaagtg   600
aagttgggca tgactaattc ccactga                                       627

<210> SEQ ID NO 60
<211> LENGTH: 208
<212> TYPE: PRT
<213> ORGANISM: Homo sapiens

<400> SEQUENCE: 60

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

```
Leu Ala Ala Gly Thr Ser Asn Pro Asp Pro Thr Val Ser Thr Asp
             35                  40                  45

Gln Leu Leu Pro Leu Gly Gly Arg Asp Arg Lys Val Arg Asp Leu
 50                  55                  60

Gln Glu Ala Asp Leu Asp Leu Leu Arg Val Thr Leu Ser Ser Lys Pro
 65                  70                  75                  80

Gln Ala Leu Ala Thr Pro Asn Lys Glu Glu His Gly Lys Arg Lys Lys
                 85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
        130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
            195                 200                 205

<210> SEQ ID NO 61
<211> LENGTH: 4
<212> TYPE: PRT
<213> ORGANISM: Artificial
<220> FEATURE:
<223> OTHER INFORMATION: Artificial Linker

<400> SEQUENCE: 61

Gly Gly Gly Ser
1

<210> SEQ ID NO 62
<211> LENGTH: 4
<212> TYPE: PRT
<213> ORGANISM: Artificial
<220> FEATURE:
<223> OTHER INFORMATION: Artificial Linker

<400> SEQUENCE: 62

Ser Gly Gly Gly
1

<210> SEQ ID NO 63
<211> LENGTH: 5
<212> TYPE: PRT
<213> ORGANISM: Artificial
<220> FEATURE:
<223> OTHER INFORMATION: Artificial Linker

<400> SEQUENCE: 63

Gly Gly Gly Gly Ser
1               5

<210> SEQ ID NO 64
<211> LENGTH: 5
<212> TYPE: PRT
<213> ORGANISM: Artificial
<220> FEATURE:
<223> OTHER INFORMATION: Artificial Linker
```

-continued

<400> SEQUENCE: 64

Ser Gly Gly Gly Gly
1               5

<210> SEQ ID NO 65
<211> LENGTH: 6
<212> TYPE: PRT
<213> ORGANISM: Artificial
<220> FEATURE:
<223> OTHER INFORMATION: Artificial Linker

<400> SEQUENCE: 65

Gly Gly Gly Gly Gly Ser
1               5

<210> SEQ ID NO 66
<211> LENGTH: 6
<212> TYPE: PRT
<213> ORGANISM: Artificial
<220> FEATURE:
<223> OTHER INFORMATION: Artificial Linker

<400> SEQUENCE: 66

Ser Gly Gly Gly Gly Gly
1               5

<210> SEQ ID NO 67
<211> LENGTH: 7
<212> TYPE: PRT
<213> ORGANISM: Artificial
<220> FEATURE:
<223> OTHER INFORMATION: Artificial Linker

<400> SEQUENCE: 67

Gly Gly Gly Gly Gly Gly Ser
1               5

<210> SEQ ID NO 68
<211> LENGTH: 7
<212> TYPE: PRT
<213> ORGANISM: Artificial
<220> FEATURE:
<223> OTHER INFORMATION: Artificial Linker

<400> SEQUENCE: 68

Ser Gly Gly Gly Gly Gly Gly
1               5

<210> SEQ ID NO 69
<211> LENGTH: 21
<212> TYPE: DNA
<213> ORGANISM: Artificial
<220> FEATURE:
<223> OTHER INFORMATION: PCR primer

<400> SEQUENCE: 69
atgaagctgc tgccgtcggt g                                           21

<210> SEQ ID NO 70
<211> LENGTH: 22
<212> TYPE: DNA
<213> ORGANISM: Artificial
<220> FEATURE:
<223> OTHER INFORMATION: PCR primer

<400> SEQUENCE: 70

```
tcagtgggaa ttagtcatgc cc                                              22

<210> SEQ ID NO 71
<211> LENGTH: 34
<212> TYPE: DNA
<213> ORGANISM: Artificial
<220> FEATURE:
<223> OTHER INFORMATION: PCR primer

<400> SEQUENCE: 71
taagtcgacc accatgaagc tgctgccgtc ggtg                                 34

<210> SEQ ID NO 72
<211> LENGTH: 60
<212> TYPE: DNA
<213> ORGANISM: Artificial
<220> FEATURE:
<223> OTHER INFORMATION: PCR primer

<400> SEQUENCE: 72
tttgcggccg ctcacttgtc atcgtcgtcc ttgtagtcgt gggaattagt catgcccaac     60

<210> SEQ ID NO 73
<211> LENGTH: 30
<212> TYPE: DNA
<213> ORGANISM: Artificial
<220> FEATURE:
<223> OTHER INFORMATION: PCR primer

<400> SEQUENCE: 73
aaagaattcc accatgaagc tgctgccgtc                                      30

<210> SEQ ID NO 74
<211> LENGTH: 40
<212> TYPE: DNA
<213> ORGANISM: Artificial
<220> FEATURE:
<223> OTHER INFORMATION: PCR primer

<400> SEQUENCE: 74
tatcggtccg cgaggttcga ggctcagccc atgacacctc                           40

<210> SEQ ID NO 75
<211> LENGTH: 38
<212> TYPE: DNA
<213> ORGANISM: Artificial
<220> FEATURE:
<223> OTHER INFORMATION: PCR primer

<400> SEQUENCE: 75
cgattttcca ctgtgctgct cagcccatga cacctctc                             38

<210> SEQ ID NO 76
<211> LENGTH: 39
<212> TYPE: DNA
<213> ORGANISM: Artificial
<220> FEATURE:
<223> OTHER INFORMATION: PCR primer

<400> SEQUENCE: 76
tgggctgagc agcacagtgg aaaatcgctt atataccta                            39

<210> SEQ ID NO 77
<211> LENGTH: 3633
<212> TYPE: DNA
```

<213> ORGANISM: Homo sapiens

<400> SEQUENCE: 77

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg gagctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat tccgagacga agccacgtgc     780
aaggacacct gccccccact catgctctac aaccccacca cgtaccagat ggatgtgaac     840
cccgagggca atacagcttt ggtgccacct gcgtgaaga agtgtccccg taattatgtg     900
gtgacagatc acggctcgtg cgtccgagcc tgtggggccg acagctatga gatggaggaa     960
gacggcgtcc gcaagtgtaa gaagtgcgaa gggccttgcc gcaaagtgtg taacggaata    1020
ggtattggtg aatttaaaga ctcactctcc ataaatgcta cgaatattaa cacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaactg    1440
tttgggacct ccggtcagaa aaccaaaatt ataagcaaca gaggtgaaaa cagctgcaag    1500
gccacaggcc aggtctgcca tgccttgtgc tcccccgagg gctgctgggg cccggagccc    1560
agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggcccccac tgcgtcaaga cctgcccggc aggagtcatg    1800
ggagaaaaca cacccctggt ctggaagtac gcagacgccg ccatgtgtgt ccacctgtgc    1860
catccaaaact gcacctacgg atgcactggg ccaggtcttg aaggctgtcc aacgaatggg    1920
cctaagatcc cgtccatcgc cactgggatg gtgggggccc tcctcttgct gctggtggtg    1980
gccctgggga tcgcctcttc catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
```

```
gatgaagcct acgtgatggc cagcgtggac aacccccacg tgtgccgcct gctgggcatc   2340
tgcctcacct ccaccgtgca gctcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag accccagcg ctaccttgtc   2940 attcagggga tgaaagaat gcatttgcca gtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
aaggaagaca gcttcttgca gcgatacagc tcagacccca caggcgcctt gactgaggac   3240
agcatagacg acaccttcct cccagtgcct gaatacataa accagtccgt tcccaaaagg   3300
cccgctggct ctgtgcagaa tcctgtctat cacaatcagc ctctgaaccc cgcgcccagc   3360
agagacccac actaccagga ccccacagc actgcagtgg gcaaccccga gtatctcaac   3420
actgtccagc ccacctgtgt caacagcaca ttcgacagcc ctgcccactg ggcccagaaa   3480
ggcagccacc aaattagcct ggacaaccct gactaccagc aggacttctt tcccaaggaa   3540
gccaagccaa atggcatctt taagggctcc acagctgaaa atgcagaata cctaagggtc   3600
gcgccacaaa gcagtgaatt tattggagca tga                               3633
```

<210> SEQ ID NO 78
<211> LENGTH: 1210
<212> TYPE: PRT
<213> ORGANISM: Homo sapiens

<400> SEQUENCE: 78

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125
```

-continued

```
Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
```

```
                545                 550                 555                 560
Glu Cys Leu Pro Gln Ala Met Asn Ile Thr Cys Thr Gly Arg Gly Pro
                    565                 570                 575
Asp Asn Cys Ile Gln Cys Ala His Tyr Ile Asp Gly Pro His Cys Val
                    580                 585                 590
Lys Thr Cys Pro Ala Gly Val Met Gly Glu Asn Asn Thr Leu Val Trp
                    595                 600                 605
Lys Tyr Ala Asp Ala Gly His Val Cys His Leu Cys His Pro Asn Cys
                    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                    645                 650                 655
Leu Leu Val Val Ala Leu Gly Ile Gly Leu Phe Met Arg Arg Arg His
                    660                 665                 670
Ile Val Arg Lys Arg Thr Leu Arg Arg Leu Leu Gln Glu Arg Glu Leu
                    675                 680                 685
Val Glu Pro Leu Thr Pro Ser Gly Glu Ala Pro Asn Gln Ala Leu Leu
                    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                    725                 730                 735
Lys Val Lys Ile Pro Val Ala Ile Lys Glu Leu Arg Glu Ala Thr Ser
                    740                 745                 750
Pro Lys Ala Asn Lys Glu Ile Leu Asp Glu Ala Tyr Val Met Ala Ser
                    755                 760                 765
Val Asp Asn Pro His Val Cys Arg Leu Leu Gly Ile Cys Leu Thr Ser
                    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                    805                 810                 815
Trp Cys Val Gln Ile Ala Lys Gly Met Asn Tyr Leu Glu Asp Arg Arg
                    820                 825                 830
Leu Val His Arg Asp Leu Ala Ala Arg Asn Val Leu Val Lys Thr Pro
                    835                 840                 845
Gln His Val Lys Ile Thr Asp Phe Gly Leu Ala Lys Leu Leu Gly Ala
                    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                    885                 890                 895
Val Trp Ser Tyr Gly Val Thr Val Trp Glu Leu Met Thr Phe Gly Ser
                    900                 905                 910
Lys Pro Tyr Asp Gly Ile Pro Ala Ser Glu Ile Ser Ser Ile Leu Glu
                    915                 920                 925
Lys Gly Glu Arg Leu Pro Gln Pro Pro Ile Cys Thr Ile Asp Val Tyr
                    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                    965                 970                 975
```

-continued

```
Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
         1010                 1015                 1020

Phe Ser  Ser Pro Ser Thr Ser  Arg Thr Pro Leu Leu  Ser Ser Leu
         1025                 1030                 1035

Ser Ala  Thr Ser Asn Asn Ser  Thr Val Ala Cys Ile  Asp Arg Asn
         1040                 1045                 1050

Gly Leu  Gln Ser Cys Pro Ile  Lys Glu Asp Ser Phe  Leu Gln Arg
         1055                 1060                 1065

Tyr Ser  Ser Asp Pro Thr Gly  Ala Leu Thr Glu Asp  Ser Ile Asp
         1070                 1075                 1080

Asp Thr  Phe Leu Pro Val Pro  Glu Tyr Ile Asn Gln  Ser Val Pro
         1085                 1090                 1095

Lys Arg  Pro Ala Gly Ser Val  Gln Asn Pro Val Tyr  His Asn Gln
         1100                 1105                 1110

Pro Leu  Asn Pro Ala Pro Ser  Arg Asp Pro His Tyr  Gln Asp Pro
         1115                 1120                 1125

His Ser  Thr Ala Val Gly Asn  Pro Glu Tyr Leu Asn  Thr Val Gln
         1130                 1135                 1140

Pro Thr  Cys Val Asn Ser Thr  Phe Asp Ser Pro Ala  His Trp Ala
         1145                 1150                 1155

Gln Lys  Gly Ser His Gln Ile  Ser Leu Asp Asn Pro  Asp Tyr Gln
         1160                 1165                 1170

Gln Asp  Phe Phe Pro Lys Glu  Ala Lys Pro Asn Gly  Ile Phe Lys
         1175                 1180                 1185

Gly Ser  Thr Ala Glu Asn Ala  Glu Tyr Leu Arg Val  Ala Pro Gln
         1190                 1195                 1200

Ser Ser  Glu Phe Ile Gly Ala
         1205                 1210

<210> SEQ ID NO 79
<211> LENGTH: 20
<212> TYPE: DNA
<213> ORGANISM: Artificial
<220> FEATURE:
<223> OTHER INFORMATION: PCR primer

<400> SEQUENCE: 79
atgcgaccct ccgggacggc                                              20

<210> SEQ ID NO 80
<211> LENGTH: 21
<212> TYPE: DNA
<213> ORGANISM: Artificial
<220> FEATURE:
<223> OTHER INFORMATION: PCR primer

<400> SEQUENCE: 80
cagtggcgat ggacgggatc t                                            21

<210> SEQ ID NO 81
<211> LENGTH: 34
<212> TYPE: DNA
<213> ORGANISM: Artificial
<220> FEATURE:
```

<223> OTHER INFORMATION: PCR primer

<400> SEQUENCE: 81
ttgcggccgc caccatgcga ccctccggga cggc      34

<210> SEQ ID NO 82
<211> LENGTH: 61
<212> TYPE: DNA
<213> ORGANISM: Artificial
<220> FEATURE:
<223> OTHER INFORMATION: PCR primer

<400> SEQUENCE: 82
accagatctc caggaaaatg tttaagtcag atggatcgga cgggatctta ggcccattcg      60
t      61

<210> SEQ ID NO 83
<211> LENGTH: 2514
<212> TYPE: DNA
<213> ORGANISM: Mus musculus

<400> SEQUENCE: 83
atggtagggc tgggagcctg caccctgact ggagttaccc tgatcttctt gctactcccc      60
agaagtctgg agagctgtgg acacatcgag atttcacccc ctgttgtccg cctgggggac     120
cctgtcctgg cctcttgcac catcagccca aactgcagca aactggacca acaggcaaag     180
atcttatgga gactgcaaga tgagcccatc aacctgggg acagacagca tcatctgcct     240
gatgggaccc aagagtccct catcactctg cctcacttga actacaccca ggccttcctc     300
ttctgcttag tgccatggga agacagcgtc caactcctgg atcaagctga gcttcacgca     360
ggctatcccc ctgccagccc ctcaaaccta tcctgcctca tgcacctcac caccaacagc     420
ctggtctgcc agtgggagcc aggtcctgag acccacctgc ccaccagctt catcctaaag     480
agcttcagga gccgcgccga ctgtcagtac caaggggaca ccatcccgga ttgtgtggca     540
aagaagaggc agaacaactg ctccatcccc cgaaaaaact tgctcctgta ccagtatatg     600
gccatctggg tgcaagcaga gaatatgcta gggtccagcg agtccccaaa gctgtgcctc     660
gaccccatgg atgttgtgaa attggagcct cccatgctgc aggccctgga cattggccct     720
gatgtagtct ctcaccagcc tggctgcctg tggctgagct ggaagccatg gaagcccagt     780
gagtacatgg aacaggagtg tgaacttcgc taccagccac agctcaaagg agccaactgg     840
actctggtgt ccacctgcc ttccagcaag gaccagtttg agctctgcgg gctccatcag     900
gccccagtct acaccctaca gatgcgatgc attcgctcat ctctgcctgg attctggagc     960
ccctggagcc ccggcctgca gctgaggcct accatgaagg cccccaccat cagactggac    1020
acgtggtgtc agaagaagca actagatcca gggacagtga gtgtgcagct gttctggaag    1080
ccaacgcccc tgcaggaaga cagtggacag atccagggct acctgctgtc ctggaattcc    1140
ccagatcatc aagggcagga catacacctt tgcaacacca cgcagctcag ctgtatcttc    1200 ctcctgcct cagaggccca gaacgtgacc cttgtggcct acaacaaagc agggacctct    1260
tcacctacta cagtggtttt cctggagaac gaaggtccag ctgtgaccgg actccatgcc    1320
atggcccaag accttaacac catctgggta gactgggaag ccccagcct tctgcctcag    1380 ggctatctca ttgagtggga aatgagttct cccagctaca ataacagcta taagtcctgg    1440
atgatagaac ctaacgggaa catcactgga attctgttaa aggacaacat aaatcccttt    1500
cagctctaca gaattacagt ggctcccctg tacccaggca tcgtgggacc ccctgtaaat    1560

-continued

```
gtctacacct tcgctggaga gagagctcct cctcatgctc cagcgctgca tctaaagcat    1620
gttggcacaa cctgggcaca gctggagtgg gtacctgagg cccctaggct ggggatgata    1680
cccctcaccc actacaccat cttctgggcc gatgctgggg accactcctt ctccgtcacc    1740
ctaaacatct ccctccatga ctttgtcctg aagcacctgg agcccgccag tttgtatcat    1800
gtctacctca tggccaccag tcgagcaggg tccaccaata gtacaggcct taccctgagg    1860
accctagatc catctgactt aaacattttc ctgggcatac tttgcttagt actcttgtcc    1920
actacctgtg tagtgacctg gctctgctgc aaacgcagag gaaagacttc cttctggtca    1980
gatgtgccag acccagccca cagtagcctg agctcctggt tgcccaccat catgacagag    2040
gaaaccttcc agttacccag cttctgggac tccagcgtgc catcaatcac caagatcact    2100
gaactggagg aagacaagaa accgacccac tgggattccg aaagctctgg gaatggtagc    2160
cttccagccc tggttcaggc ctatgtgctc caaggagatc aagagaaat ttccaaccag    2220
tcccagcctc cctctcgcac tggtgaccag gtcctctatg gtcaggtgct tgagagcccc    2280
accagcccag gagtaatgca gtacattcgc tctgactcca ctcagcccct cttgggggc    2340
cccacccta gccctaaatc ttatgaaaac atctggttcc attcaagacc ccaggagacc    2400
tttgtgcccc aacctccaaa ccaggaagat gactgtgtct ttgggcctcc atttgatttt    2460
cccctctttc aggggctcca ggtccatgga gttgaagaac aagggggttt ctag        2514
```

<210> SEQ ID NO 84
<211> LENGTH: 837
<212> TYPE: PRT
<213> ORGANISM: Mus musculus

<400> SEQUENCE: 84

```
Met Val Gly Leu Gly Ala Cys Thr Leu Thr Gly Val Thr Leu Ile Phe
1               5                   10                  15

Leu Leu Leu Pro Arg Ser Leu Glu Ser Cys Gly His Ile Glu Ile Ser
            20                  25                  30

Pro Pro Val Val Arg Leu Gly Asp Pro Val Leu Ala Ser Cys Thr Ile
        35                  40                  45

Ser Pro Asn Cys Ser Lys Leu Asp Gln Gln Ala Lys Ile Leu Trp Arg
    50                  55                  60

Leu Gln Asp Glu Pro Ile Gln Pro Gly Asp Arg Gln His His Leu Pro
65                  70                  75                  80

Asp Gly Thr Gln Glu Ser Leu Ile Thr Leu Pro His Leu Asn Tyr Thr
                85                  90                  95

Gln Ala Phe Leu Phe Cys Leu Val Pro Trp Glu Asp Ser Val Gln Leu
            100                 105                 110

Leu Asp Gln Ala Glu Leu His Ala Gly Tyr Pro Ala Ser Pro Ser
        115                 120                 125

Asn Leu Ser Cys Leu Met His Leu Thr Thr Asn Ser Leu Val Cys Gln
    130                 135                 140

Trp Glu Pro Gly Pro Glu Thr His Leu Pro Thr Ser Phe Ile Leu Lys
145                 150                 155                 160

Ser Phe Arg Ser Arg Ala Asp Cys Gln Tyr Gln Gly Asp Thr Ile Pro
                165                 170                 175

Asp Cys Val Ala Lys Lys Arg Gln Asn Asn Cys Ser Ile Pro Arg Lys
            180                 185                 190

Asn Leu Leu Leu Tyr Gln Tyr Met Ala Ile Trp Val Gln Ala Glu Asn
        195                 200                 205
```

```
Met Leu Gly Ser Ser Glu Ser Pro Lys Leu Cys Leu Asp Pro Met Asp
    210                 215                 220
Val Val Lys Leu Glu Pro Pro Met Leu Gln Ala Leu Asp Ile Gly Pro
225                 230                 235                 240
Asp Val Val Ser His Gln Pro Gly Cys Leu Trp Leu Ser Trp Lys Pro
                245                 250                 255
Trp Lys Pro Ser Glu Tyr Met Glu Gln Glu Cys Glu Leu Arg Tyr Gln
            260                 265                 270
Pro Gln Leu Lys Gly Ala Asn Trp Thr Leu Val Phe His Leu Pro Ser
        275                 280                 285
Ser Lys Asp Gln Phe Glu Leu Cys Gly Leu His Gln Ala Pro Val Tyr
    290                 295                 300
Thr Leu Gln Met Arg Cys Ile Arg Ser Ser Leu Pro Gly Phe Trp Ser
305                 310                 315                 320
Pro Trp Ser Pro Gly Leu Gln Leu Arg Pro Thr Met Lys Ala Pro Thr
                325                 330                 335
Ile Arg Leu Asp Thr Trp Cys Gln Lys Lys Gln Leu Asp Pro Gly Thr
            340                 345                 350
Val Ser Val Gln Leu Phe Trp Lys Pro Thr Pro Leu Gln Glu Asp Ser
        355                 360                 365
Gly Gln Ile Gln Gly Tyr Leu Leu Ser Trp Asn Ser Pro Asp His Gln
    370                 375                 380
Gly Gln Asp Ile His Leu Cys Asn Thr Thr Gln Leu Ser Cys Ile Phe
385                 390                 395                 400
Leu Leu Pro Ser Glu Ala Gln Asn Val Thr Leu Val Ala Tyr Asn Lys
                405                 410                 415
Ala Gly Thr Ser Ser Pro Thr Thr Val Val Phe Leu Glu Asn Glu Gly
            420                 425                 430
Pro Ala Val Thr Gly Leu His Ala Met Ala Gln Asp Leu Asn Thr Ile
        435                 440                 445
Trp Val Asp Trp Glu Ala Pro Ser Leu Leu Pro Gln Gly Tyr Leu Ile
    450                 455                 460
Glu Trp Glu Met Ser Ser Pro Ser Tyr Asn Asn Ser Tyr Lys Ser Trp
465                 470                 475                 480
Met Ile Glu Pro Asn Gly Asn Ile Thr Gly Ile Leu Leu Lys Asp Asn
                485                 490                 495
Ile Asn Pro Phe Gln Leu Tyr Arg Ile Thr Val Ala Pro Leu Tyr Pro
            500                 505                 510
Gly Ile Val Gly Pro Pro Val Asn Val Tyr Thr Phe Ala Gly Glu Arg
        515                 520                 525
Ala Pro Pro His Ala Pro Ala Leu His Leu Lys His Val Gly Thr Thr
    530                 535                 540
Trp Ala Gln Leu Glu Trp Val Pro Glu Ala Pro Arg Leu Gly Met Ile
545                 550                 555                 560
Pro Leu Thr His Tyr Thr Ile Phe Trp Ala Asp Ala Gly Asp His Ser
                565                 570                 575
Phe Ser Val Thr Leu Asn Ile Ser Leu His Asp Phe Val Leu Lys His
            580                 585                 590
Leu Glu Pro Ala Ser Leu Tyr His Val Tyr Leu Met Ala Thr Ser Arg
        595                 600                 605
Ala Gly Ser Thr Asn Ser Thr Gly Leu Thr Leu Arg Thr Leu Asp Pro
    610                 615                 620
```

```
Ser Asp Leu Asn Ile Phe Leu Gly Ile Leu Cys Leu Val Leu Leu Ser
625                 630                 635                 640

Thr Thr Cys Val Val Thr Trp Leu Cys Cys Lys Arg Arg Gly Lys Thr
            645                 650                 655

Ser Phe Trp Ser Asp Val Pro Asp Pro Ala His Ser Ser Leu Ser Ser
        660                 665                 670

Trp Leu Pro Thr Ile Met Thr Glu Glu Thr Phe Gln Leu Pro Ser Phe
        675                 680                 685

Trp Asp Ser Ser Val Pro Ser Ile Thr Lys Ile Thr Glu Leu Glu Glu
    690                 695                 700

Asp Lys Lys Pro Thr His Trp Asp Ser Glu Ser Ser Gly Asn Gly Ser
705                 710                 715                 720

Leu Pro Ala Leu Val Gln Ala Tyr Val Leu Gln Gly Asp Pro Arg Glu
                725                 730                 735

Ile Ser Asn Gln Ser Gln Pro Pro Ser Arg Thr Gly Asp Gln Val Leu
            740                 745                 750

Tyr Gly Gln Val Leu Glu Ser Pro Thr Ser Pro Gly Val Met Gln Tyr
        755                 760                 765

Ile Arg Ser Asp Ser Thr Gln Pro Leu Leu Gly Gly Pro Thr Pro Ser
770                 775                 780

Pro Lys Ser Tyr Glu Asn Ile Trp Phe His Ser Arg Pro Gln Glu Thr
785                 790                 795                 800

Phe Val Pro Gln Pro Pro Asn Gln Glu Asp Asp Cys Val Phe Gly Pro
                805                 810                 815

Pro Phe Asp Phe Pro Leu Phe Gln Gly Leu Gln Val His Gly Val Glu
            820                 825                 830

Glu Gln Gly Gly Phe
        835

<210> SEQ ID NO 85
<211> LENGTH: 2583
<212> TYPE: DNA
<213> ORGANISM: Artificial
<220> FEATURE:
<223> OTHER INFORMATION: Chimera polypeptide

<400> SEQUENCE: 85
atgcgacctt ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca tttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caatgtggag    480
agcatccagt ggcgggacat agtcagcagt gactttctca gcaacatgtc gatggacttc    540
cagaaccacc tggcagctg ccaaaagtgt gatccaagct gtcccaatgg agctgctgg    600 ggtgcaggag aggagaactg ccagaaactg accaaaatca tctgtgccca gcagtgctcc    660
gggcgctgcc gtggcaagtc ccccagtgac tgctgcacaca accagtgtgc tgcaggctgc    720 acaggcccc gggagagcga ctgcctggtc tgccgcaaat tccgagacga agccacgtgc    780
aaggacacct gccccccact catgctctac aaccccacca cgtaccagat ggatgtgaac    840
```

-continued

```
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa accaaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggccccac tgcgtcaaga cctgcccggc aggagtcatg   1800
ggagaaaaca caccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccgatcc atctgactta aacatttcc tggagatcct ttgcttagta   1980
ctcttgtcca ctacctgtgt agtgacctgg ctctgctgca aacgcagagg aaagacttcc   2040
ttctggtcag atgtgccaga cccagcccac agtagcctga gctcctggtt gcccaccatc   2100
atgacagagg aaaccttcca gttacccagc ttctgggact ccagcgtgcc atcaatcacc   2160
aagatcactg aactggagga agacaagaaa ccgacccact gggattccga agctctggg   2220
aatggtagcc ttccagccct ggttcaggcc tatgtgctcc aaggagatcc aagagaaatt   2280
tccaaccagt cccagcctcc ctctcgcact ggtgaccagg tcctctatgg tcaggtgctt   2340
gagagcccca ccagcccagg agtaatgcag tacattcgct ctgactccac tcagcccctc   2400
ttggggggcc ccacccctag ccctaaatct tatgaaaaca tctggttcca ttcaagaccc   2460
caggagacct tgtgtcccca acctccaaac caggaagatg actgtgtctt tgggcctcca   2520
tttgattttc ccctctttca ggggctccag gtccatggag ttgaagaaca agggggtttc   2580
tag                                                                  2583
```

<210> SEQ ID NO 86
<211> LENGTH: 860
<212> TYPE: PRT
<213> ORGANISM: Artificial
<220> FEATURE:
<223> OTHER INFORMATION: Chimera polypeptide

<400> SEQUENCE: 86

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

-continued

```
Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460
```

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
        580                 585                 590

Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Asp Pro Ser Asp Leu Asn Ile Phe Leu Glu Ile
            645                 650                 655

Leu Cys Leu Val Leu Leu Ser Thr Thr Cys Val Val Thr Trp Leu Cys
        660                 665                 670

Cys Lys Arg Arg Gly Lys Thr Ser Phe Trp Ser Asp Val Pro Asp Pro
    675                 680                 685

Ala His Ser Ser Leu Ser Ser Trp Leu Pro Thr Ile Met Thr Glu Glu
690                 695                 700

Thr Phe Gln Leu Pro Ser Phe Trp Asp Ser Ser Val Pro Ser Ile Thr
705                 710                 715                 720

Lys Ile Thr Glu Leu Glu Glu Asp Lys Lys Pro Thr His Trp Asp Ser
            725                 730                 735

Glu Ser Ser Gly Asn Gly Ser Leu Pro Ala Leu Val Gln Ala Tyr Val
        740                 745                 750

Leu Gln Gly Asp Pro Arg Glu Ile Ser Asn Gln Ser Gln Pro Pro Ser
    755                 760                 765

Arg Thr Gly Asp Gln Val Leu Tyr Gly Gln Val Leu Glu Ser Pro Thr
770                 775                 780

Ser Pro Gly Val Met Gln Tyr Ile Arg Ser Asp Ser Thr Gln Pro Leu
785                 790                 795                 800

Leu Gly Gly Pro Thr Pro Ser Pro Lys Ser Tyr Glu Asn Ile Trp Phe
            805                 810                 815

His Ser Arg Pro Gln Glu Thr Phe Val Pro Gln Pro Asn Gln Glu
        820                 825                 830

Asp Asp Cys Val Phe Gly Pro Phe Asp Phe Pro Leu Phe Gln Gly
    835                 840                 845

Leu Gln Val His Gly Val Glu Glu Gln Gly Gly Phe
850                 855                 860

<210> SEQ ID NO 87
<211> LENGTH: 23
<212> TYPE: DNA

```
<213> ORGANISM: Artificial
<220> FEATURE:
<223> OTHER INFORMATION: PCR primer

<400> SEQUENCE: 87
gctcactgga tggtgggaag atg                                          23

<210> SEQ ID NO 88
<211> LENGTH: 21
<212> TYPE: DNA
<213> ORGANISM: Artificial
<220> FEATURE:
<223> OTHER INFORMATION: PCR primer

<400> SEQUENCE: 88
gggccagtgg atagacagat g                                            21

<210> SEQ ID NO 89
<211> LENGTH: 24
<212> TYPE: DNA
<213> ORGANISM: Artificial
<220> FEATURE:
<223> OTHER INFORMATION: PCR primer

<400> SEQUENCE: 89
caggggccag tggatagacc gatg                                         24

<210> SEQ ID NO 90
<211> LENGTH: 31
<212> TYPE: DNA
<213> ORGANISM: Artificial
<220> FEATURE:
<223> OTHER INFORMATION: PCR primer

<400> SEQUENCE: 90
gttaagcttc caccatgcga ccctccggga c                                 31

<210> SEQ ID NO 91
<211> LENGTH: 35
<212> TYPE: DNA
<213> ORGANISM: Artificial
<220> FEATURE:
<223> OTHER INFORMATION: PCR primer

<400> SEQUENCE: 91
gttggtgacc gacgggatct taggcccatt cgttg                             35

<210> SEQ ID NO 92
<211> LENGTH: 1146
<212> TYPE: DNA
<213> ORGANISM: Artificial
<220> FEATURE:
<223> OTHER INFORMATION: Chimera polypeptide

<400> SEQUENCE: 92
atgaagctgc tgccgtcggt ggtgctgaag ctctttctgg ctgcagttct ctcggcactg    60
gtgactggcg agagcctgga gcggcttcgg agagggctag ctgctggaac cagcaacccg   120
gaccctccca ctgtatccac ggaccagctg tacccctag gaggcggccg ggaccggaaa    180
gtccgtgact tgcaagaggc agatctggac cttttgagag tcactttatc ctccaagcca   240
caagcactgg ccacaccaaa caaggaggag cacgggaaaa gaagaagaa aggcaagggg    300 ctagggaaga agaggaccc atgtcttcgg aaatacaagg acttctgcat ccatggagaa    360
tgcaaatatg tgaaggagct ccgggctccc tcctgcatct gccaccgggg ttaccatgga   420
```

-continued

```
gagaggtgtc atgggctgag cctcgaacct cgcggaccga caatcaagcc ctgtcctcca    480
tgcaaatgcc agcacctaa cctcttgggt ggaccatccg tcttcatctt ccctccaaag    540
atcaaggatg tactcatgat ctccctgagc cccatagtca catgtgtggt ggtggatgtg    600
agcgaggatg acccagatgt ccagatcagc tggtttgtga acaacgtgga agtacacaca    660
gctcagacac aaaccccatag agaggattac aacagtactc tccgggtggt cagtgccctc    720
cccatccagc accaggactg gatgagtggc aaggagttca atgcaaggt caacaacaaa    780
gacctgccag cgcccatcga gagaaccatc tcaaaaccca aagggtcagt aagagctcca    840
caggtatatg tcttgcctcc accagaagaa gagatgacta agaaacaggt cactctgacc    900
tgcatggtca cagacttcat gcctgaagac atttacgtgg agtggaccaa caacgggaaa    960
acagagctaa actacaagaa cactgaacca gtcctggact ctgatggttc ttacttcatg   1020
tacagcaagc tgagagtgga aaagaagaac tgggtggaaa gaaatagcta ctcctgttca   1080
gtggtccacg agggtctgca caatcaccac acgactaaga gcttctcccg gactccgggt   1140
aaatga                                                              1146
```

<210> SEQ ID NO 93
<211> LENGTH: 381
<212> TYPE: PRT
<213> ORGANISM: Artificial
<220> FEATURE:
<223> OTHER INFORMATION: Chimera polypeptide

<400> SEQUENCE: 93

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Glu Pro Arg Gly Pro Thr Ile Lys Pro Cys Pro Pro
145                 150                 155                 160

Cys Lys Cys Pro Ala Pro Asn Leu Leu Gly Gly Pro Ser Val Phe Ile
                165                 170                 175

Phe Pro Pro Lys Ile Lys Asp Val Leu Met Ile Ser Leu Ser Pro Ile
            180                 185                 190

Val Thr Cys Val Val Val Asp Val Ser Glu Asp Asp Pro Asp Val Gln
        195                 200                 205

Ile Ser Trp Phe Val Asn Asn Val Glu Val His Thr Ala Gln Thr Gln
    210                 215                 220
```

```
Thr His Arg Glu Asp Tyr Asn Ser Thr Leu Arg Val Val Ser Ala Leu
225                 230                 235                 240

Pro Ile Gln His Gln Asp Trp Met Ser Gly Lys Glu Phe Lys Cys Lys
                245                 250                 255

Val Asn Asn Lys Asp Leu Pro Ala Pro Ile Glu Arg Thr Ile Ser Lys
            260                 265                 270

Pro Lys Gly Ser Val Arg Ala Pro Gln Val Tyr Val Leu Pro Pro Pro
        275                 280                 285

Glu Glu Glu Met Thr Lys Lys Gln Val Thr Leu Thr Cys Met Val Thr
    290                 295                 300

Asp Phe Met Pro Glu Asp Ile Tyr Val Glu Trp Thr Asn Asn Gly Lys
305                 310                 315                 320

Thr Glu Leu Asn Tyr Lys Asn Thr Glu Pro Val Leu Asp Ser Asp Gly
                325                 330                 335

Ser Tyr Phe Met Tyr Ser Lys Leu Arg Val Glu Lys Lys Asn Trp Val
                340                 345                 350

Glu Arg Asn Ser Tyr Ser Cys Ser Val Val His Glu Gly Leu His Asn
            355                 360                 365

His His Thr Thr Lys Ser Phe Ser Arg Thr Pro Gly Lys
    370                 375                 380
```

ANTI-CANCER AGENT COMPRISING ANTI-HB-EGF ANTIBODY AS ACTIVE INGREDIENT

This is a national phase of International Application No. PCT/JP2007/070466, filed Oct. 19, 2007, which claims priority to Japanese Application No. 2006-286824, filed Oct. 20, 2006, the disclosures of which are all hereby incorporated by reference herein.

TECHNICAL FIELD

The present invention relates to a method of treating cancer and to an anti-cancer agent.

BACKGROUND

Heparin-binding epidermal growth factor-like growth factor, or HB-EGF, is a growth factor belonging to the EGF ligand family. HB-EGF gene-null knockout mice exhibit very detrimental phenotypes, such as cardiac function failure accompanied by cardiohypertrophy, and quickly die after birth (Nonpatent Reference 1). This shows that HB-EGF makes a profound contribution to the formation of the heart during gestation. In the adult, on the other hand, its expression is distributed across a relatively broad range of tissues, e.g., the lung, heart, brain, and skeletal muscle (Nonpatent Reference 2), and HB-EGF has a very important role not just during gestation, but also in maintaining biological function in the adult (Nonpatent Reference 3).

HB-EGF occurs as two different structures in vivo: a membrane-bound HB-EGF that is expressed on the cell surface of HB-EGF-expressing cells (designated below as proHB-EGF) and a secreted-form HB-EGF that occurs free from the cell (designated below as sHB-EGF or active-form HB-EGF). The structures of proHB-EGF and sHB-EGF are shown schematically in FIG. 1. The proHB-EGF precursor protein is composed of 208 amino acids and is composed, considered from the N-terminal, of a signal peptide, propeptide, heparin-binding domain, EGF-like domain, juxtamembrane domain, transmembrane domain, and cytoplasmic domain. Cleavage of the signal peptide from the proHB-EGF precursor protein results in the expression of proHB-EGF as a type 1 transmembrane protein. Subsequently, proHB-EGF is subjected to protease digestion, known as ectodomain shedding, and sHB-EGF, composed of 73 to 87 amino acid residues, is released into the extracellular environment. This sHB-EGF is composed of just two domains, the heparin-binding domain and the EGF-like domain, and binds as an active ligand to the EGF receptor (Her1) and EGF receptor 4 (Her4). This results in the induction of proliferation, via the downstream ERK/MAPK signaling pathway, in a variety of cells, e.g., NIH3T3 cells, smooth muscle cells, epithelial cells, keratinocytes, renal tubule cells, and so forth (Nonpatent Reference 4). A substantial reduction in proliferation ability occurs with cells that express only proHB-EGF due to the introduction of mutation into the region that participates in ectodomain shedding. In addition, transgenic mice that express only proHB-EGF have the same phenotype as HB-EGF knockout mice. Based on these observations, the function of HB-EGF as a growth factor is thought to be borne mainly by the secreted form of HB-EGF (Nonpatent References 5 and 6).

proHB-EGF, on the other hand, is also known to have a unique function in vivo different from that of sHB-EGF. That is, proHB-EGF was initially known to function as a receptor for the diphtheria toxin (DT) (Nonpatent References 7 and 8). However, subsequent research demonstrated that proHB-EGF forms complexes at the cell surface with molecules such as DRAP27/CD9 and also integrin $\alpha_3\beta_1$ and heparin sulfate and participates in cell adhesion and migration. Operating through the EGF receptor (designated hereafter as EGFR) via a juxtacrine mechanism, proHB-EGF has also been shown to inhibit the growth of neighboring cells and to induce neighboring cell death. Thus, with regard to HB-EGF in its role as a ligand for EGFR, the membrane-bound proHB-EGF and secreted-form sHB-EGF are known to transmit diametrically opposite signals (Nonpatent References 5 and 8).

HB-EGF has a strong promoting activity on cell proliferation, cell movement, and infiltration in a variety of cell lines, for example, cancer cells. In addition, an increase in HB-EGF expression over that in normal tissue has been reported for a broad range of cancer types (e.g., pancreatic cancer, liver cancer, esophageal cancer, melanoma, colorectal cancer, gastric cancer, ovarian cancer, bladder cancer, and brain tumors), suggesting that HB-EGF is strongly implicated in cancer proliferation or malignant transformation (Nonpatent References 4 and 10).

Based on these findings, the inhibition of cancer cell growth via an inhibition of HB-EGF activity has therefore been pursued. The following effects, inter alia, have been reported for efforts to inhibit the action of HB-EGF using anti-HB-EGF neutralizing antibodies: an inhibition of DNA synthesis in 3T3 cells (Nonpatent Reference 11), an inhibition of keratinocyte growth (Nonpatent Reference 12), an inhibition of glioma cell growth (Nonpatent Reference 13), and an inhibition of DNA synthesis in myeloma cells (Nonpatent Reference 14).

The use of an attenuated diphtheria toxin (CRM197) that specifically binds to HB-EGF as an HB-EGF inhibitor has also been pursued. In fact, in a test of the efficacy in a mouse xenograft model (transplantation of an ovarian cancer cell line), the group receiving CRM197 presented a superior tumor shrinkage effect (Nonpatent Reference 15). In addition, clinical testing with CRM197 has also been carried out in cancer patients (Nonpatent Reference 6).

Thus, HB-EGF is clearly useful as a target molecule for anti-cancer agents, and the efficacy of HB-EGF inhibitor molecules such as CRM197 have in fact also been tested to date. However, CRM197 is a toxin not naturally present in the human body, and it is therefore thought that the clinical utilization of CRM197 will be encumbered by very substantial problems arising not just from its toxicity, but also from its antigenicity.

In addition, although neutralizing antibodies that can inhibit the activity of HB-EGF have in fact existed for some time as noted above, all of these have been polyclonal antibodies purified from goat antisera and hence cannot be used clinically. Thus, there is demand in the medical community for HB-EGF-neutralizing monoclonal antibodies that can exhibit a high neutralizing activity and that can realize the humanization and high production levels required for clinical applications.

However, when contemplating the clinical application of anti-HB-EGF neutralizing antibodies, toxicity such as antibody-dependent cell-mediated cytotoxicity (abbreviated below as ADCC activity) mediated by the antibody and effector cells and complement-dependent cytotoxicity (abbreviated below as CDC) is a risk due to the fact that, as cited above, HB-EGF is also expressed in vivo in a broad range of normal tissues in the form of proHB-EGF, which is the HB-EGF protein on the cell surface of HB-EGF-expressing cells. Other problems that must be addressed are the reduction in the efficiency of antibody accumulation at the tumor tissue and the reduction in blood concentration brought about by uptake of the antibody in normal tissues.

The references cited in this specification is listed below. The contents of these documents are herein incorporated by reference in their entirety. None of these documents is admitted as prior art to the present invention:

Nonpatent Reference 1: Iwamoto R, Yamazaki S, Asakura M et al., Heparin-binding EGF-like growth factor and ErbB signaling is essential for heart function. *Proc. Natl. Acad. Sci. USA,* 2003; 100:3221-6.

Nonpatent Reference 2: Abraham J A, Damm D, Bajardi A, Miller J, Klagsbrun M, Ezekowitz R A. Heparin-binding EGF-like growth factor: characterization of rat and mouse cDNA clones, protein domain conservation across species, and transcript expression in tissues. *Biochem Biophys Res Commun,* 1993; 190:125-33.

Nonpatent Reference 3: Karen M. *Frontiers in Bioscience,* 3, 288-299, 1998.

Nonpatent Reference 4: Raab G, Klagsbrun M. Heparin-binding EGF-like growth factor. *Biochim Biophys Acta,* 1997; 1333:F179-99.

Nonpatent Reference 5: Yamazaki S, Iwamoto R, Saeki K et al. Mice with defects in HB-EGF ectodomain shedding show severe developmental abnormalities. *J Cell Biol,* 2003; 163: 469-75.

Nonpatent Reference 6: Ongusaha P. *Cancer Res.,* (2004) 64, 5283-5290.

Nonpatent Reference 7: Iwamoto R, Higashiyama S. *EMBO J.,* 13, 2322-2330 (1994).

Nonpatent Reference 8: Naglich J G, Metherall J E. *Cell,* 69, 1051-1061 (1992).

Nonpatent Reference 9: Iwamoto R, Handa K, Mekada E. Contact-dependent growth inhibition and apoptosis of epidermal growth factor (EGF) receptor-expressing cells by the membrane-anchored form of heparin-binding EGF-like growth factor. *J Biol Chem,* 1999; 274:25906-12.

Nonpatent Reference 10: Miyamoto S, *Cancer Sci.,* 97, 341-347 (2006).

Nonpatent Reference 11: Blotnick S. *Proc. Natl. Acad. Sci. USA,* (1994) 91, 2890-2894.

Nonpatent Reference 12: Hashimoto K. *J Biol Chem*, (1994) 269, 20060-20066.

Nonpatent Reference 13: Mishima K. *Act Neuropathol.,* (1998) 96, 322-328.

Nonpatent Reference 14: Wang Y D. *Oncogene,* (2002) 21, 2584-2592.

Nonpatent Reference 15: Miyamoto S. *Cancer Res.,* (2004) 64, 5720-

Nonpatent Reference 16: Buzzi S. *Cancer Immunol Immunother,* (2004) 53, 1041-1048.

DISCLOSURE OF THE INVENTION

An object of the present invention is to provide anti-HB-EGF antibody and applications thereof. A more particular object is to provide a novel method for treating cancer using an anti-HB-EGF antibody, a novel cell proliferation inhibitor that comprises an anti-HB-EGF antibody, a novel anti-cancer agent that comprises an anti-HB-EGF antibody, as well as a novel anti-HB-EGF antibody.

The present inventors have discovered that antibody that exhibits a neutralizing activity on HB-EGF, which is strongly expressed in cancer cells, can significantly inhibit the growth capability of cancer cells. They also discovered that antibody that has the neutralizing activity does not bind to the HB-EGF protein on the cell surface of HB-EGF-expressing cells. Based on this finding, the present inventors have further discovered that anti-HB-EGF antibody is effective for the treatment of cancers in which HB-EGF expression is upregulated, the most prominent example being ovarian cancer. The present invention was achieved based on these discoveries.

The present inventors immunized mice with HB-EGF protein and obtained monoclonal antibodies that inhibit the HB-EGF-mediated induction of cell growth, which have heretofore been no reports. Moreover, the present inventors determined that the obtained neutralizing antibodies did not bind to the proHB-EGF that is the HB-EGF protein on the cell surface of HB-EGF-expressing cells, but rather had an ability to bind only to secreted-form HB-EGF (sHB-EGF), which is present free from the HB-EGF-expressing cell. The special properties of the antibody according to the present invention solved the prior problems that had to be addressed, i.e., antibody-mediated toxicity, e.g., ADCC activity and CDC activity, and the reduction in the blood concentration and tumor accumulation rate.

Thus, the present application provides monoclonal antibody and lower molecular weight antibody derivatives selected from the following (1) to (29).

(1) an antibody comprising a heavy chain variable region having the amino acid sequence of SEQ ID NO: 2 as CDR1, the amino acid sequence of SEQ ID NO: 4 as CDR2, and the amino acid sequence of SEQ ID NO: 6 as CDR3;

(2) an antibody comprising the heavy chain variable region according to (1) that has the amino acid sequence of SEQ ID NO: 8 as CH;

(3) an antibody comprising the heavy chain variable region according to (1) that has the amino acid sequence of SEQ ID NO: 10 as CH;

(4) an antibody comprising a light chain variable region having the amino acid sequence of SEQ ID NO: 12 as CDR1, the amino acid sequence of SEQ ID NO: 14 as CDR2, and the amino acid sequence of SEQ ID NO: 16 as CDR3;

(5) an antibody comprising the light chain variable region according to (4) that has the amino acid sequence of SEQ ID NO: 18 as CL;

(6) an antibody comprising the light chain variable region according to (4) that has the amino acid sequence of SEQ ID NO: 20 as CL;

(7) an antibody comprising the heavy chain according to (1) and the light chain according to (4);

(8) an antibody comprising the heavy chain according to (2) and the light chain according to (5);

(9) an antibody comprising the heavy chain according to (3) and the light chain according to (6);

(10) an antibody comprising a heavy chain variable region having the amino acid sequence of SEQ ID NO: 22 as CDR1, the amino acid sequence of SEQ ID NO: 24 as CDR2, and the amino acid sequence of SEQ ID NO: 26 as CDR3;

(11) an antibody comprising a heavy chain variable region according to (10) that has the amino acid sequence of SEQ ID NO: 28 as CH;

(12) an antibody comprising the heavy chain variable region according to (10) that has the amino acid sequence of SEQ ID NO: 10 as CH;

(13) an antibody comprising a light chain variable region having the amino acid sequence of SEQ ID NO: 30 as CDR1, the amino acid sequence of SEQ ID NO: 32 as CDR2, and the amino acid sequence of SEQ ID NO: 34 as CDR3;

(14) an antibody comprising the light chain variable region according to (13) that has the amino acid sequence of SEQ ID NO: 18 as CL;

(15) an antibody comprising the light chain variable region according to (13) that has the amino acid sequence of SEQ ID NO: 20 as CL;
(16) an antibody comprising the heavy chain according to (10) and the light chain according to (13);
(17) an antibody comprising the heavy chain according to (11) and the light chain according to (14);
(18) an antibody comprising the heavy chain according to (12) and the light chain according to (15);
(19) an antibody comprising a heavy chain variable region having the amino acid sequence of SEQ ID NO: 36 as CDR1, the amino acid sequence of SEQ ID NO: 38 as CDR2, and the amino acid sequence of SEQ ID NO: 40 as CDR3;
(20) an antibody comprising the heavy chain variable region according to (19) that has the amino acid sequence of SEQ ID NO: 28 as CH;
(21) an antibody comprising the heavy chain variable region according to (19) that has the amino acid sequence of SEQ ID NO: 10 as CH;
(22) an antibody comprising a light chain variable region having the amino acid sequence of SEQ ID NO: 42 as CDR1, the amino acid sequence of SEQ ID NO: 44 as CDR2, and the amino acid sequence of SEQ ID NO: 46 as CDR3;
(23) an antibody comprising the light chain variable region according to (22) that has the amino acid sequence of SEQ ID NO: 18 as CL;
(24) an antibody comprising the light chain variable region according to (22) that has the amino acid sequence of SEQ ID NO: 20 as CL;
(25) an antibody comprising the heavy chain according to (19) and the light chain according to (22);
(26) an antibody comprising the heavy chain according to (20) and the light chain according to (23);
(27) an antibody comprising the heavy chain according to (21) and the light chain according to (24);
(28) an antibody obtained by the substitution of one or a plurality of amino acids in, deletion of one or a plurality of amino acids from, addition of one or a plurality of, amino acids to, and/or insertion of one or a plurality of amino acids into the antibody according to any of (1) to (27) and having the activity equivalent to that of the antibody according to any of (1) to (27); and
(29) an antibody that binds to an epitope that is the same as the epitope of HB-EGF protein that is bound by the antibody according to any of (1) to (27).

The present invention additionally provides monoclonal antibody according to the preceding (1) to (29) that does not bind to the HB-EGF protein on the cell surface of cells that express HB-EGF having SEQ ID NO: 59. More particularly, the present invention provides monoclonal antibody according to the preceding (1) to (29), wherein the antibody does not bind to cells that express HB-EGF having SEQ ID NO: 59 said cells being selected from RMG-1, and any of Ba/F3, DG44, or SKOV-3 that recombinantly expresses HB-EGF having SEQ ID NO: 59.

The present invention further provides an anti-cancer agent that comprises, as an active ingredient, an antibody that binds to HB-EGF protein. The HB-EGF protein-binding antibody is preferably an antibody that exhibits a neutralizing activity. The neutralizing antibody is more preferably an antibody that does not bind to cells that express HB-EGF. The cancer is preferably pancreatic cancer, liver cancer, esophageal cancer, melanoma, colorectal cancer, gastric cancer, ovarian cancer, bladder cancer, or a brain tumor. Ovarian cancer is particularly preferred.

In another aspect, the present invention provides a method of inhibiting the proliferation of cells that express HB-EGF protein by bringing cells that express HB-EGF into contact with antibody that binds to HB-EGF protein. The antibody that binds to HB-EGF protein is preferably antibody that exhibits a neutralizing activity. The cells that express HB-EGF protein are preferably cancer cells.

The HB-EGF protein-specific antibody according to the present invention can be employed as a cytotoxic agent or cell proliferation inhibitor not only for ovarian cancer, which expresses HB-EGF protein, but also for a variety of HB-EGF protein-expressing cancer cells, such as pancreatic cancer cells, liver cancer cells, esophageal cancer cells, melanoma cells, colorectal cancer cells, gastric cancer cells, bladder cancer cells, and brain tumor cells.

The cytotoxic anti-HB-EGF antibody of the present invention can also be employed as a therapeutic agent against a variety of cancers, e.g., ovarian cancer, pancreatic cancer, liver cancer, esophageal cancer, melanoma, colorectal cancer, gastric cancer, bladder cancer, and brain tumors.

A gene coding for the antibody according to the present invention and a recombinant cell transformed by such a gene can be used to produce a recombinant antibody that achieves the aforementioned effects or even better effects.

BRIEF DESCRIPTION OF THE DRAWINGS

FIGS. 4a and 4b are comparisons of the variable region sequences of HB-EGF neutralizing antibodies;

PREFERRED EMBODIMENT OF THE INVENTION

The Molecular Forms of HB-EGF

Figure 1:
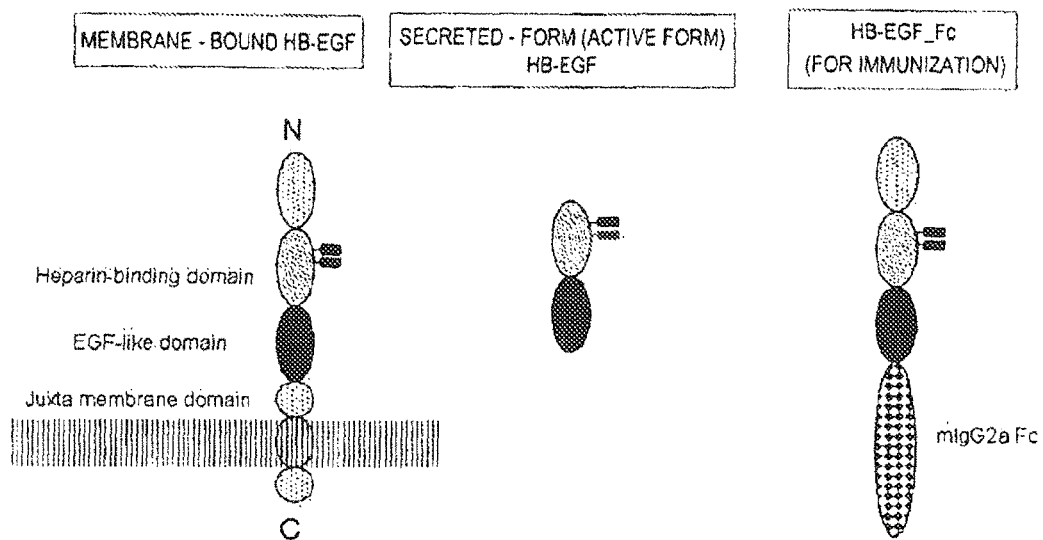
FIG. 1 is a diagram that schematically depicts the structure of proHB-EGF, sHB-EGF, and the HB-EGF_Fc used as immunogen.

HB-EGF is a growth factor that belongs to the EGF ligand family; the sequence of the gene encoding human HB-EGF is disclosed as GenBank accession number NM_001945 (SEQ ID NO: 59) and the amino acid sequence of HB-EGF is disclosed as GenBank accession number NP_001936 (SEQ ID NO: 60). Within the context of the present invention, "HB-EGF protein" is a term that encompasses both the full-length protein and fragments thereof. Within the context of the present invention, a "fragment" is a polypeptide that contains any region of the HB-EGF protein, wherein the fragment may not exhibit the functionality of the naturally occurring HB-EGF protein. sHB-EGF, which is used herein as a specific embodiment of a fragment, is a molecule composed of 73 to 87 amino acid residues and is produced in vivo when the proHB-EGF expressed on the cell surface of an HB-EGF-expressing cell is subjected to protease cleavage in a process known as ectodomain shedding.

Multiple sHB-EGF molecules are known; these sHB-EGF molecules have a structure in which the carboxyl terminal is the proline residue at position 149 in the proHB-EGF molecule (the proHB-EGF molecule is composed of the 208 amino acids shown in SEQ ID NO: 60) while the amino terminal is the asparagine residue at position 63 of the proHB-EGF molecule, the arginine residue at position 73 of the proHB-EGF molecule, the valine residue at position 74 of the proHB-EGF molecule, or the serine residue at position 77 of the proHB-EGF molecule.

Production of the Anti-HB-EGF Antibody

The anti-HB-EGF antibody of the present invention is monoclonal antibody that specifically binds to HB-EGF protein, but there are no limitations with regard to its origin, type, or configuration. In specific terms, monoclonal antibody of nonhuman origin (for example, mouse antibody, rat antibody, camel antibody) can be used, as can human antibodies, chimeric antibodies, and humanized antibodies obtained by genetic engineering techniques.

Monoclonal anti-HB-EGF antibody according to the present invention can be obtained using known means. Monoclonal antibody of mammalian origin is particularly preferred for the anti-HB-EGF antibody of the present invention. The monoclonal antibody of mammalian origin encompasses, inter alia, monoclonal antibody produced by a hybridoma and monoclonal antibody produced by a host that has been transformed by genetic engineering techniques with an expression vector that comprises the antibody gene.

Monoclonal antibody-producing hybridomas substantially can be produced using known technology and production can proceed as follows. First an animal is immunized with HB-EGF protein as the sensitizing antigen according to the usual immunization methods. Immune cells obtained from the immunized animal are fused with a known partner cell by the usual cell fusion techniques to obtain hybridomas. Using the usual screening techniques, these hybridomas can be subjected to the selection of hybridomas that produce anti-HB-EGF antibody by screening for cells that produce the desired antibody.

In specific terms, monoclonal antibody production can be carried out, for example, as follows. First, the HB-EGF protein used as the sensitizing antigen for antibody acquisition can be obtained by the expression of an HB-EGF gene. The base sequence of the human HB-EGF gene is disclosed, for example, as GenBank accession number NM_001945 (SEQ ID NO: 59). Thus, the gene sequence encoding HB-EGF is inserted into a known expression vector and a suitable host cell is then transformed with the expression vector; the desired human HB-EGF protein can subsequently be purified from within the host cells or from the culture supernatant. Purified natural HB-EGF protein can also be used in the same manner. The protein may be purified using one or a combination of the usual chromatographic techniques, e.g., ion chromatography, affinity chromatography, and so forth, using a single run or a plurality of runs. The immunogen used in the present invention can also be a fusion protein as obtained by fusion of a desired partial polypeptide from the HB-EGF protein with a different polypeptide. For example, a peptide tag or the Fc fragment from the antibody can be used to produce the fusion protein that will be used as the immunogen. A vector that expresses the fusion protein can be prepared by in-frame fusion of the genes encoding the desired two or more polypeptide fragments and insertion of the fused gene into an expression vector as described above. Methods for producing fusion proteins are described in *Molecular Cloning 2nd Edition* (Sambrook, J. et al., *Molecular Cloning 2nd Edition*, 9.47-9.58, Cold Spring Harbor Laboratory Press, 1989).

The HB-EGF protein purified in the described manner can be employed as the sensitizing antigen used to immunize a mammal. A partial peptide from HB-EGF can also be used as the sensitizing antigen. For example, the following peptides can be used as the sensitizing antigen: peptide obtained from the amino acid sequence for human HB-EGF by chemical synthesis; peptide obtained by incorporating a portion of the human HB-EGF gene into an expression vector and expressing same; and peptide obtained by degradation of human HB-EGF protein with a protein degrading enzyme.

There are no limitations on the HB-EGF region used as the partial peptide or on the size of the partial peptide. A preferred region can be selected from the amino acid sequence constituting the extracellular domain of HB-EGF (positions 22 to 149 in the amino acid sequence of SEQ ID NO: 60). The number of amino acids making up the peptide that will be used as the sensitizing antigen is preferably at least 3, for example, at least 5 or at least 6. More specifically, a peptide of 8 to 50 residues and preferably 10 to 30 residues can be used as the sensitizing antigen.

There are no particular limitations on the mammal that may be immunized by the sensitizing antigen described above. In order to obtain monoclonal antibody by cell fusion techniques, the immunized animal is preferably selected considering the compatibility with the partner cell that will be used in cell fusion. Rodents are generally preferred as the immunized animal. Specifically, the mouse, rat, hamster, or rabbit can be used as the immunized animal. Monkeys can also be used as the immunized animal.

The animal as described above can be immunized with the sensitizing antigen according to known methods. For example, as a general method, the mammal can be immunized by subcutaneous or intraperitoneal injection of the sensitizing antigen. In specific terms, the sensitizing antigen may be administered to the mammal a plurality times on a 4 to 21 day schedule. The sensitizing antigen is used diluted to a suitable dilution factor with, for example, phosphate buffered saline (PBS) or physiological saline. The sensitizing antigen may also be administered in combination with an adjuvant. For example, the sensitizing antigen can be prepared by mixing and emulsification with Freund's complete adjuvant. A suitable carrier can also be used in immunization with the sensitizing antigen. Particularly in those instances in which a low molecular weight partial peptide is used as the sensitizing antigen, immunization is desirably effected with the sensitizing peptide antigen conjugated with a protein carrier, e.g., albumin, keyhole limpet hemocyanin, and so forth.

After the mammal is immunized in the described manner and a desired rise in the serum antibody titer is observed, immune cells are collected from the mammal and are submitted to cell fusion. Splenocytes in particular are preferred immune cells.

Mammalian myeloma cells are used as the cells for fusion with the above-described immune cells. The myeloma cells are preferably provided with a suitable selection marker to support screening. The selection marker denotes a trait that can appear (or that cannot appear) under specific culture conditions. Known selection markers include hypoxanthine-guanine phosphoribosyltransferase deficiency (abbreviated below as HGPRT deficiency) and thymidine kinase deficiency (abbreviated below as TK deficiency). Cells that are HGPRT- or TK-deficient exhibit hypoxanthine-aminopterin-thymidine sensitivity (abbreviated below as HAT sensitivity). HAT-sensitive cells are unable to undergo DNA synthesis on an HAT selection medium and die; however, when fused with a normal cell, DNA synthesis can continue using the salvage pathway of the normal cell and growth can also occur on HAT selection medium.

HGPRT-deficient cells can be selected on a medium containing 6-thioguanine or 8-azaguanine (8AG), while TK-deficient cells can be selected on a medium containing 5'-bromodeoxyuridine. Normal cells incorporate these pyrimidine analogues into their DNA and die, while cells deficient in these enzymes do not incorporate these pyrimidine analogs and are able to survive on the selection medium. Another selection marker, known as G418 resistance, imparts resistance to 2-deoxystreptamine-type antibiotics (gentamycin analogues) based on the neomycin resistance gene. Various myeloma cells suitable for cell fusion are known. For example, the following myeloma cells can be employed to produce monoclonal antibody in the present invention:

P3 (P3x63Ag8.653) (*J. Immunol.* (1979) 123, 1548-1550),
P3x63Ag8U.1 (*Current Topics in Microbiology and Immunology* (1978) 81, 1-7),
NS-1 (Kohler, G. and Milstein, C. *Eur. J. Immunol.* (1976) 6, 511-519),
MPC-11 (Margulies, D. H. et al., *Cell* (1976) 8, 405-415),
SP2/0 (Shulman, M. et al., *Nature* (1978) 276, 269-270),
FO (de St. Groth, S. F. et al., *J. Immunol. Methods* (1980) 35, 1-21),
S194 (Trowbridge, I. S. *J. Exp. Med.* (1978) 148, 313-323), and
R210 (Galfre, G. et al., *Nature* (1979) 277, 131-133).

Cell fusion between the above-described immune cells and myeloma cells can be carried out according to known methods, for example, according to the method of Kohler and Milstein (Kohler, G. and Milstein, C., *Methods Enzymol.* (1981) 73, 3-46).

More specifically, cell fusion can be carried out, for example, in the usual nutrient culture fluids in the presence of a cell fusion promoter. For example, polyethylene glycol (PEG) or Sendai virus (HVJ) can be used as the fusion promoter. As desired, an auxiliary such as dimethyl sulfoxide can be added in order to boost the fusion efficiency.

The ratio between the immune cells and the myeloma cells can be freely selected. For example, the immune cells are preferably used at 1 to 10 times with respect to the myeloma cells. The culture fluid used for cell fusion can be, for example, RPMI1640 culture medium or MEM culture medium, which are very suitable for the growth of the previously cited myeloma cell lines, or can be the usual culture media used for this type of cell culture. A serum supplement such as fetal calf serum (FCS) can also be added to the culture medium.

The desired fused cells (hybridomas) are formed by cell fusion by thoroughly mixing prescribed quantities of the immune cells and myeloma cells in a culture fluid as described above and admixing a PEG solution that has been preheated to about 37° C. For example, PEG with an average molecular weight of 1000 to 6000 can be added to the cell fusion process at a concentration generally from 30 to 60% (w/v). Then, the cell fusion agents and so forth that are undesirable for hybridoma growth are removed by repeating the process of adding a suitable culture fluid as described above, centrifuging, and removing the supernatant.

The hybridomas obtained in the described manner can be selected by using a selection medium adapted to the selection markers exhibited by the myeloma used for cell fusion. For example, HGPRT- or TK-deficient cells can be selected by culture on HAT medium (medium containing hypoxanthine, aminopterin, and thymidine). Thus, when HAT-sensitive myeloma cells are used for cell fusion, cells resulting from cell fusion with the normal cells can selectively grow on the HAT medium. Culture on the HAT medium is continued for a period of time sufficient for cells (unfused cells) other than the desired hybridomas to die. In specific terms, the desired hybridomas can be selected generally by culture for from several days to several weeks. The usual limit dilution process can be used for screening and monocloning of hybridomas that produce the desired antibody. Or, antibody that recognizes HB-EGF can also be produced by the method described in WO 03/104453.

Screening for and monocloning the desired antibody can be suitably carried out by a screening procedure based on known antigen-antibody reactions. For example, an antigen may be bound to a carrier (e.g., beads of, for example, polystyrene, or a commercial 96-well microtiter plate) and then reacted with hybridoma culture supernatant. Then, after the carrier has been washed, the cells are reacted with, for example, an enzyme-labeled secondary antibody. If the desired sensitizing antigen-reactive antibody was present in the culture supernatant, the secondary antibody will bind to the carrier through the antibody. The presence/absence of the desired antibody in the culture supernatant can finally be established by detection of the secondary antibody that is bound to the carrier. A hybridoma that produces the desired antigen-binding antibody can be cloned, for example, by the limit dilution method. Here, substantially the same HB-EGF protein is suitably used as the antigen, most prominently the HB-EGF protein used for immunization. For example, an oligopeptide comprising the extracellular domain of HB-EGF—or comprising a partial amino acid sequence from that region—can be used as the antigen.

In addition to the above-described method of producing a hybridoma by immunizing a nonhuman animal with antigen, the desired antibody can also be obtained by the antigenic sensitization of human lymphocytes. In specific terms, human lymphocytes are first sensitized in vitro with HB-EGF protein. The immunosensitized lymphocytes are then fused with a suitable fusion partner. For example, myeloma cells of human origin having a permanent cell division ability can be used as the fusion partner (refer to Japanese Patent Publication No. Hei 1-59878). The anti-HB-EGF antibody obtained by this method is a human antibody that has the activity to bind to HB-EGF protein.

Human anti-HB-EGF antibody can also be obtained by administering HB-EGF protein as antigen to a transgenic animal that has the entire human antibody gene repertoire. Antibody-producing cells from the immunized animal can be immortalized by cell fusion with a suitable fusion partner or by a treatment such as infection with the Epstein-Barr virus. Human antibody to the HB-EGF protein can be isolated from the resulting immortalized cells (refer to WO 94/25585, WO 93/12227, WO 92/03918, and WO 94/02602). Moreover, cells that produce antibody having the desired reaction specificity can also be cloned by cloning the immortalized cells. When a transgenic animal is employed as the immunized animal, the animal's immune system recognizes human HB-EGF as foreign. This makes it possible to readily obtain human antibody directed against human HB-EGF. The monoclonal antibody-producing hybridoma constructed in the described manner can be subcultured in the usual culture media. Long-term storage of the hybridoma in liquid nitrogen is also possible.

The aforementioned hybridoma can be cultured according to the usual methods and the desired monoclonal antibody can be obtained from the resulting culture supernatant. Or, the hybridoma can be injected to a mammal compatible with the cells and monoclonal antibody can be obtained from the ascites fluid of the mammal. The former method is well suited for the production of high-purity antibody.

The present invention can also use antibody encoded by an antibody gene that has been cloned from an antibody-producing cell. Antibody expression can be achieved by incorporating the cloned antibody gene into a suitable vector followed by transfection into a host. Methods have already been established for isolating the antibody gene and inserting it into a vector and for transforming the host cell (refer, for example, to Vandamme, A. M. et al., *Eur. J. Biochem.* (1990) 192, 767-775).

For example, cDNA encoding the variable region (V region) of the anti-HB-EGF antibody can be obtained from a hybridoma cell that produces anti-HB-EGF antibody. The total RNA is typically first extracted from the hybridoma. The following method, for example, can be used to extract the mRNA from cells: the guanidine ultracentrifugal method (Chirgwin, J. M. et al., *Biochemistry* (1979) 18, 5294-5299) and the AGPC method (Chomczynski, P. et al., *Anal. Biochem.* (1987) 162, 156-159).

The extracted mRNA can be purified using, for example, an mRNA Purification Kit (GE Healthcare Biosciences). Or, kits for the direct extraction of the total mRNA from cells are also commercially available, such as the QuickPrep mRNA Purification Kit (GE Healthcare Biosciences). Kits such as these can also be used to obtain the total mRNA from hybridomas. cDNA encoding the antibody V region can be synthesized from the obtained mRNA using a reverse transcriptase. The cDNA can be synthesized with, for example, an AMV Reverse Transcriptase First-Strand cDNA Synthesis Kit (Seikagaku Corporation). In addition, a 5'-Ampli FINDER RACE Kit (Clontech) and the PCR-based 5'-RACE method (Frohman, M. A. et al., *Proc. Natl. Acad. Sci. USA* (1988) 85, 8998-9002; Belyaysky, A., et al., *Nucleic Acids Res.* (1989) 17, 2919-2932) can be used to synthesize and amplify the cDNA. Moreover, suitable restriction enzyme sites, infra, can be introduced at both ends of the cDNA in such a cDNA synthesis procedure.

The target cDNA fragment is purified from the obtained PCR product and is then ligated with vector DNA; the recombinant vector fabricated in this manner is transfected into, for example, *E. coli*, and colonies are selected; and the desired recombinant vector can be prepared from the *E. coli* that has exhibited colony formation. In addition, known methods, for example, the dideoxynucleotide chain termination method, can be used to ascertain whether the recombinant vector has the base sequence of the target cDNA.

In order to obtain a gene that encodes the variable region, PCR using variable region gene amplification primers can also be employed. First, cDNA is synthesized using extracted mRNA as the template in order to obtain a cDNA library. A commercially available kit is conveniently used to synthesize the cDNA library. In actuality, the amount of mRNA obtained from only a small number of cells will be quite small, and thus its direct purification provides a low yield. Accordingly; purification is generally carried out after the addition of carrier RNA that clearly does not contain the antibody gene. Or, in those cases in which a certain amount of RNA can be extracted, it may be possible to achieve an efficient extraction even with only the RNA from the antibody-producing cells. For example, in some cases it may not be necessary to add carrier RNA to RNA extraction from at least 10 or at least 30 and preferably at least 50 antibody-producing cells.

Employing the obtained cDNA library as a template, the antibody gene can be amplified by PCR. Primers for the PCR-based amplification of antibody genes are known. For example, primers for the amplification of human antibody genes can be designed based on the information in the literature (for example, *J. Mol. Biol.* (1991) 222, 581-597). These primers have a base sequence that varies with the immunoglobulin subclass. Thus, when a cDNA library of unknown subclass is employed as the template, PCR is carried out considering all of the possibilities.

In specific terms, when the goal is, for example, the acquisition of genes encoding human IgG, primers can be used that have the ability to amplify genes encoding γ1 to γ5 for the heavy chain and the κ chain and λ chain for the light chain. In order to amplify the IgG variable region gene, a primer that anneals to the region corresponding to the hinge region is ordinarily used for the 3'-side primer. On the other hand, a primer adapted for each subclass can be used for the 5'-side primer.

The PCR products based on gene amplification primers for each heavy chain and light chain subclass are made as respective independent libraries. Using the libraries thus synthesized, immunoglobulin comprising a heavy chain plus light chain combination can be reconstructed. The desired antibody may be screened using as an indicator the binding activity of the reconstructed immunoglobulin for HB-EGF.

Binding by the antibody of the present invention to HB-EGF is more preferably specific binding. Screening for antibody that binds HB-EGF can be carried out, for example, by the following steps:
(1) bringing HB-EGF into contact with antibody comprising a V region encoded by cDNA obtained from a hybridoma;
(2) detecting binding between the HB-EGF and the antibody; and
(3) selecting antibody that binds to the HB-EGF.

Methods of detecting binding between an antibody and HB-EGF are known. In specific terms, the test antibody may be reacted with HB-EGF that has been immobilized on a carrier and then reacted with a labeled antibody that recognizes the antibody. When, after washing, the labeled antibody can be detected on the carrier as an indicator of binding of the test antibody to the HB-EGF. A fluorescent substance such as FITC or an enzymatic protein such as peroxidase or β-galactoside can be used for the label. HB-EGF-expressing cells in immobilized form can also be used to evaluate the antibody's binding activity.

Panning using a phage vector can also be employed as a method of antibody screening using binding activity as the indicator. Screening using a phage vector is advantageous when as described above the antibody genes are obtained as heavy chain subclass and light chain subclass libraries. The genes encoding the heavy chain and light chain variable regions can be made into a single-chain Fv (scFv) by linking with a suitable linker sequence. The scFv-encoding gene may be inserted into a phage vector to obtain a phage that expresses scFv on its surface. The phage is brought into contact with the target antigen, and the recovery of phage that was bound to the antigen enables the recovery of DNA coding for scFv that has the desired binding activity. scFv having the desired binding activity can be enriched by repeating this process as necessary.

In the present invention, antibody-encoding polynucleotide may encode the full length of the antibody or may encode a portion of the antibody. This portion of the antibody may be any portion of the antibody molecule. Antibody fragment is a term used below in some instances to indicate a portion of an antibody. Preferred antibody fragments in the present invention comprise the complementarity determining region (CDR). A more preferred antibody fragment in the present invention comprises all of the three CDRs that constitute the variable region.

Once the cDNA encoding the V region of the target anti-HB-EGF antibody has been obtained, cDNA is digested by restriction enzymes that recognize the restriction enzyme sites that have been inserted at both ends of the cDNA. Preferred restriction enzymes will recognize and digest base sequences that have a low potential of occurrence in the base sequence constituting the antibody gene. In order to insert 1 copy of the digestion fragment in the correct direction in the vector, a restriction enzyme that provides cohesive ends is preferred. An antibody expression vector can be obtained by inserting the cDNA encoding the anti-HB-EGF antibody V region, digested as described in the preceding, into a suitable expression vector. At this point, a chimeric antibody can be obtained through the in-frame fusion of a gene encoding the antibody constant region (C region) with the aforementioned V region-encoding gene. Here, chimeric antibody refers to a product having different origins for the constant region and variable region. Accordingly, in the context of the present invention "chimeric antibody" also encompasses human-human allochimeric antibodies in addition to heterochimeric antibodies such as mouse-human. A chimeric antibody expression vector can also be constructed by inserting the aforementioned V region gene into an expression vector that already carries the constant region.

In specific terms, for example, a restriction enzyme recognition sequence for a restriction enzyme used to digest the aforementioned V region gene can be disposed in advance on the 5' side of an expression vector that holds the DNA coding for the desired antibody constant region (C region). Digestion of the two with the same restriction enzyme combination and in-frame fusion results in the construction of a chimeric antibody expression vector.

In order to produce the anti-HB-EGF antibody of the present invention, the antibody gene can be incorporated in the expression vector in such a manner that expression occurs under control by an expression control region. Expression control regions for antibody expression include, for example, enhancers and promoters. Recombinant cells that express DNA coding for anti-HB-EGF antibody can then be obtained by transforming suitable host cells with the expression vector under consideration.

For expression of the antibody gene, the DNA coding for the antibody heavy chain (H chain) and the DNA coding for the antibody light chain (L chain) can be incorporated in separate expression vectors. An antibody molecule provided with H and L chains can be expressed by simultaneously transforming (co-transfect) the same host cell with the vector incorporating the H chain and the vector incorporating the L chain. Or, DNA encoding the H chain and L chain may be incorporated in a single expression vector and the host cell may then be transformed (WO 94/11523).

Numerous host/expression vector combinations are known for antibody production by isolating the antibody gene and transfecting a suitable host. Any of these expression systems may be applied to the present invention. Animal cells, plant cells, or fungal cells can be used when eukaryotic cells are used as the host. Specific examples of animal cells that can be used in the present invention are as follows:

(1) mammalian cells (e.g., CHO, COS, myeloma, baby hamster kidney (BHK), Hela, Vero, and for so forth),
(2) amphibian cells (e.g., *Xenopus laevis* oocytes and so forth), and
(3) insect cells (e.g., sf9, sf21, Tn5, and so forth).

In the case of plant cells, antibody gene expression systems based on cells from genus *Nicotiana*, e.g., *Nicotiana tabacum* and so forth, are known. Callus-cultured cells can be used for plant cell transformation.

The following, for example, can be used as the fungal cells:
yeast: e.g., *Saccharomyces* such as *Saccharomyces cerevisiae*, *Pichia* such as *Pichia pastoris*, and so forth, and filamentous fungi: e.g., *Aspergillus* such as *Aspergillus niger*.

Antibody gene expression systems using prokaryotes are also known. Taking bacteria as an example, bacteria such as *E. coli, Bacillus subtilis*, and so forth, can be used in the present invention.

When a mammalian cell is used, an expression vector can be constructed by functionally ligating an effective, commonly used promoter, the antibody gene that is to be expressed, and a polyA signal downstream at the 3'-terminal of the antibody gene. An example of a promoter/enhancer is the human cytomegalovirus immediate early promoter/enhancer.

Other promoter/enhancers that can be used to express the antibody of the present invention are, for example, viral promoter/enhancers and promoter/enhancers that originate in mammalian cells, such as human elongation factor 1α (HEF1α). Specific examples of viruses that can provide usable promoter/enhancers are retroviruses, polyoma viruses, adenoviruses, and simian virus 40 (SV40).

The SV40 promoter/enhancer can be used according to the method of Mulligan et al. (*Nature* (1979) 277, 108). In addition, the HEF1α promoter/enhancer can be readily utilized for the desired gene expression according to the method of Mizushima et al. (*Nucleic Acids Res*. (1990) 18, 5322).

In the case of *E. coli*, expression of the gene under consideration can be achieved by functionally ligating an effective, commonly used promoter, a signal sequence for antibody secretion, and the antibody gene that is to be expressed. The promoter can be, for example, the lacZ promoter or the araB promoter. The lacZ promoter can be used according to the method of Ward et al. (*Nature* (1989) 341, 544-546; *FASEB J*. (1992) 6, 2422-2427). Or, the araB promoter can be used for the desired gene expression according to the method of Better et al. (*Science* (1988) 240, 1041-1043).

With regard to the signal sequence for antibody secretion, the pelB signal sequence (Lei, S. P. et al., *J. Bacteriol*. (1987) 169, 4379) may be used in the case of production in the *E. coli* periplasm. After the antibody produced in the periplasm has been isolated, the antibody structure can be reorganized (refolded)—by the use of a protein denaturant such as the guanidine hydrochloride and urea—so as to exhibit the desired binding activity.

The origin of replication inserted into the expression vector can be, for example, an origin of replication originating in SV40, polyoma virus, adenovirus, bovine papilloma virus (BPV), and so forth. In addition, a selection marker can be inserted in the expression vector for amplification of the gene copy number in the host cell system. In specific terms, usable selection markers are, inter alia, as follows:
the aminoglycoside transferase (APH) gene,
the thymidine kinase (TK) gene,
the E. coli xanthine-guanine phosphoribosyltrasnferase (Ecogpt) gene, and
the dihydrofolate reductase (dhfr) gene.

The target antibody can be produced by transfecting the expression vector under consideration into a host cell and culturing the transformed host cell in vitro or in vivo. Host cell culture can be carried out according to known methods. For example, DMEM, MEM, RPMI1640, or IMDM can be used as the culture medium; a serum supplement such as fetal calf serum (FCS) can also be added.

The antibody expressed and produced as described above can be purified by the usual methods known for use for protein purification; a single such method can be used or suitable combinations of these methods can be used. The antibody can be isolated and purified using suitable selections and combinations of, for example, an affinity column (for example, a protein A column), column chromatography, filtration, ultrafiltration, salting out, dialysis, and so forth (Antibodies: A Laboratory Manual. Ed Harlow and David Lane, Cold Spring Harbor Laboratory, 1988).

In addition to host cells as described in the preceding, transgenic animals can also be used to produce recombinant antibodies. That is, the antibody under consideration can be obtained from an animal into which a gene encoding the target antibody has been introduced. For example, a fused gene can be fabricated by the in-frame insertion of the antibody gene within a gene coding for a protein that is natively produced in milk. For example, goat β-casein can be used as the protein secreted into milk. A DNA fragment containing the fused gene that incorporates the antibody gene may be injected into a goat embryo and the injected embryo may be introduced into a female goat. The desired antibody can be obtained as a fusion protein with the milk protein from the milk produced by the transgenic goat (or its offspring) born from the embryo-implanted goat. In addition, hormones can be used as appropriate on the transgenic goat in order to increase the amount of milk containing the desired antibody that is produced from the transgenic goat (Ebert, K. M. et al., Bio/Technology (1994) 12, 699-702). C regions originating in animal antibodies can be used as the C region of the recombinant antibody of the present invention. The mouse antibody H chain C regions designated Cγ1, Cγ2a, Cγ2b, Cγ3, Cμ, Cδ, Cα1, Cα2, and Cε can be used, and the L chain C regions designated as Cκ and Cλ can be used. Animal antibodies from, for example, the rat, rabbit, goat, sheep, camel, monkey, and so forth, can be used as animal antibodies other than mouse antibodies. These sequences are known. The C region can be modified in order to improve the antibody or improve the stability of its production. When the antibody will be administered to humans, an artificially engineered genetically recombinant antibody can be made in the present invention with the goal, for example, of lowering the foreign antigenicity in the human. Such a genetically recombinant antibody includes, for example, chimeric antibodies and humanized antibodies. These engineered antibodies can be produced using known methods. A chimeric antibody denotes an antibody in which a variable region is ligated to a constant region that has a different origin from the variable region. For example, an antibody having a heavy chain variable region and a light chain variable region from a mouse antibody and a heavy chain constant region and light chain constant region from a human antibody is a mouse-human heterochimeric antibody. A recombinant vector that expresses chimeric antibody can be constructed by ligating DNA that encodes mouse antibody variable region to DNA that encodes human antibody constant region and incorporating it into an expression vector. A recombinant cell transformed by the vector is then cultured to bring about expression of the incorporated DNA, and the produced chimeric antibody in the culture medium can then be recovered. The C region of human antibody is used for the C region of chimeric antibodies and humanized antibodies. With regard to the H chain, for example, Cγ1, Cγ2, Cγ3, Cγ4, Cμ, Cδ, Cα1, Cα2, and Cε can be used for the C region. For the L chain, Cκ and Cλ can be used for the C region. The amino acid sequences of these C regions are known, as are the base sequences that code for these amino acid sequences. In addition, the human antibody C region can be modified in order to improve the antibody itself or improve the stability of antibody production.

Chimeric antibodies are generally constructed from the V regions of antibodies of nonhuman animal origin and the C regions of antibodies of human origin. In contrast, a humanized antibody is constructed of complementarity determining regions (CDRs) from antibody of nonhuman animal origin, framework regions (FRs) from antibody of human origin, and C regions from antibody of human origin. Humanized antibodies are useful as active ingredients in therapeutic agents of the present invention with the goal of lowering the antigenicity in the human body.

For example, preferred monoclonal antibodies in the present invention are mouse-human chimeric antibodies obtained by ligating an amino acid sequence constituting a human constant region with the variable region of the HA-20, HB-20, or HC-15 anti-HB-EGF antibody mouse monoclonal antibodies constructed based on the present invention. The present invention thus provides a mouse-human chimeric monoclonal antibody comprising the H chain and L chain with the following amino acid sequences.
H chain: the amino acid sequence from positions 1 to 330 in the amino acid sequence of SEQ ID NO: 10
L chain: the amino acid sequence from positions 1 to 107 in the amino acid sequence with SEQ ID NO: 20

The variable region of an antibody is typically constructed of three CDRs sandwiched in four FRs. The CDRs are regions that substantially determine the binding specificity of an antibody. The amino acid sequences of CDRs are richly diverse. The amino acid sequences that form the FRs, on the other hand, frequently exhibit high homology even between antibodies that have different binding specificities. Due to this, the binding specificity of a certain antibody can typically be grafted into another antibody by CDR grafting.

Humanized antibodies are also known as reshaped human antibodies. In specific terms, for example, humanized antibodies are known in which the CDRs from a nonhuman animal antibody, such as a mouse antibody, have been grafted into a human antibody. General genetic recombination techniques for obtaining humanized antibodies are also known.

In specific terms, for example, overlap extension PCR is known as a method for grafting mouse antibody CDRs into human FRs. In overlap extension PCR, a base sequence encoding the mouse antibody CDR to be grafted is added to a primer for the synthesis of human antibody FR. Primers are prepared for each of the four FRs. The selection of human FR that exhibits a high homology with mouse FR is generally advantageous for maintenance of CDR function in the grafting of mouse CDR to human FR. Thus, the use is generally preferred of human FR that has an amino acid sequence that exhibits high homology with the amino acid sequence of the FR adjacent to the mouse CDR to be grafted.

In addition, the base sequences that are ligated are designed so as to join with each other in-frame. The human FRs are synthesized separately using primers for each. In this way, products are obtained in which DNA encoding mouse CDR is appended to each FR. The base sequences encoding the mouse CDR in each product are designed so as to overlap with each other. Then, the overlapping CDR regions of the products synthesized templated on the human antibody gene are annealed to each other and a complementary chain synthesis reaction is carried out. This reaction results in ligation of the human FRs via the mouse CDR sequences.

Finally, the variable region gene comprising four FRs ligated with three CDRs is submitted to full length amplification by annealing, at its 5' end and 3' end, primers to which suitable restriction enzyme recognition sequences have been added. An expression vector for human-type antibody can be constructed by inserting the DNA obtained as described above and DNA encoding a human antibody C region into an expression vector in such a manner that they are fused in-frame. The thus-formulated vector is inserted into a host and a recombinant cell is established; the recombinant cell is cultured to express the DNA encoding the humanized antibody; and humanized antibody is thereby produced in the culture medium of the cultured cells (refer to EP 239,400 and WO 96/02576).

Human antibody FRs that when ligated across CDRs enable the CDRs to form high-quality antigen binding sites, can be suitably selected by qualitatively or quantitatively measuring and evaluating the binding activity to antigen by humanized antibody that has been constructed as described in the preceding. Amino acid substitution can also be carried on the FRs as necessary so as to enable the CDRs of the reshaped human antibody to form well-adapted antigen binding sites. For example, mutations in the amino acid sequence can be introduced into an FR using the PCR methodology used to graft mouse CDRs onto human FRs. In specific terms, partial base sequence mutations can be introduced in the primers that are annealed to the FR. Base sequence mutations are then introduced into the FR synthesized using such primers. A mutated FR sequence having the desired properties can be selected by measurement and evaluation, by the methods described above, of the antigen binding activity of the mutated, amino acid-substituted antibody (Sato, K. et al., *Cancer Res.*, 1993, 53, 851-856).

Methods for obtaining human antibodies are also known. For example, human lymphocytes can be sensitized in vitro with a desired antigen or with cells that express a desired antigen. The desired human antibody capable of binding to the antigen can then be obtained by fusing the sensitized lymphocytes with human myeloma cells (refer to Japanese Patent Publication No. H1-59878). For example, U266 can be used for the human myeloma cell employed as the fusion partner.

A desired human antibody can also be obtained by immunizing a transgenic animal having the entire human antibody gene repertoire with a desired antigen (refer to International Publications WO 93/12227, WO 92/03918, WO 94/02602, WO 94/25585, WO 96/34096, and WO 96/33735). Technology for obtaining human antibodies by panning using a human antibody library are also known. For example, the human antibody V region can be expressed as a single chain antibody (scFv) on the surface of a phage by the phage display method and phage that binds to an antigen can be selected. The DNA sequence that codes for the V region of human antibody that binds the antigen can then be established by analysis of the genes of the selected phage. Once the DNA sequence of the antigen-binding scFv has been established, the V region sequence can be in-frame fused with a sequence for the desired human antibody C region, after which an expression vector can be constructed by insertion in an appropriate expression vector. The expression vector can be transfected into an appropriate expression cell as described above and human antibody can be obtained by expression of the gene coding for the human antibody. These methods are already known (International Publications WO 92/01047, WO 92/20791, WO 93/06213, WO 93/11236, WO 93/19172, WO 95/01438, and WO 95/15388).

Insofar as binding to the HB-EGF protein occurs, the antibody according to the present invention encompasses not only bivalent antibody as typified by IgG, but also polyvalent antibody as typified by IgM and monovalent antibody. Polyvalent antibody according to the present invention includes polyvalent antibody in which all the antigen binding sites are the same and polyvalent antibody in which some or all of the antigen binding sites are different. Antibody according to the present invention is not limited to the full length antibody molecule, but includes low molecular weight antibody and modifications thereof, insofar as these can bind to the HB-EGF protein.

Low molecular weight antibody encompasses antibody fragments generated by the deletion of a portion of the whole antibody (for example, whole IgG). A partial deletion of the antibody molecule is permissible as long as the ability to bind to the HB-EGF antigen is present. The antibody fragment used in the present invention preferably comprises either the heavy chain variable region (VH) or the light chain variable region (VL) or both. The amino acid sequence of the VH or VL can comprise substitutions, deletions, additions, and/or insertions. Moreover, a portion of either the VH or VL or of both can also be deleted, insofar as the ability to bind the HB-EGF antigen remains present. The variable region may also be chimerized or humanized. Specific examples of antibody fragments are Fab, Fab', F(ab')2, and Fv. Specific examples of low molecular weight antibodies are Fab, Fab', F(ab')2, Fv, scFv (single chain Fv), diabody, and sc(Fv)2 (single chain (Fv)2). Multimers of these antibodies (e.g., dimers, trimers, tetramers, polymers) are also encompassed by the low molecular weight antibodies of the present invention.

The antibody fragments can be obtained by the enzymatic treatment of an antibody to produce antibody fragments. For example, papain, pepsin, plasmin, and so forth, are known as enzymes that produce antibody fragments. Or, a gene encoding such an antibody fragment can be constructed and inserted into an expression vector followed by expression by a suitable host cell (refer, for example, to Co, M. S. et al., *J. Immunol.* (1994) 152, 2968-2976; Better, M. & Horwitz, A. H. *Methods in Enzymology* (1989) 178, 476-496; Plueckthun, A. & Skerra, A. *Methods in Enzymology* (1989) 178, 476-496; Lamoyi, E. *Methods in Enzymology* (1989) 121, 652-663; Rousseaux, J. et al., *Methods in Enzymology* (1989) 121, 663-669; and Bird, R. E. et al., *TIBTECH* (1991) 9, 132-137).

A digestive enzyme cleaves specific antibody fragment sites to yield antibody fragments with specific structures as described below. Any portion of the antibody can be deleted when genetic engineering techniques are applied to these enzymatically generated antibody fragments.

papain digestion: F(ab)2 or Fab
pepsin digestion: F(ab')2 or Fab'
plasmin digestion: Facb Diabody designates a bivalent antibody fragment that is constructed by gene fusion (Holliger, P. et al., *Proc. Natl. Acad. Sci. USA* 90, 6444-6448 (1993), EP 404,097, WO 93/11161, and so forth). A diabody is a dimer built up from two polypeptide chains. In general, each of the polypeptide chains constituting a diabody is a VL and a VH ligated by a linker into one and the same chain. The linker for a diabody is generally sufficiently short that the VL and VH are unable to bind to one another. In specific terms, for example, about five amino acid residues make up the linker. Due to this, the VL and VH coded on the same polypeptide chain are unable to form a single chain variable region fragment and form a dimer with a separate single chain variable region fragment. Thus a diabody has two antigen binding sites.

scFv is obtained by ligating the H chain V region of an antibody to the L chain V region. The H chain V region and L chain V region in scFv are ligated to each other by a linker and preferably a peptide linker (Huston, J. S. et al., *Proc. Natl. Acad. Sci. USA* 85, 5879-5883 (1988)). The H chain V region and L chain V region in the scFv may originate from any antibody described herein. There are no particular limitations on the peptide linker that links the V regions. For example, any single peptide chain having from about 3 to 25 residues can be used as the linker. In specific terms, for example, the peptide linkers described below can be used.

The V regions can be linked, for example, using the PCR techniques described in the preceding. In order to link the V regions by PCR, DNAs coding for all or a desired portion of the amino acid sequence from the following DNAs are first used as templates:

a DNA sequence coding for the H chain or H chain V region of the antibody, and
a DNA sequence coding for the L chain or L chain V region of the antibody.

The DNA encoding the H chain V region and the DNA encoding the L chain V region are each amplified by PCR using pairs of primers that have sequences that correspond to the sequences at the two ends of the DNA to be amplified. DNA coding for the peptide linker region is then prepared. The peptide linker-encoding DNA can also be synthesized using PCR. A base sequence that can join with each of the separately synthesized V region amplification products is added in advance to the 5' side of the primers used. A PCR reaction is then run using assembly PCR primers and each of the DNAs for [H chain V region DNA]-[peptide linker DNA]-[L chain V region DNA]. The assembly PCR primers are a combination of a primer that anneals to the 5' side of the [H chain V region DNA] and a primer that anneals to the 3' side of the [L chain V region DNA]. That is, the assembly PCR primers form a primer set that can amplify DNA that encodes the full length sequence of the scFv that is to be synthesized. On the other hand, base sequences that can join with each V region DNA are added to the [peptide linker DNA]. As a result, these DNAs are joined and, in addition, the full length of the scFv is finally produced as an amplification product by the assembly PCR primers. Once the scFv-encoding DNA has been produced, an expression vector containing the DNA as well as recombinant cells transformed by the expression vector can be obtained by the usual methods. In addition, the recombinant cells thus obtained can be cultured and scFv can be obtained through expression of the scFv-encoding DNA.

sc(Fv)2 is a low molecular weight antibody in which two VHs and two VLs are ligated by, for example, a linker, into a single chain (Hudson et al., *J. Immunol. Methods,* 231, 177-189 (1999)). sc(Fv)2 can be prepared, for example, by joining scFv's with a linker.

This is preferably an antibody that characteristically has the two VHs and the two VLs lined up in the sequence, considered from the N-terminal side of the single chain polypeptide, VH, VL, VH, VL ([VH]linker-[VL]linker-[VH]linker-[VL]).

The sequence of the two VHs and the two VLs is not particularly limited to the arrangement cited above and they may be aligned in any sequence. The following sequences can be provided as examples.

[VL]linker-[VH]linker-[VH]linker-[VL]
[VH]linker-[VL]linker-[VL]linker-[VH]
[VH]linker-[VH]linker-[VL]linker-[VL]
[VL]linker-[VL]linker-[VH]linker-[VH]
[VL]linker-[VH]linker-[VL]linker-[VH]

The linker connecting the variable regions of the antibody can be, for example, any peptide linker that can be inserted by genetic engineering or a synthetic compound linker, for example, as disclosed in *Protein Engineering,* 9(3), 299-305 (1996). Peptide linkers are preferred in the present invention. The length of the peptide linker is not particularly limited and can be selected as appropriate by those skilled in the art in view of the intended application. In general, from 1 to 100 amino acid residues, preferably from 3 to 50 amino acid residues, more preferably from 5 to 30 amino acid residues, and particularly preferably from 12 to 18 amino acid residues (for example, 15 amino acid residues) are in the peptide linker.

The amino acid sequence of the peptide linker can be any sequence that does not impair the binding action of the scFv. The following amino acid sequences, for example, can be used for the peptide linker.

Ser

Gly-Ser

Gly-Gly-Ser

Ser-Gly-Gly

| | |
|---|---|
| Gly-Gly-Gly-Ser | (SEQ ID NO: 61) |
| Ser-Gly-Gly-Gly | (SEQ ID NO: 62) |
| Gly-Gly-Gly-Gly-Ser | (SEQ ID NO: 63) |
| Ser-Gly-Gly-Gly-Gly | (SEQ ID NO: 64) |
| Gly-Gly-Gly-Gly-Gly-Ser | (SEQ ID NO: 65) |
| Ser-Gly-Gly-Gly-Gly-Gly | (SEQ ID NO: 66) |
| Gly-Gly-Gly-Gly-Gly-Gly-Ser | (SEQ ID NO: 67) |
| Ser-Gly-Gly-Gly-Gly-Gly-Gly | (SEQ ID NO: 68) |
| (Gly-Gly-Gly-Gly-Ser | (SEQ ID NO: 63))n |
| (Ser-Gly-Gly-Gly-Gly | (SEQ ID NO: 64))n |

[n is an integer with a value of at least 1]

The amino acid sequence of the peptide linker can be selected as appropriate by those skilled in the art in view of the intended application. For example, n, which sets the length of the aforementioned peptide linker, is generally 1 to 5, preferably 1 to 3, and more preferably 1 or 2.

For example, the following sc(Fv)2 is a particularly preferred embodiment of an sc(Fv)2 in the present invention. [VH]peptide linker (15 amino acids) [VL]peptide linker (15 amino acids) [VH]peptide linker (15 amino acids)[VL]

Alternatively, the V regions can also be joined using a synthetic chemical linker (chemical crosslinking agent). Those crosslinking agents typically used to crosslink, for example, peptide compounds, can be used in the present invention. For example, crosslinking agents such as the following are known. These crosslinking agents can be obtained commercially.

N-hydroxysuccinimide (NHS),
disuccinimidyl suberate (DSS),
bis(sulfosuccinimidyl) suberate (BS3),
dithiobis(succinimidylpropionate) (DSP),
dithiobis(sulfosuccinimidylpropionate) (DTSSP),
ethylene glycol bis(succinimidylsuccinate) (EGS),
ethylene glycol bis(sulfosuccinimidylsuccinate) (sulfo-EGS),
disuccinimidyl tartrate (DST),
disulfosuccinimidyl tartrate (sulfo-DST),
bis[2-(succinimidooxycarbonyloxy)ethyl]sulfone (BSOCOES),
bis[2-(sulfosuccinimidooxycarbonyloxy)ethyl]sulfone (sulfo-BSOCOES), and so forth.

Three linkers are ordinarily required when ligating four antibody variable regions. These linkers may be the same as each other or different linkers may be used. Diabody and sc(Fv)2 are preferred low molecular weight antibodies for the present invention. To obtain such low molecular weight antibodies, an antibody may be treated with an enzyme (for example, papain, pepsin, and so forth) to produce antibody fragments, or DNA encoding these antibody fragments may be constructed and inserted into an expression vector followed by expression in a suitable host cell (refer, for example, to Co, M. S. et al., *J. Immunol.* (1994) 152, 2968-2976; Better, M. & Horwitz, A. H. *Methods Enzymol.* (1989) 178, 476-496; Plueckthun, A. and Skerra, A. *Methods Enzymol.* (1989) 178, 497-515; Lamoyi, E. *Methods Enzymol.* (1986) 121, 652-663; Rousseaux, J. et al., *Methods Enzymol.* (1986) 121, 663-669; and Bird, R. E. and Walker, B. W. *Trends Biotechnol.* (1991) 9, 132-137).

Any antibody that recognizes HB-EGF can be employed as the antibody of the present invention. The antibodies according to (1) to (29) below are examples of preferred antibodies. These antibodies may be, for example, whole length antibodies, low molecular weight antibodies, animal antibodies, chimeric antibodies, humanized antibodies, human antibodies, and so forth.

(1) an antibody comprising a heavy chain variable region having the amino acid sequence of SEQ ID NO: 2 as CDR1, the amino acid sequence of SEQ ID NO: 4 as CDR2, and the amino acid sequence of SEQ ID NO: 6 as CDR3

(2) an antibody comprising a heavy chain variable region according to (1) that has the amino acid sequence of SEQ ID NO: 8 as CH (3) an antibody comprising a heavy chain variable region according to (1) that has the amino acid sequence of SEQ ID NO: 10 as CH (4) an antibody comprising a light chain variable region having the amino acid sequence of SEQ ID NO: 12 as CDR1, the amino acid sequence of SEQ ID NO: 14 as CDR2, and the amino acid sequence of SEQ ID NO: 16 as CDR3

(5) an antibody comprising a light chain variable region according to (4) that has the amino acid sequence of SEQ ID NO: 18 as CL (6) an antibody comprising a light chain variable region according to (4) that has the amino acid sequence of SEQ ID NO: 20 as CL (7) an antibody comprising the heavy chain according to (1) and the light chain according to (4)

(8) an antibody comprising the heavy chain according to (2) and the light chain according to (5)

(9) an antibody comprising the heavy chain according to (3) and the light chain according to (6)

(10) an antibody comprising a heavy chain variable region having the amino acid sequence of SEQ ID NO: 22 as CDR1, the amino acid sequence of SEQ ID NO: 24 as CDR2, and the amino acid sequence of SEQ ID NO: 26 as CDR3

(11) an antibody comprising a heavy chain variable region according to (10) that has the amino acid sequence of SEQ ID NO: 28 as CH

(12) an antibody comprising a heavy chain variable region according to (10) that has the amino acid sequence of SEQ ID NO: 10 as CH

(13) an antibody comprising a light chain variable region having the amino acid sequence of SEQ ID NO: 30 as CDR1, the amino acid sequence of SEQ ID NO: 32 as CDR2, and the amino acid sequence of SEQ ID NO: 34 as CDR3

(14) an antibody comprising a light chain variable region according to (13) that has the amino acid sequence of SEQ ID NO: 18 as CL

(15) an antibody comprising a light chain variable region according to (13) that has the amino acid sequence of SEQ ID NO: 20 as CL

(16) an antibody comprising the heavy chain according to (10) and the light chain according to (13)

(17) an antibody comprising the heavy chain according to (11) and the light chain described in (14)

(18) an antibody comprising the heavy chain according to in (12) and the light chain according to (15)

(19) an antibody comprising a heavy chain variable region having the amino acid sequence of SEQ ID NO: 36 as CDR1, the amino acid sequence of SEQ ID NO: 38 as CDR2, and the amino acid sequence of SEQ ID NO: 40 as CDR3

(20) an antibody comprising a heavy chain variable region according to (19) that has the amino acid sequence of SEQ ID NO: 28 as CH

(21) an antibody comprising a heavy chain variable region according to (19) that has the amino acid sequence of SEQ ID NO: 10 as CH

(22) an antibody comprising a light chain variable region having the amino acid sequence of SEQ ID NO: 42 as CDR1, the amino acid sequence of SEQ ID NO: 44 as CDR2, and the amino acid sequence of SEQ ID NO: 46 as CDR3

(23) an antibody comprising a light chain variable region according to (22) that has the amino acid sequence of SEQ ID NO: 18 as CL

(24) an antibody comprising a light chain variable region according to (22) that has the amino acid sequence of SEQ ID NO: 20 as CL

(25) an antibody comprising the heavy chain according to (19) and the light chain according to (22)

(26) an antibody comprising the heavy chain according to (20) and the light chain according to (23)

(27) an antibody comprising the heavy chain according to (21) and the light chain according to (24)

(28) an antibody obtained by the substitution of one or a plurality of amino acids in, deletion of one or a plurality of amino acids from, addition of one or a plurality of amino acids to, and/or insertion of one or a plurality of amino acids into an antibody according to any of (1) to (27) and having the activity equivalent to that of the antibody according to any of (1) to (27)

(29) an antibody that binds to an epitope that is the same as the epitope of HB-EGF protein that is bound by an antibody according to any of (1) to (27)

A VH having the amino acid sequence of SEQ ID NO: 48 is an example of the VH in an "H chain having the amino acid sequence of SEQ ID NO: 2 as CDR1, the amino acid sequence of SEQ ID NO: 4 as CDR2, and the amino acid sequence of SEQ ID NO: 6 as CDR3" according to (1) above.

A VL having the amino acid sequence of SEQ ID NO: 50 is an example of the VL in an "L chain having the amino acid sequence of SEQ ID NO: 12 as CDR1, the amino acid sequence of SEQ ID NO: 14 as CDR2, and the amino acid sequence of SEQ ID NO: 16 as CDR3" according to (4) above.

A VH having the amino acid sequence of SEQ ID NO: 52 is an example of the VH in an "H chain having the amino acid sequence of SEQ ID NO: 22 as CDR1, the amino acid sequence of SEQ ID NO: 24 as CDR2, and the amino acid sequence of SEQ ID NO: 26 as CDR3" according to (12) above.

A VL having the amino acid sequence of SEQ ID NO: 54 is an example of the VL in an "L chain having the amino acid sequence of SEQ ID NO: 30 as CDR1, the amino acid sequence of SEQ ID NO: 32 as CDR2, and the amino acid sequence of SEQ ID NO: 34 as CDR3" according to (15) above.

A VH having the amino acid sequence of SEQ ID NO: 56 is an example of the VH in an "H chain having the amino acid sequence of SEQ ID NO: 36 as CDR1, the amino acid sequence of SEQ ID NO: 38 as CDR2, and the amino acid sequence of SEQ ID NO: 38 as CDR3" according to (23) above.

A VL having the amino acid sequence of SEQ ID NO: 58 is an example of the VL in an "L chain having the amino acid sequence of SEQ ID NO: 42 as CDR1, the amino acid sequence of SEQ ID NO: 44 as CDR2, and the amino acid sequence of SEQ ID NO: 46 as CDR3" according to (26) above.

In the case of antibody according to (28) above, the "equivalent activity" denotes at least an $EC_{50}$ value of 50 nM or less for the inhibitory effect on the HB-EGF-dependent growth of EGFR_Ba/F3 cells and an at least 80% inhibition of the binding between HB-EGF and EGFR when the antibody is added at a concentration of 50 μg/mL. A preferred embodiment of antibody according to (28) above is antibody that has been modified or engineered in a region other than the CDRs. As one example, a preferred embodiment among the antibodies covered by (28) of "an antibody obtained by the substitution of one or a plurality of amino acids in, deletion of one or a plurality of amino acids from, addition of one or a plurality of amino acids to, and/or insertion of one or a plurality of amino acids into an antibody according to (1) and having the activity equivalent to that of the antibody according to (1)" is "an antibody comprising a heavy chain having the amino acid sequence of SEQ ID NO: 2 as CDR1, the amino acid sequence of SEQ ID NO: 4 as CDR2, and the amino acid sequence of SEQ ID NO: 6 as CDR3, comprising an antibody obtained by the substitution of one or a plurality of amino acids in, deletion of one or a plurality of amino acids from, addition of one or a plurality of amino acids to, and/or insertion of one or a plurality of amino acids into an antibody according to (1) and having the activity equivalent to that of the antibody according to (1)". Preferred embodiments of other antibodies encompassed by the antibody according to (28) can be elaborated in the same manner.

The introduction of mutation into a polypeptide is a method well known to those skilled in the art for producing a polypeptide that is functionally equivalent to a particular polypeptide. For example, as known to those skilled in the art, antibody that exhibits the activity equivalent to that of an antibody of the present invention can be produced by introducing suitable mutations into the antibody of the present invention using site-specific mutagenesis (Hashimoto-Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA 82, 488-492; and Kunkel T. A. (1988) Methods Enzymol. 85, 2763-2766). Amino acid mutations may also be produced by natural mutation. The antibody of the present invention also encompasses antibody that has an amino acid sequence generated by one or more amino acid mutations in the amino acid sequence of an antibody of the present invention and that exhibits the activity equivalent to that of the antibody of the present invention. With regard to the number of amino acids that have been mutated in such a mutant, generally no more than 50 amino acids, preferably no more than 30 amino acids, and more preferably no more than 10 amino acids (for example, no more than 5 amino acids) can be considered.

Preferably, the amino acid residue is mutated to another amino acid residue that conserves the characteristics of the amino acid side chain. For example, the following classification has been established based on the characteristics of the amino acid side chain.

hydrophobic amino acids (A, I, L, M, F, P, W, Y, V)
hydrophilic amino acids (R, D, N, C, E, Q, G, H, K, S, T)
amino acids having an aliphatic side chain (G, A, V, L, I, P)
amino acids having a hydroxyl-containing side chain (S, T, Y)
amino acids having a sulfur-containing side chain (C, M)
amino acids having a carboxyl- or amide-containing side chain (D, N, E, Q)
amino acids having a base-containing side chain (R, K, H)
amino acids having an
aromatic-containing side chain (H, F, Y, W)
(The single letter designation for the amino acids is given in the parentheses.)

In the case of a polypeptide having a modified amino sequence generated by deleting and/or adding one or a plurality of amino acid residues from and/or to a particular amino acid sequence and/or by substituting one or a plurality of amino acid residues in the particular amino sequence with another amino acid, it is already known that such a polypeptide can maintain its biological activity (Mark, D. F. et al., Proc. Natl. Acad. Sci. USA (1984) 81, 5662-5666; Zoller, M. J. and Smith, M., Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413). That is, when, in the amino acid sequence of a particular polypeptide, the amino acids in a particular classification are substituted by other amino acids in that classification, there is a high probability that the activity of the particular polypeptide will be retained. Substitutions between amino acids in the same classification in the amino acid classification provided above are designated in the present invention as conservative substitutions.

In (29), supra, the present invention also provides antibody that binds to an epitope that is the same as the epitope bound by anti-HB-EGF antibody disclosed by the present invention.

Thus, the present invention relates to antibody that recognizes the same epitope as the epitope recognized by the antibodies HA-20, HB-20, and HC-15; the present invention also relates to the applications of such an antibody. Such an antibody can be obtained, for example, by the following method.

Whether a test antibody and a particular antibody have a common epitope can be determined by competition by the two for the same epitope. Competition between antibodies can be detected, for example, by a reciprocal blocking assay. For example, a competitive ELISA assay is a preferred reciprocal blocking assay. In specific terms, in a reciprocal blocking assay, HB-EGF protein is coated on the wells of a microtiter plate; pre-incubated in the presence or absence of the candidate competitive antibody; then the anti-HB-EGF antibody of the present invention is added. The amount of anti-HB-EGF antibody of the present invention that has become bound to the HB-EGF protein in the well is indirectly correlated with the binding activity of the candidate competitive antibody (test antibody) competing for binding to the same epitope. That is, the higher the affinity of the test antibody for the same epitope, the less anti-HB-EGF antibody of the present invention that binds to the HB-EGF protein-coated well and the greater the amount of binding by the test antibody to the HB-EGF protein-coated well.

The amount of well-bound antibody can be conveniently measured by labeling the antibody in advance. For example, biotin-labeled antibody can be measured using an avidin-peroxidase conjugate and a suitable substrate. A reciprocal blocking assay based on an enzyme label such as peroxidase is in particular known as a competitive ELISA assay. The antibody can be labeled with some other label that can be detected or measured. In specific terms, radioactive labels and fluorescent labels are also known.

In addition, when the test antibody has a constant region originating from a species different from that for the anti-HB-EGF antibody of the present invention, the amount of well-bound antibody can also be measured using a labeled secondary antibody that recognizes the constant region of the antibody. Or, even when the antibody originates in the same species but the classes are different, the amount of well-bound antibody can be measured using a secondary antibody that discriminates among the individual classes.

When—in comparison to the binding activity obtained in the control test that is carried out in the absence of the candidate competitive antibody—the candidate antibody can block binding of at least 20%, preferably at least 20 to 50%, and even more preferably at least 50% of the anti-HB-EGF antibody, such a candidate competitive antibody is then an antibody that binds to substantially the same epitope as the anti-HB-EGF antibody of the present invention or that competes for binding to the same epitope.

Antibody according to (29) above is an example of antibody that binds to the same epitope as the epitope bound by anti-HB-EGF antibody, but not limited to.

In addition, the antibody according to (1) to (29) above encompasses, as noted above, not only monovalent antibody, but also polyvalent antibody. Polyvalent antibody according to the present invention encompasses polyvalent antibody in which all the antigen binding sites are the same and polyvalent antibody in which some or all of the antigen binding sites are different.

The following antibodies are examples of polyvalent antibodies that have different antigen binding sites; however, the antibody of the present invention is not limited to these antibodies.

(A) antibody comprising an H chain and L chain pair (referred to as an HL pair in the following) according to (7) above and an HL pair according to (16) or (25) above
(B) antibody comprising an HL pair according to (8) above and an HL pair according to (17) or (26) above
(C) antibody comprising an HL pair according to (9) above and an HL pair according to (18) or (27) above
(D) antibody comprising an HL pair according to (7) above and an HL pair according to (28) above
(E) antibody comprising an HL pair according to (8) above and an HL pair according to (28) above
(F) antibody comprising an HL pair according to (9) above and an HL pair according to (28) above
(G) antibody comprising an HL pair according to (7) above and an HL pair according to (29) above
(H) antibody comprising an HL pair according to (8) above and an HL pair according to (29) above
(I) antibody comprising an HL pair according to (9) above and an HL pair according to (29) above
(J) antibody comprising an HL pair according to (16) above and an HL pair according to (25) above
(K) antibody comprising an HL pair according to (17) above and an HL pair according to (26) above
(L) antibody comprising an HL pair according to (18) above and an HL pair according to (27) above
(M) antibody comprising an HL pair according to (16) above and an HL pair according to (28) above
(N) antibody comprising an HL pair according to (17) above and an HL pair according to (28) above
(O) antibody comprising an HL pair according to (18) above and an HL pair according to (28) above
(P) antibody comprising an HL pair according to (16) above and an HL pair according to (29) above
(Q) antibody comprising an HL pair according to (17) above and an HL pair according to (29) above
(R) antibody comprising an HL pair according to (18) above and an HL pair according to (29) above In addition, the antibody of the present invention can also be used in the form of a modified antibody to which various molecules, for example, polyethylene glycol (PEG) and so forth, are attached. These modified antibodies can be obtained by chemical modification on the antibody according to the present invention. Antibody modification methods have already been established in the art.

The antibody of the present invention may also be a bispecific antibody. A bispecific antibody is an antibody that has, within the same antibody molecule, variable regions that recognize different epitopes, wherein these epitopes may be present in different molecules or may be present in a single molecule. Thus, in the context of the present invention, a bispecific antibody can have antigen binding sites that recognize different epitopes on the HB-EGF molecule. With such a bispecific antibody, two antibody molecules can bind to one HB-EGF molecule. Therefore a stronger cytotoxicity can be expected. These antibodies are also encompassed by the "antibody" according to the present invention.

The present invention also encompasses bispecific antibody that recognizes an antigen other than HB-EGF. For example, the present invention encompasses bispecific antibody that recognizes an antigen different from HB-EGF, wherein the antigen is specifically expressed on the cell surface of cancer cells that are the same targets as with HB-EGF.

Methods of producing bispecific antibodies are known. For example, a bispecific antibody can be produced by joining two antibodies that recognize different antigens. Each of the joined antibodies may be a half-molecule that has an H chain and an L chain or may be a quarter-molecule that has only an H chain. Or, a fused cell that produces bispecific antibody can also be produced by fusing hybridomas that produce different monoclonal antibodies. Bispecific antibodies can additionally be produced by genetic engineering techniques.

Binding Activity of the Antibody, Neutralizing Activity of the Antibody, and Ability of the Antibody to Inhibit Proliferation Known procedures can be used to measure the antigen binding activity of an antibody (Antibodies: A Laboratory Manual. Ed Harlow and David Lane, Cold Spring Harbor Laboratory, 1988). For example, an enzyme-linked immunosorbent assay (ELISA), enzyme immunoassay (EIA), radioimmunoassay (RIA), or immunofluorescence procedure can be used. The method described on pages 359 to 420 of Antibodies: A Laboratory *Manual* is an example of a procedure for measuring the binding activity by an antibody for antigen expressed in a cell.

In addition, procedures that in particular employ a flow cytometer can be suitably used to measure binding between antigen expressed on the surface of cells suspended in, for example, buffer, and antibody against the antigen. Examples of usable flow cytometers are as follows: FACSCanto (registered trademark) II, FACSAria (registered trademark), FACSArray (registered trademark), FACSVantage (registered trademark) SE, and FACSCalibur (registered trademark) (the preceding instruments are from BD Biosciences), and EPIS ALTRA HyPerSort, Cytomics FC 500, EPICS XL-MCL ADC EPICS XL ADC, and Cell Lab Quanta/Cell Lab Quanta SC (the preceding instruments are from Beckman Coulter).

In one example of a convenient method for measuring the binding activity of a test HB-EGF antibody for an antigen, the test antibody is reacted with a cell that expresses HB-EGF, and stained with FITC-labeled secondary antibody that recognizes the test antibody. The fluorescent intensity is measured with FACSCalibur (Becton, Dickinson and Company) and analyzed with CELL QUEST software (Becton, Dickinson and Company). According to this method, when the test antibody bound to membrane-bound HB-EGF on an HB-EGF-expressing cell is stained with FITC-labeled secondary antibody that recognizes the test antibody and the fluorescent intensity is measured with a FACSCalibur, the "absence of binding to HB-EGF protein on the cell surface of HB-EGF-expressing cells" can be determined by comparing the geometric mean value (test Geo-Mean value) obtained by analysis of the resulting fluorescence intensity using CELL QUEST software with the binding activity (control Geo-Mean value) for antibody that strongly reacts with membrane-bound HB-EGF, for example, a commercially available antibody (for example, AF-259-NA from R&D Systems, Inc.) or HC-15. Thus, the test antibody is designated herein as exhibiting an "absence of binding to HB-EGF protein on the cell surface of HB-EGF-expressing cells" when the test Geo-Mean value is at least less than 10% of the control Geo-Mean value and preferably is less than 5% and more preferably is less than 2%. The procedure for calculating the Geo-Mean value (geometric means) is described in the CELL QUEST Software User's Guide (BD Biosciences).

The antibody of the present invention is preferably antibody that exhibits a neutralizing activity. A neutralizing activity generally refers to the ability to inhibit the biological activity of a ligand that exhibit biological activity on a cell (viruses and toxins are examples of such a ligand). Thus, a substance that has a neutralizing activity denotes a substance that binds to such a ligand—or to the receptor that binds the ligand—and thereby inhibits binding by the ligand or by the receptor. The receptor prevented from binding with the ligand as a consequence of the neutralizing activity is then unable to manifest the biological activity that proceeds through the receptor. An antibody that exhibits such a neutralizing activity is generally known as a neutralizing antibody. The neutralizing activity of a particular test substance can be measured by comparing the biological activity in the presence of the ligand and the test substance with the biological activity in the presence of the ligand and the absence of the test substance.

The EGF receptor is considered to be the principal receptor for the HB-EGF described herein. In this case, a dimer is formed due to binding by the ligand and a tyrosine kinase, which is its own domain within the cell, is thereby activated. The activated tyrosine kinase causes the formation by autophosphorylation of phosphorylated tyrosine-containing peptide, with which various signal transduction accessory molecules associate. These are principally PLCγ (phospholipase Cγ), Shc, Grb2, and so forth. Among these accessory molecules, the former two are additionally phosphorylated by the tyrosine kinase of the EGF receptor. The principal pathway in, signal transduction from the EGF receptor is a pathway in which phosphorylation is transduced in the sequence Shc, Grb2, Sos, Ras, Raf/MAPK kinase/MAP kinase. A pathway from PLCγ to PKC, which is a secondary pathway, is additionally thought to be present. This intracellular signal cascade is different in each cell type, and therefore a suitable target molecule can be established for each desired target cell and there is no limitation to the factors cited above. The neutralizing activity can be evaluated by measuring in vivo signal activation. Commercially available kits for measuring in vivo signal activation can be suitably used (for example, the protein kinase C activation measurement system from GE Healthcare Biosciences).

In vivo signal activation can also be detected by focusing on the induction of transcription for a target gene that is present downstream in the in vivo signal cascade. Changes in the transcription activity for a target gene can be detected using the reporter assay concept. In specific terms, a reporter gene (e.g., green fluorescent protein (GFP) or luciferase) can be disposed downstream from the transcription factor or promoter region of the target gene, and by measuring the reporter activity the change in transcription activity can be measured in terms of the reporter activity.

In addition, since signal transduction through the EGF receptor generally acts in the direction of promoting cell growth, the neutralizing activity can be evaluated by measuring the growth activity of the target cell. In the examples provided below, the neutralizing activity of neutralizing antibody according to the present invention is evaluated using evaluation of the cell growth activity, but the invention is limitation to this method. The neutralizing activity may be evaluated by any of known methods suitable for the particular target cell.

The following methods are conveniently used to evaluate or measure the inhibiting effect—based on the neutralizing activity of anti-HB-EGF antibody—on the proliferation of cells whose proliferation is promoted by HB-EGF. In a method that can be used to evaluate or measure the cell proliferation inhibiting activity in vitro, the uptake by live cells of [$^3$H]-labeled thymidine added to the medium is measured as an index of the DNA replication ability. Methods that are more convenient include the MTT method and dye exclusion methods in which the ability of cells to exclude a dye (e.g., trypan blue) is measured using a microscope. The MTT method utilizes the fact that live cells have the ability to convert the tetrazolium salt MTT (3-(4,5-dimethylthiazol-2-yl)-2,5-diphenyltetrazolium bromide) into a blue formazan product. More specifically, the ligand and test antibody are added to the culture fluid of the test cell and, after a specified time has passed, an MTT solution is added to the culture fluid and MTT is incorporated into the cells by standing for a specified period of time. As a result, MTT, which is a yellow compound, is converted into a blue compound by succinate dehydrogenase in the mitochondria within the cells. The blue product is dissolved to provide coloration, and measurement of its absorbance provides an index to the viable cell count. In addition to MTT, reagents such as MTS, XTT, WST-1, WST-8, and so forth are also commercially available (Nacalai Tesque, Inc.) and can be suitably used. In the activity measurement, a control antibody is used in the same way as the anti-HB-EGF antibody; the control antibody is a binding antibody that has the same isotype as the anti-HB-EGF antibody while not having the aforementioned cell proliferation inhibiting activity. The antibody has the cell proliferation inhibiting activity when the anti-HB-EGF antibody exhibits a stronger cell proliferation inhibiting activity than the control antibody.

The examples provide herein use the following cells for activity evaluation whose proliferation is promoted by HB-EGF: the RMG-1 cell line, which is an ovarian cancer cell line, and mouse Ba/F3 cells that have been transformed with a vector in which there is operably ligated a gene coding for hEGFR/mG-CSFR (SEQ ID NO: 86), which is a fusion protein obtained by the in-frame fusion of the extracellular domain of human EGFR (its polypeptide sequence is shown by SEQ ID NO: 78) and the intracellular domain of the mouse GCSF receptor (its polypeptide sequence is shown by SEQ ID NO: 84). However, the cells used to evaluate activity are not limited to the foregoing, and any cells whose proliferation is promoted by HB-EGF may be used as appropriate.

Tumor-supporting mouse models may also be used as a method for evaluating or measuring the cell proliferation inhibiting activity in vivo. For example, cancer cells whose growth is promoted by HB-EGF may be subcutaneously or intracutaneously grafted into a nonhuman test animal, after which the test antibody may be administered intravenously or intraabdominally every day or on a multiday interval beginning on the day of grafting or on the next day. The cell proliferation inhibiting activity can be evaluated by measuring tumor size with elapsed time. Just as with the in vitro evaluation, a control antibody having the same isotype is administered, and the antibody has a cell proliferating inhibiting activity when the tumor size in the group receiving the anti-HB-EGF antibody is significantly smaller than the tumor size in the group receiving the control antibody. The nude (nu/nu) mouse is suitably employed when the mouse is used as the nonhuman test animal; the nude (nu/nu) mouse lacks T-lymphocyte function due to the genetic loss of the thymus gland. The use of this type of mouse makes it possible to exclude a contribution by T-lymphocytes in the test animal in the evaluation•measurement of the cell proliferation inhibiting activity due to the administered antibody.

A more preferred embodiment of the antibody used in the present invention is antibody that lacks an effector activity such as ADCC activity and/or CDC activity. The inhibition of effector activity can be an inhibition that occurs due to the antibody isotype and/or subtype, and when the antibody is a chimeric antibody or humanized antibody can be an inhibition that occurs due to the origin of the Fc region used. In the case of human antibodies, IgM antibody is an antibody isotype that lacks ADCC activity while IgG4 antibody is an antibody subtype that lacks ADCC activity (Clinical Aspects of Immunology, 5th Edition, 1799-1830, 1993). For example, IgG4 antibody is suitably used as an antibody subtype that lacks CDC activity. An even more suitable antibody is IgG4 antibody, which lacks both ADCC activity and CDC activity.

In the case of mouse antibodies and rat antibodies, IgG1 antibody can be used as an antibody that lacks both ADCC activity and CDC activity.

In addition, when a chimeric antibody or humanized antibody being constructed by the methods described above using genetic engineering techniques, antibody in which the effector activity can be modulated can be suitably constructed by using an antibody gene that codes for—as the Fc region that is used in the chimeric antibody or humanized antibody being constructed—an Fc region that originates from an antibody isotype or subtype as cited above.

The Cell Proliferation Inhibitor

The present invention provides a method of inhibiting the proliferation of cells whose proliferation is promoted by HB-EGF, comprising bringing such cells into contact with antibody that binds to HB-EGF protein. The antibody that binds to HB-EGF protein, which is present in the cell proliferation inhibitor of the present invention, is an HB-EGF protein-binding antibody as has been described above. There are no particular limitations on the cells that may be brought into contact with the anti-HB-EGF antibody other than that these cells express HB-EGF, but pancreatic cancer, liver cancer, esophageal cancer, melanoma, colorectal cancer, gastric cancer, ovarian cancer, bladder cancer, and brain tumors are preferred.

"Contact" in the present invention may be carried out by adding the antibody to the culture medium of HB-EGF-expressing cells that are being cultured in vitro. With regard to the state in which the antibody is added here, for example, a solid obtained by freeze-drying or a solution may suitably be used. In those instances where the antibody is added in the form of the aqueous solution, this may be an aqueous solution that contains only the pure antibody or may be a solution that contains, for example, surfactant, excipient, colorant, flavorant, preservative, stabilizer, buffer, suspending agent, tonicity agent, binder, disintegrant, lubricant, fluidity promoter, taste-masking agent, and so forth. While there are no particular limitations on the concentration of addition, suitable final concentrations in the culture fluid are preferably 1 pg/mL to 1 g/mL, more preferably 1 ng/mL to 1 mg/mL, and even more preferably 1 µg/mL to 1 mg/mL.

In another embodiment of the present invention, "contact" may also be carried out by administration to a nonhuman animal into which HB-EGF-expressing cells have been implanted, transplanted, or grafted, or by administration to an animal that bears HB-EGF-expressing cancer cells. The mode of administration may be oral administration or parenteral administration. Parenteral administration is particularly preferred, and the corresponding routes of administration may include injection, transnasal administration, transpulmonary administration, transdermal administration, and so forth. With regard to examples of administration by injection, the pharmaceutical composition of the present invention, as a cell proliferation inhibitor or anti-cancer agent, can be administered systemically or locally by, for example, intravenous injection, intramuscular injection, intraperitoneal injection, or subcutaneous injection. The appropriate mode of administration can be selected as a function of the age and symptomatology of the animal subject. In those instances where an aqueous solution is administered, this solution may be an aqueous solution that contains only the pure antibody or may be a solution that contains, for example, surfactant, excipient, colorant, flavorant, preservative, stabilizer, buffer, suspending agent, tonicity agent, binder, disintegrant, lubricant, fluidity promoter, taste-masking agent, and so forth. The dosage, for example, may be selected from the range of 0.0001 mg to 1000 mg per 1 kg body weight per administration. Alternatively, the dosage may be selected, for example, from the range of 0.001 to 100000 mg/body per patient. However, the dosage of the antibody of the present invention is not limited to the preceding dosages.

The same tests as cited above for measuring the neutralizing activity can be employed to evaluate or measure the inhibitory effect due to contact with the anti-HB-EGF antibody on the proliferation of cells whose growth is promoted by HB-EGF. In this case, it can be ascertained whether these cells grow according to an autocrine modality by comparing the activity in the presence of ligand with the activity in the absence of ligand. Evaluation or measurement of the in vivo cell proliferation inhibiting activity can be carried out by evaluating or measuring the activity using the same tests as described above for measuring the neutralizing activity in vivo.

The Pharmaceutical Composition

In another aspect, a characteristic feature of the present invention is a pharmaceutical composition that comprises, as an active ingredient, an antibody that binds to HB-EGF protein. An additional characteristic feature of the present invention is a cell proliferation inhibitor—and particularly an anti-cancer agent—that comprises, as an active ingredient, an antibody that binds to HB-EGF protein. The cell proliferation inhibitor of the present invention and the anti-cancer agent of the present invention are preferably administered to a subject suffering from cancer or to a subject at risk for cancer.

In the present invention, the cell proliferation inhibitor comprising HB-EGF protein-binding antibody as an active ingredient also subsumes a method of inhibiting cell proliferation comprising a step of administering HB-EGF protein-binding antibody to a subject as well as the use of HB-EGF protein-binding antibody for the production of a cell proliferation inhibitor.

Moreover, in the present invention, the anti-cancer agent comprising HB-EGF protein-binding antibody as an active ingredient subsumes a method of preventing or treating cancer comprising a step of administering HB-EGF protein-binding antibody to a subject as well as the use of HB-EGF protein-binding antibody for the production of an anti-cancer agent.

In the present invention, "comprising HB-EGF protein-binding antibody as an active ingredient" means that anti-HB-EGF antibody is present as the main active ingredient, but there are no limitations on the anti-HB-EGF antibody content.

There are no particular limitations on the antibody present in the pharmaceutical composition of the present invention (for example, a cell proliferation inhibitor or an anti-cancer agent; this also applies below) other than that this antibody has the ability to bind to HB-EGF protein, and any of the antibodies provided herein as examples may also be used.

The mode of administration of the pharmaceutical composition of the present invention may be oral administration or parenteral administration. Parenteral administration is particularly preferred, and the corresponding routes of administration may include injection, transnasal administration, transpulmonary administration, transdermal administration, and so forth. With regard to examples of administration by injection, the pharmaceutical composition of the present invention can be administered systemically or locally by, for example, intravenous injection, intramuscular injection, intraperitoneal injection, or subcutaneous injection. The appropriate mode of administration can be selected as a function of the age and symptomatology of the patient. The dosage, for example, may be selected from the range of 0.0001 mg to 1000 mg per 1 kg body weight per administration. Alternatively, the dosage may be selected from the range of 0.001 to 100000 mg/body per patient. However, the pharmaceutical composition of the present invention is not limited to the preceding dosages.

The pharmaceutical composition of the present invention can be formulated according to the usual methods (for example, Remington's Pharmaceutical Science, latest edition, Mark Publishing Company, Easton, USA) and may comprise a pharmaceutically acceptable vehicle and pharmaceutically acceptable additives. Examples are surfactants, excipients, colorants, flavorants, preservatives, stabilizers, buffers, suspending agents, tonicity agents, binders, disintegrants, lubricants, fluidity promoters, taste-masking agents, and so forth, but there is no limitation to the preceding and other generally used vehicles can be employed as appropriate. Specific examples are light silicic anhydride, lactose, crystalline cellulose, mannitol, starch, carmellose calcium, carmellose sodium, hydroxypropyl cellulose, hydroxypropylmethyl cellulose, polyvinyl acetal diethylamino acetate, polyvinylpyrrolidone, gelatin, medium-chain fatty acid triglycerides, polyoxyethylene hardened castor oil 60, sucrose, carboxymethyl cellulose, corn starch, inorganic salts, and so forth.

The contents of all the patents and reference literature explicitly cited in the specification are herein incorporated by reference in their entirety. The contents of the specification and drawings in Japanese Patent Application Number 2006-286824, which application forms the basis for the priority cited by the present application, are also herein incorporated by reference in their entirety.

EXAMPLES

The present invention is described in greater detail by the examples provided below, but the present invention is not limited by these examples.

Immunization 1-1. Immunogen Production 1-1-1. Construction of an HB-EGF Expression Vector In order to construct an HB-EGF expression vector, an HB-EGF gene was first cloned as described below. Using human heart cDNA (human Marathon Ready cDNA, Clontech Laboratories, Inc.) as template, RT-PCT was carried out using Pyrobest Taq polymerase (Takara Bio Inc.) and the full-length HG-EGF gene was cloned.

```
EGF-1: ATGAAGCTGCTGCCGTCGGTG        (SEQ ID NO: 69)

EGF-2: TCAGTGGGAATTAGTCATGCCC       (SEQ ID NO: 70)
```

(94° C./30 s, 65° C./30 s, 72° C./60 s: 35 cycles)

Using the obtained PCR product as template, double PCR was carried out under the conditions given below and a full-length HB-EGF cDNA fragment was obtained in which SalI and NotI cleavage sequences were added, respectively, at the 5' and 3' terminals.

```
EGF-3:
                                   (SEQ ID NO: 71)
TAAGTCGACCACCATGAAGCTGCTGCCGTCGGTG
```

-continued

EGF-4:
(SEQ ID NO: 72)
TTTGCGGCCGCTCACTTGTCATCGTCGTCCTTGTAGTCGTGGGAAT
TAGTCATGCCCAAC (94° C./30 s, 65° C./30 s, 72° C./60 s: 25 cycles)

The fragment was digested with SalI and NotI and was inserted into an expression vector for use with animal cells (pMCN) that had likewise been digested with SalI and NotI, thus constructing an HB-EGF expression vector (pMCN_HB-EGF).

1-1-2. Construction of an HB-EGF_Fc Fusion Protein Expression Vector

A fusion protein (HB-EGF_Fc) between the extracellular region of HB-EGF and the Fc region of mouse IgG2a was used as the immunogen for acquisition of HB-EGF neutralizing antibody. The structure of the immunizing fusion protein is shown in FIG. 1.

The expression vector for the mouse Fc region/HB-EGF fusion protein was constructed as described below. First, using the HB-EGF expression vector (pMCN_HB-EGF) as template, PCR was carried out under the following conditions using Pyrobest Taq polymerase (Takara Bio Inc.).

EGF-5:
(SEQ ID NO: 73)
AAAGAATTCCACCATGAAGCTGCTGCCGTC

EGF-6:
(SEQ ID NO: 74)
TATCGGTCCGCGAGGTTCGAGGCTCAGCCCATGACACCTC (94° C./30 s, 68° C./30 s, 72° C./30 s: 25 cycles)

The obtained PCR product was then digested with EcoRI and CpoI. The resulting DNA fragment was inserted between EcoRI and CpoI in an animal cell expression vector that contained mouse IgG2a_Fc (pMCDN_mIgG2a_Fc) to construct an HB-EGF-Fc expression vector (pMCDN_HB-EGF-Fc).

1-1-3. Creation of an HB-EGF_Fc-Producing Strain

15 µg of the HB-EGF-Fc expression vector pMCDN_HB-EGF-Fc, which had been linearized by digestion with pvuI, was transfected by electroporation at 1.5 kV/25 µFD (Gene Pulser from Bio-Rad Laboratories, Inc.) into DG44 cells ($1 \times 10^7$ cells/mL, 800 µL) suspended in PBS(−). After dilution to a suitable cell count with a growth medium (CHO-S-SFM II, Invitrogen Corporation) containing penicillin/streptomycin (PS), the cells were seeded to 96-well plates and 500 µg/mL G418 (geneticin, Invitrogen Corporation) was added the next day. After about 2 weeks, wells having a monoclone were selected under a microscope and SDS-PAGE was run using 10 µL of the culture supernatant from each. Cell lines producing HB-EGF-Fc were screened by Western blotting using a PVDF membrane and goat anti-HB-EGF antibody (AF-259-NA, R&D Systems, Inc.) and HRP-anti-goat antibody (ACI3404, BioSource). The highest producing strain was selected and subjected to expansion culture.

1-1-4. Purification of the HB-EGF_Fc Protein

The HB-EGF_Fc protein was purified from the culture supernatant of the obtained HB-EGF_Fc-producing strain using a HiTrap Protein G HP 1 mL column (Amersham Biosciences #17-0404-01). The culture supernatant was adsorbed at a flow rate of 1 mL/min followed by washing with 20 mL 20 mM phosphate buffer (pH 7.0) and then elution with 3.5 mL 0.1 M glycine-HCl (pH 2.7). The eluate was recovered in 0.5 mL fractions in Eppendorf tubes, each of which already contained 50 µL 1 M Tris-HCL (pH 9.0). The $OD_{280\ nm}$ was measured. The fractions containing the target protein were combined and PBS(−) was added to bring to a total of 2.5 mL, then the buffer was replaced with PBS(−) using a PD-10 column (Amersham Biosciences #17-0851-01). The purified protein was passed through a 0.22 µm filter (Millipore #SLGV033RS) and was stored at 4° C.

1-2. Immunization

An emulsion of the HB-EGF_Fc protein was prepared with Complete Adjuvant (DIFCO DF263810) for the initial immunization and with Incomplete Adjuvant (DIFCO DF263910) for the second and subsequent immunizations. Three animals [(MRL/lpr, male, age: 4 weeks) (balb/c, female, age: 6 weeks), both purchased from Charles River Japan] were immunized by subcutaneous injection at 50 µg/mouse (1 mL Thermo syringe, 26-gauge needle). The second immunization was given two weeks after the initial immunization, and a total of 4-5 immunizations were given on a one week interval. For the final immunization, the HB-EGF_Fc (50 µg) was suspended in 100 µL PBS and was injected into the tail vein; cell fusion was carried out three days later.

1-3. Hybridoma Production

Cell fusion was carried out as follows. The spleen was aseptically removed from the mouse and a single cell suspension was prepared by grinding in medium 1 (RPMI1640+PS). The suspension was passed through a 70 µm nylon mesh (Falcon) to remove fatty tissue and so forth and the cells were counted. The obtained B cells were mixed with mouse myeloma cells (P3U1 cells) in a cell count ratio of about 2:1; 1 mL 50% PEG (Roche, catalogue number 783641) was added; and cell fusion was carried out. The fused cells were suspended in medium 2 (RPMI1640+PS, 10% FCS, HAT (Sigma, H0262), 5% BM Condimed H1 (Roche #1088947)) and distributed at 200 µL/well into a suitable number of 96-well plates (10 plates); and cultivated at 37° C. After one week, hybridoma were screened using the culture supernatant and analyzed. The hybridomas originating from two Balb/c mice were designated as the HA series and the HB series, respectively, and the hybridomas originating from one Mrl/lpr mouse were designated as the HC series.

Screening for Anti-HB-EGF Neutralizing Antibody 2-1. Creation of Human HB-EGF-Expressing Cell Lines 2-1-1. Creation of the Strain HB-EGF_DG44

An HB-EGF-expressing DG44 cell line was established as follows. First, 15 µg of the HB-EGF expression vector (pMCN_HB-EGF) constructed as described in 1-1-1 was digested with pvuI and was transfected into DG44 cells by electroporation using the same procedure as in 1-1-3. Then the G418-resistant strains were picked out and the cells were stained with goat anti-HB-EGF antibody (R&D Systems, Inc.) and FITC-labeled anti-goat IgG antibody. The HB-EGF expressed on the cell surface was analyzed with a FACSCalibur (Becton, Dickinson and Company) and the high-expressing clone was selected.

2-1-2. Creation of the Strain HB-EGF_Ba/F3

A Ba/F3 cell line that expressed HB-EGF on the cell membrane was established as follows. It is known that the HB-EGF expressed on the cell membrane is processed by protease and cleaved into the culture medium. Therefore, an expression vector for proHB-EGF mutated at the protease cleavage site was first constructed.

Using pMCN-HB-EGF as template, separate PCRs were carried out using the following two sets of conditions and Pyrobest Taq polymerase (Takara Bio Inc.).

```
PCR reaction 1
                                      (SEQ ID NO: 71)
EGF-3: TAAGTCGACCACCATGAAGCTGCTGCCGTCGGTG (SEQ ID NO: 75)
EGF-7: CGATTTTCCACTGTGCTGCTCAGCCCATGACACCTCTC
```

(94° C./30 s, 68° C./30 s, 72° C./30 s: 20 cycles)

```
PCR reaction 2
EGF-8:
                                      (SEQ ID NO: 76)
TGGGCTGAGCAGCACAGTGGAAAATCGCTTATATACCTA EGF-4:
                                      (SEQ ID NO: 72)
TTTGCGGCCGCTCACTTGTCATCGTCGTCCTTGTAGTCGTGGGAAT

TAGTCATGCCCAAC
```

(94° C./30 s, 68° C./30 s, 72° C./30 s: 20 cycles)

The two DNA fragments obtained by PCR reactions 1 and 2 were then mixed; a recombination reaction (94° C./30 s, 72° C./60 s: 5 cycles) was run using Pyrobest Taq polymerase (Takara Bio Inc.); followed by PCR under the following conditions using 1 µL of the preceding reaction solution as template.

```
EGF-3:
                                      (SEQ ID NO: 71)
TAAGTCGACCACCATGAAGCTGCTGCCGTCGGTG

EGF-4:
                                      (SEQ ID NO: 72)
TTTGCGGCCGCTCACTTGTCATCGTCGTCCTTGTAGTCGTGGGAAT

TAGTCATGCCCAAC
```

(94° C./30 s, 68° C./30 s, 72° C./60 s: 22 cycles)

The obtained PCR product was digested with SalI and NotI followed by insertion into an expression vector for use in animal cells (pMCN) that had likewise been digested with SalI and NotI, in order to construct a proHB-EGF expression vector (pMCN-MHB-EGF).

A Ba/F3 cell line that expressed proHB-EGF was then created as described in the following. 15 µg of the previously constructed proHB-EGF expression vector (pMCN-MHB-EGF) was cleaved with pvuI and then transfected by electroporation at 0.33 kV/950 µFD (Gene Pulser from Bio-Rad Laboratories, Inc.) into Ba/F3 cells suspended in PBS(–) (1×10⁷ cells/mL, 800 µL). These cells were then cultured in 96-well plates on medium (RPMI1640, 10% FCS, PS) containing 1 ng/mL IL-3 and 500 µg/mL G418, and after two weeks the G418-resistant strains were picked out. The cells were stained with goat anti-HB-EGF antibody (R&D Systems, Inc.) and FITC-labeled anti-mouse IgG antibody (Beckman Coulter, PN IM0819) and the clone was selected that presented a high level of expression of cell surface HB-EGF according to FACS (Becton, Dickinson and Company).

2-2. Creation of HB-EGF-Expressing SKOV-3 Cells

A SKOV-3 cell line that expressed HB-EGF was established as described in the following. SKOV-3 (purchased from ATTC), which is an ovarian cancer cell line, was cultured on a growth medium (McCoy 5A medium, Invitrogen) that contained 10% FCS and penicillin/streptomycin (P/S).

15 µg of the HB-EGF expression vector (pMCN_HB-EGF) constructed in 1-1-1 was digested with pvuI. This was followed by transfection by electroporation at 1.5 kV/25 µF (Gene Pulser from Bio-Rad Laboratories, Inc.) into SKOV-3 cells suspended in PBS(–) (1×10⁷ cells/mL, 800 µL). Dilution to a suitable cell count using the growth medium cited above was followed by seeding to 96-well plates. G418 (geneticin, Invitrogen Corporation) was added the next day at 500 µg/mL. After about two weeks the G418-resistant monoclones were selected and screened for HB-EGF-expressing cell lines by Western blotting. The highest producing line was selected and used in subsequent experiments.

Figure 2A:
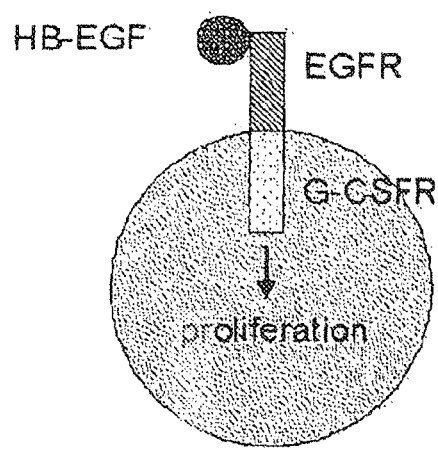
FIG. 2a is a diagram that schematically depicts the influence of the binding of HB-EGF to the EGFR_Ba/F3 cell.

2-3. Creation of an EGFR_Ba/F3 Cell Line that Exhibits HB-EGF-Dependent Growth 2-3-1. Construction of pCV-hEGFR/G-CSFR In order to evaluate the activity of antibody of the present invention, a vector was constructed that expressed a chimeric receptor (hEGFR/mG-CSFR) composed of the extracellular region of human EGFR and the intracellular region of mouse G-CSFR. The effect on a cell that expresses the chimeric receptor when HB-EGF binds to such a cell is shown schematically in FIG. 2a.

In order to clone the gene encoding the extracellular region of the human epidermal growth factor receptor (EGFR), PCR was carried out with human liver cDNA (Marathon Ready cDNA, Clontech Laboratories, Inc.) as a template using the primer set specified below. The base sequence (MN_005228) and the amino acid sequence (NP_005219) of human EGFR are shown, respectively, in SEQ ID NO: 77 and SEQ ID NO: 78.

```
EGFR-1: ATGCGACCCTCCGGGACGGC        (SEQ ID NO: 79)

EGFR-2: CAGTGGCGATGGACGGGATCT       (SEQ ID NO: 80)
```

(94° C./30 s, 65° C./30 s, 72° C./2 min: 35 cycles)

The amplified cDNA (approximately 2 kb) was excised from the agarose gel and was inserted into the pCR-TOPO vector (Invitrogen Corporation). The base sequence of the fragment inserted into this plasmid was analyzed and confirmed that the obtained EGFR gene had the correct sequence. PCR was then carried out with the plasmid obtained as above as a template using the following primer set.

```
EGFR-5:
                                      (SEQ ID NO: 81)
TTGCGGCCGCCACCATGCGACCCTCCGGGACGGC

EGFR-6:
                                      (SEQ ID NO: 82)
ACCAGATCTCCAGGAAAATGTTTAAGTCAGATGGATCGGACGGGATCT

TAGGCCCATTCGT
```

(94° C./30 s, 68° C./30 s, 72° C./2 min: 25 cycles)

A gene fragment was obtained that encoded the EGFR extracellular region and that had a 5' NotI site and a 3' BglII site. This fragment was digested with NotI-BglII and inserted between NotI-BamHI in pCV_mG-CSFR.

The expression plasmid vector pCV was constructed by replacing the poly(A) addition signal of pCOS1 (WO 98/13388) with the poly(A) addition signal from human G-CSF. pEF-BOS (Mizushima S. et al., *Nucleic Acids Res.* 18, 5322 (1990)) was digested with EcoRI and XbaI to obtain the poly(A) addition signal fragment originating from human G-CSF. This fragment was inserted into pBacPAK8 (Clontech Laboratories, Inc.) at the EcoRI/XbaI sites. After digested with EcoRI, both terminals were blunted and digested with BamHI, resulted in the production of a fragment containing the poly(A) addition signal of human G-CSF origin having a BamHI site added at the 5' terminal and a blunted 3' terminal. This fragment was exchanged with the poly(A) addition signal of pCOS1 at the BamHI/EcoRV sites, giving the expression plasmid vector designated pCV.

pCV_mG-CSFR comprises the mouse G-CSF receptor from the asparagine residue at position 623 to the C terminal, which is the intracellular region, in pCV. The base sequence (M58288) of the mouse G-CSF receptor is shown in SEQ ID NO: 83 and the amino acid sequence (AAA37673) of the mouse G-CSF receptor is shown in SEQ ID NO: 84. However, the glycine reside at position 632 in SEQ ID NO: 84 is replaced by a glutamic acid residue due to the creation of a BamHI site (restriction enzyme site) in the coding cDNA sequence at the N-terminal region in the insertion sequence of pCV_mG-CSFR.

Construction of the vector (pCV_hEGFR/mG-CSFR) expressing the chimeric receptor (hEGFR/mG-CSFR) composed of the extracellular region of human EGFR and the intracellular region of mouse G-CSFR was completed by confirming the base sequence of the gene fragment inserted in pCV_mG-CSFR.

The base sequence and amino acid sequence for the protein expressed by the expression vector, i.e., a human EGFR/mouse G-CSFR chimeric receptor, are shown, respectively, in SEQ ID NO: 85 and SEQ ID NO: 86.

2-3-2. Creation of an HB-EGF-Dependent Cell Line

15 µg of the (hEGFR/mG-CSFR) chimeric receptor expression vector (pCV_hEGFR/mG-CSFR), linearized by digestion with pvuI, was transfected by electroporation (Gene Pulser, Bio-Rad Laboratories, Inc.) at 0.33 kV/950 µFD into Ba/F3 cells. These cells were cultured for 2 weeks on medium (RPMI1640, 10% FCS, PS) containing 10 ng/mL HB-EGF and 500 µg/mL G418 and the emergent colony was picked up.

It was then determined in the following experiment if the obtained cell line exhibited growth dependent on the HB-EGF concentration. The EGFR_Ba/F3 cells were seeded to 96-well plates at $1\times10^3$ cells/well in the presence of 0 to 100 ng/mL HB-EGF (R&D Systems, Inc., 259-HE) followed by incubation for 3 days. Then the cell count was measured using the WST-8 reagent (Cell Counting Kit-8, Dojindo Laboratories) in accordance with the manufacturers instructions.

Figure 2B:
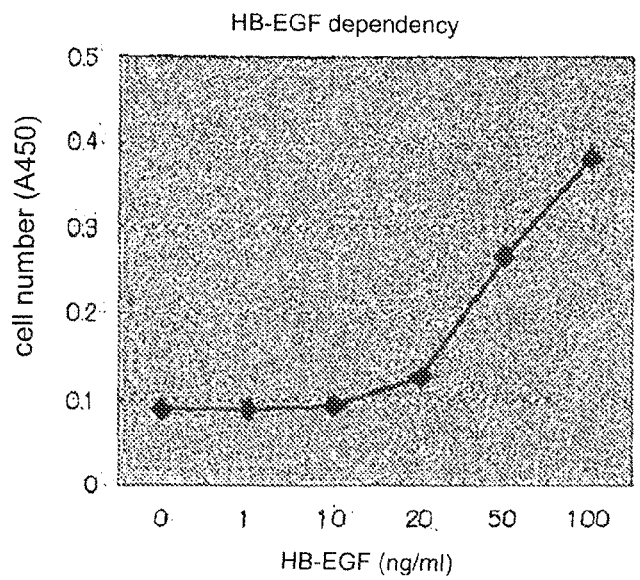
FIG. 2b is a graph that shows the dependence of EGFR_Ba/F3 cell proliferation on the HB-EGF concentration.

The results showed that growth of the established (EGFR_Ba/F3) cell line was promoted in a manner dependent on the HB-EGF concentration (FIG. 2b).

2-4. Hybridoma Screening 2-4-1. Screening for HB-EGF-Binding Antibodies (Primary Screening)

In order to obtain anti-HB-EGF neutralizing antibodies, HB-EGF-binding antibodies was first screened. ELISA and FACS were used to screen for binding antibodies.

2-4-1-1. ELISA

The hybridoma culture supernatant was reacted by incubation for 1 hour in ELISA plates (NUNC) coated with 1 µg/mL HB-EGF protein (R&D Systems, Inc., 259-HE). This was followed by reaction for 1 hour with alkali phosphatase (AP)-labeled anti-mouse IgG (Zymed Laboratories, Inc., #62-6622), after which color development was brought about by the addition of 1 mg/mL substrate (Sigma, S0942-50TAB). The $OD_{405}$ was measured with a plate reader (Bio-Rad Laboratories, Inc.) and the ELISA-positive wells were selected.

2-4-1-2. FACS

The hybridoma culture supernatant was added to HB-EGF_Ba/F3 cells (approximately $1\times10^5$ cells) and incubated for 1 hour at 4° C. FITC-labeled anti-mouse IgG antibody (Beckman Coulter, PN IM0819) was then added and incubated for 30 minutes at 4° C. The binding activity to cell surface HB-EGF was then analyzed for each hybridoma culture supernatant by FACS (Becton, Dickinson and Company).

2-4-1-3. Limit Dilution

Limit dilution (LD) was carried out in order to divide the clones exhibiting HB-EGF binding activity according to ELISA or FACS analysis into monoclones. The cell count in positive wells was measured, and seeding to 96-well plates was done so as to provide 3 cells/well. After incubation for approximately 10 days, the binding activity was again analyzed by ELISA or FACS on the culture supernatant in wells in which colonies had emerged. Using this series of procedures, five monoclones exhibiting HB-EGF binding activity were obtained in the HA series, four monoclones exhibiting HB-EGF binding activity were obtained in the HB series, and five monoclones exhibiting HB-EGF binding activity were obtained in the HC series.

2-4-1-4. Subtype Determination

The antibody subtype was determined using IsoStrips (Roche #1,493,027). The hybridoma culture supernatant diluted 10 times with PBS (−) was used for subtype determination.

TABLE 1

Characteristics of the isolated antibodies

| mouse strain | clone ID | EXP. 1 | | EXP. 2 | | iso-type |
| | | ELISA (OD405) | FACS (GEO-mean) | ELISA (OD405) | FACS (GEO-mean) | |
|---|---|---|---|---|---|---|
| | no-mAb | | 19.1 | | 6.9 | |
| bab #1 | HA-1 | 0.40 | 17.1 | | | 2b |
| | HA-3 | 0.42 | 59.0 | | | 2a |
| | HA-9 | 4.00 | 18.1 | | 10.2 | 2b |
| | HA-10 | 2.68 | 17.7 | | | G1 |
| | HA-20 | 4.00 | 18.9 | | | G1 |
| bab #2 | HB-10 | 2.55 | 108.0 | | | 2a |
| | HB-13 | 1.42 | 21.2 | | | G1 |
| | HB-20 | 3.91 | 188.2 | 4.00 | 98.9 | 2a |
| | HB-22 | 1.34 | 450.4 | | | 2b |
| MRL #1 | HC-15 | | 594.1 | 4.00 | 233.8 | 2a |
| | HC-19 | | 65.1 | 0.06 | 41.7 | 2a |
| | HC-26 | | 149.2 | 0.05 | 60.6 | 2a |
| | HC-42 | | 47.5 | 0.05 | 40.5 | 2a |
| | HC-74 | | | 0.05 | 45.2 | 2a |

2-4-2. Antibody Purification

The antibody was purified from 80 mL of the culture supernatant for the obtained monoclonal hybridoma using a HiTrap Protein G HP 1 mL column (Amersham Biosciences #17-0404-01). The hybridoma supernatant was adsorbed at a flow rate of 1 mL/min followed by washing with 20 mL 20 mM phosphate buffer (pH 7.0) and then elution with 3.5 mL 0.1 M glycine-HCl (pH 2.7). The eluate was recovered in 0.5 mL fractions in Eppendorf tubes, each of which already contained 50 µL 1 M Tris-HCL (pH 9.0). The $OD_{280nm}$ was measured. The fractions containing antibody were combined and PBS (−) was added to bring to a total of 2.5 mL, then the buffer was replaced to PBS(−) using a PD-10 column (Amersham Biosciences #17-0851-01). The purified antibody was passed through a 0.22 µm filter (Millipore #SLGV033RS) and the properties of the individual purified antibodies were investigated in detail as follows.

2-4-3. Analysis of the Growth Neutralizing Activity in EGFR_Ba/F3 Cells (Secondary Screening)

The neutralizing activity on the HB-EGF-dependent growth of EGFR_Ba/F3 cells was analyzed for each of the purified antibodies. EGFR_Ba/F3 cells were seeded to 96-well plates at $2\times10^4$ cells/well in the presence of HB-EGF (80 ng/mL) and the particular purified antibody was added at 0 to 200 ng/mL. After incubation for 3 days, the cell count was measured using WST-8 (Cell Counting Kit-8).

Figure 3A:
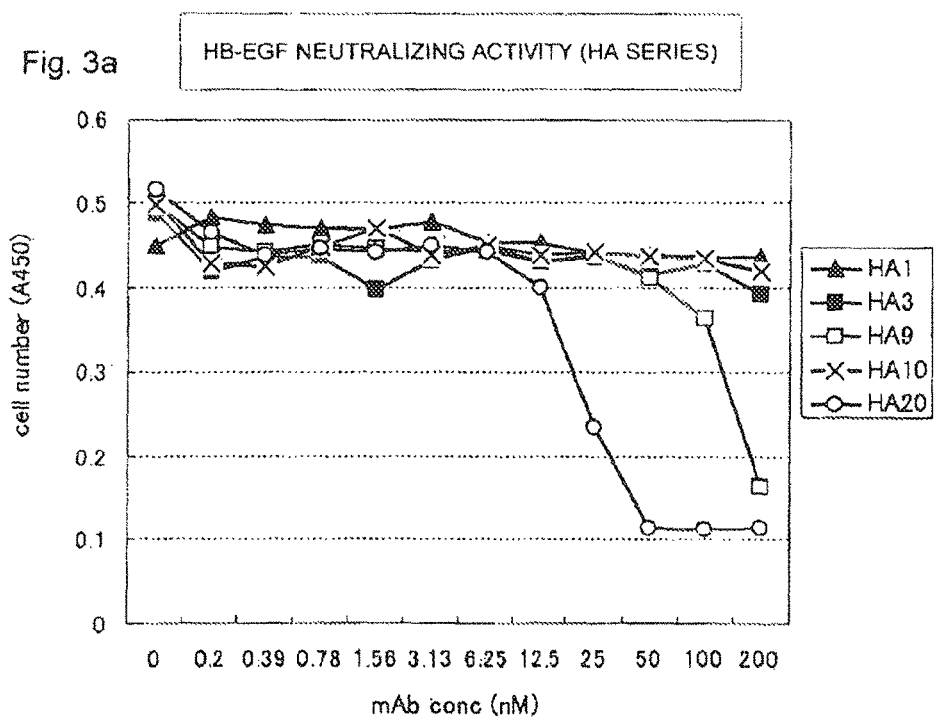
FIG. 3a is a graph that shows the neutralizing activity of HB-EGF antibodies (HA-1, HA-3, HA-9, HA-10, and HA-20) on the HB-EGF-dependent growth of EGFR_Ba/F3 cells.
Figure 3B:
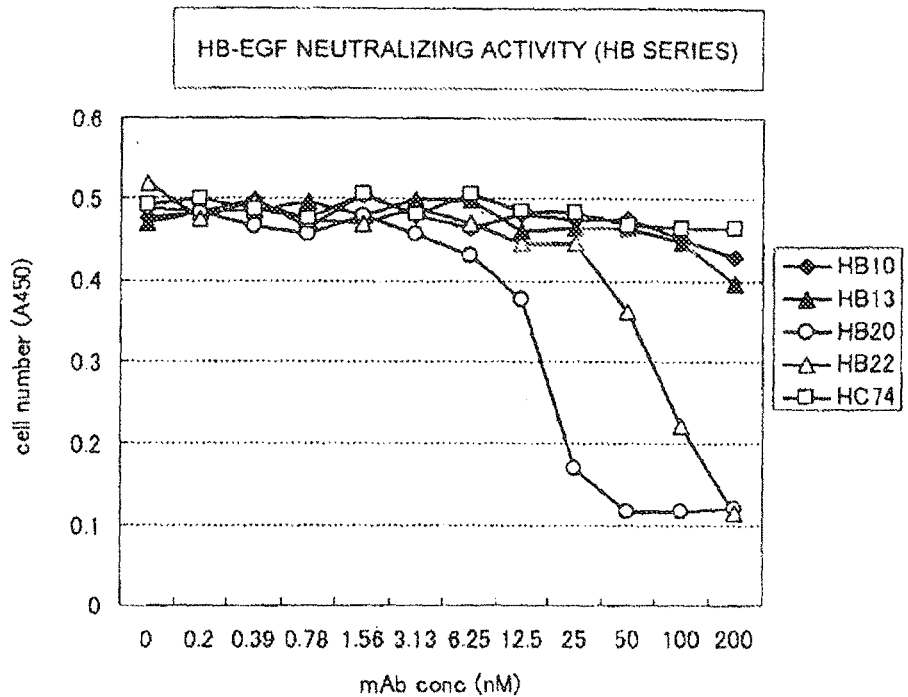
FIG. 3b is a graph that shows the neutralizing activity of HB-EGF antibodies (HB-10, HB-13, HB-20, HB-22, and HC-74) on the HB-EGF-dependent growth of EGFR_Ba/F3 cells.
Figure 3C:
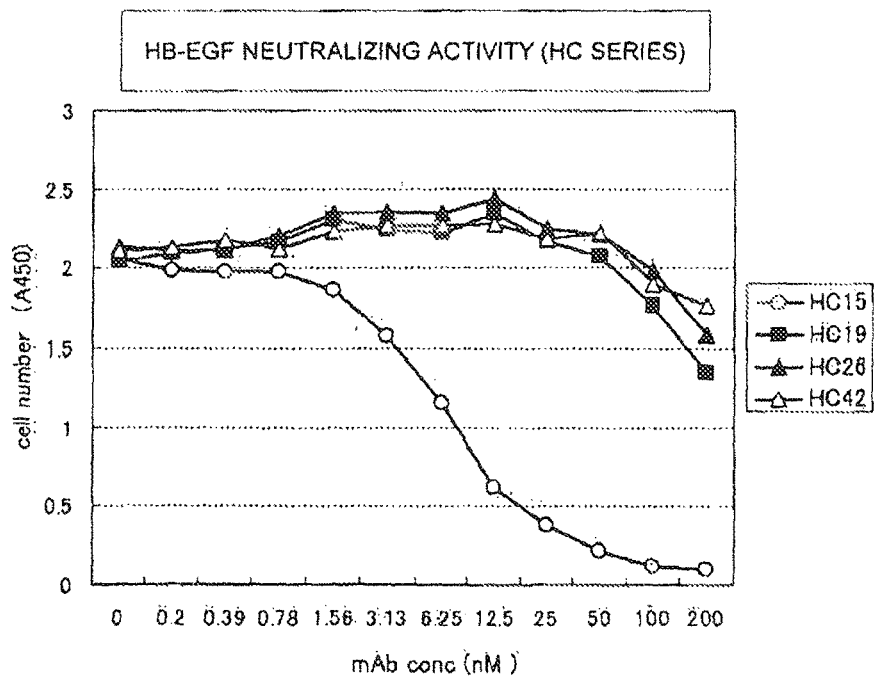
FIG. 3c is a graph that shows the neutralizing activity of HB-EGF antibodies (HC-15, HC-19, HC-26, and HC-42) on the HB-EGF-dependent growth of EGFR_Ba/F3 cells.

The results showed that HA-20 in the HA series, HB-20 in the HB series, and HC-15 in the HC series exhibit a strong neutralizing activity (FIGS. 3a to 3c).

Analysis of the Properties of HB-EGF Neutralizing Antibodies (HA-20, HB-20, HC-15)

3-1. Cloning of the Variable Region and Determination of the Amino Acid Sequence for HA-20, HB-20, and HC-15

The total RNA was purified using Trizol (#15596-018, Life Technologies) from approximately $5\times10^6$ hybridomas. Using a SMART RACE cDNA Amplification Kit (Clontech Laboratories, Inc., #PT3269-1), full-length cDNA synthesis was carried out according to the manual provided with the kit from 1 μg of the obtained total RNA. For each antibody, the gene encoding the variable region of the heavy chain (VH) and the variable region of the light chain (VL) was amplified using the obtained cDNA as template and an Advantage 2 PCR Enzyme System (Clontech Laboratories, Inc. #PT3281-1).

Cloning primers for the light chain variable region

UPM-k(VL-k)

UPM: provided with the kit

```
                                            (SEQ ID NO: 87)
   VL-k: GCT CAC TGG ATG GTG GGA AGA TG
``` cloning primers for the heavy chain variable region

HA-20: UPM-VH-G1

HB-20, HC-15: UPM-VH-2a

UPM: provided with the kit

```
                                            (SEQ ID NO: 88)
   VH-G1: GGG CCA GTG GAT AGA CAG ATG (SEQ ID NO: 89)
   VH-2a: CAG GGG CCA GTG GAT AGA CCG ATG
```

94° C./5 s, 72° C./2 min, 5 cycles

94° C./5 s, 70° C./10 s, 72° C./2 min, 5 cycles

94° C./5 s, 68° C./10 s, 72° C./2 min, 27 cycles

The gene fragments amplified in the preceding procedures were TA-cloned into pCRII-TOPO (Invitrogen TOPO TA-cloning Kit, #45-0640) and the base sequence for each insert was identified. The identified variable region sequences are shown in FIG. 4.

3-2. Analysis of the Binding Activity for the Active Form of HB-EGF

Figure 5:
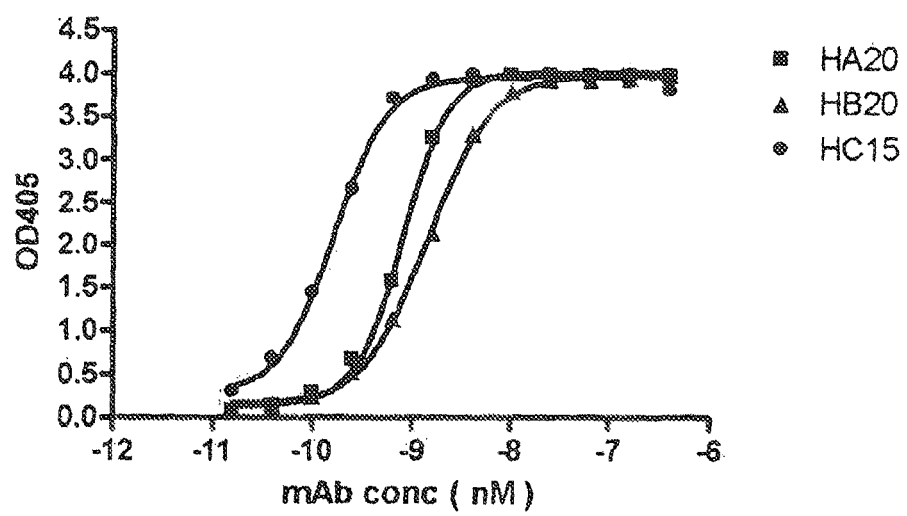
FIG. 5 is a graph that shows the binding activity of antibodies HA-20, HB-20, and HC-15 to active-form HB-EGF.

The following experiment was run in order to compare the ability of the thus obtained three antibodies (HA-20, HB-20, HC-15) to bind to active-form HB-EGF protein. The HA-20, HB-20, or HC-15 antibody was reacted at various concentrations in ELISA plates (NUNC) coated with 1 μg/mL HB-EGF protein (R&D Systems, Inc., 259-HE). This was followed by reaction for 1 hour with alkali phosphatase (AP)-labeled anti-mouse IgG (Zymed Laboratories, Inc., #62-6622), and addition of 1 mg/mL substrate (Sigma, S0942-50TAB) for color development. The $OD_{405}$ was measured with a plate reader and the antibody concentration that gave 50% binding ($ED_{50}$) was calculated based on the binding curve obtained for the particular antibody. With regard to the binding activity for active-form HB-EGF, $ED_{50}$ values of 0.2 to 1.4 nM were observed and a strong binding activity was thus found to be present in all instances (FIG. 5).

TABLE 2

| $ED_{50}$ value for binding to HB-EGF for the antibodies HA-20, HB-20, and HC-15 | |
|---|---|
| mAb | HB-EGF binding ($ED_{50}$, nmol/L) |
| HA-20 | 0.8 |
| HB-20 | 1.4 |
| HC-15 | 0.2 |

3-3. Analysis of the Binding Activity for proHB-EGF

The binding activity for proHB-EGF was then analyzed for the obtained three antibodies. RMG1 cells (ovarian cancer cell line, purchased from the Japan Health Sciences Foundation), which are known to intrinsically express HB-EGF, were cultured on a growth medium (Ham's F12 medium, Invitrogen Corporation) containing 10% FCS. Each of the antibodies (10 μg/mL) was reacted for 1 hour at 4° C. with the RMG1 cells, which intrinsically expressed HB-EGF, and the Ba/F3 cells (HB-EGF_Ba/F3), HB-EGF-expressing DG44 cells (HB-EGF_DG44), and SKOV-3 cells (HB-EGF_SKOV-3), which were cells overexpressing HB-EGF, followed by staining with FITC-labeled anti-mouse IgG antibody (Beckman Coulter, PN IM0819). Binding to the cell surface HB-EGF was then analyzed by FACS (Becton, Dickinson and Company) for each antibody.

Figure 6:
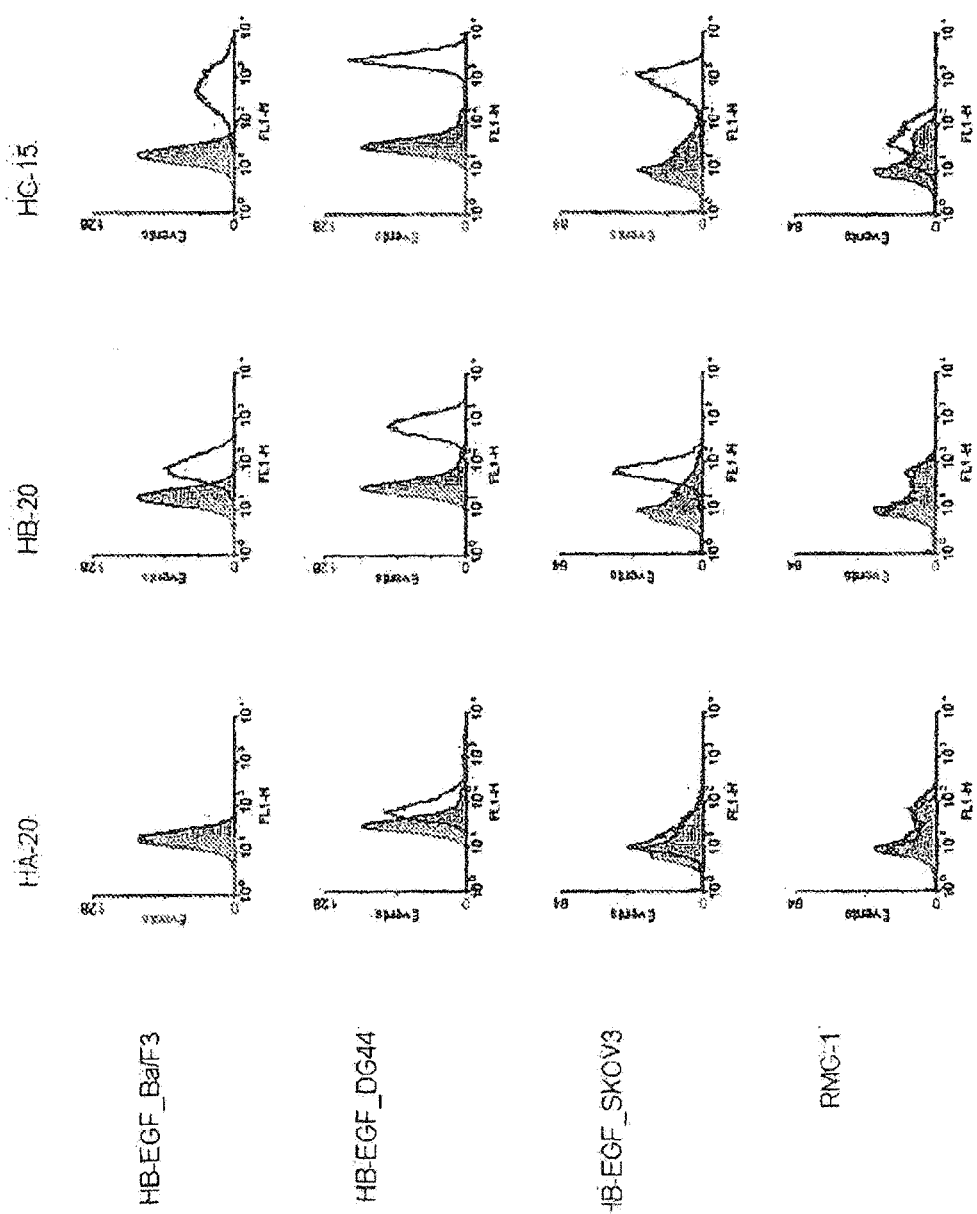
FIG. 6 shows histograms that show the binding activity of antibodies HA-20, HB-20, and HC-15 to proHB-EGF.

The histograms shown in FIG. 6 compare the binding activity of the HA-20, HB-20, and HC-15 antibodies according to FACS analysis to the proHB-EGF intrinsically expressed in RMG1 cells and the proHB-EGF overexpressed in the Ba/F3, DG44, and SKOV-3 cells. The grey waveform shows the staining pattern in the absence of the primary antibody (control), while the staining pattern in the presence of the particular antibody is shown with a solid line. The horizontal axis shows the staining intensity and the vertical axis shows the number of cells. As shown in FIG. 6, HB-20 and HC-15 recognized the HB-EGF overexpressed on the cell membrane and the HB-EGF intrinsically expressed on the cell membrane by the ovarian cancer line, while the HA-20 either did not bind at all or was bound only very weakly. These results showed that HA-20 was an antibody that, while strongly binding to active-form HB-EGF, did not recognize proHB-EGF.

Figure 7:
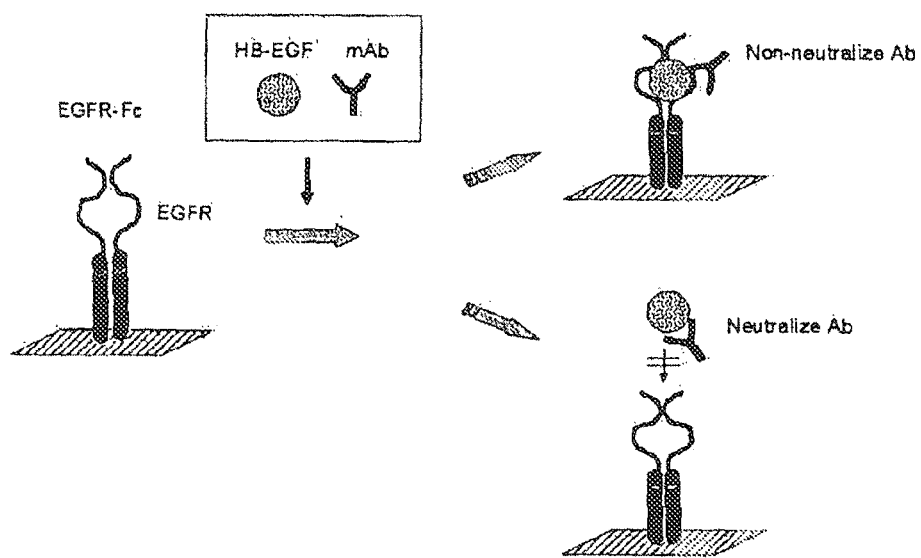
FIG. 7 is a schematic illustration showing the inhibition of binding between HB-EGF and EGFR by HB-EGF antibody on a solid phase.

3-4. Analysis of the Neutralizing Activity 3-4-1. Solid-Phase Analysis of the Ability to Inhibit EGFR/HB-EGF Binding 3-4-1-1. Production of EGFR-Fc Protein In order to construct an ELISA system that could check binding between HB-EGF and its receptor (EGFR) under solid phase conditions, a fusion protein (EGFR-Fc) from the extracellular region of EGFR and the Fc region of human IgG1 was first prepared to serve as the receptor protein. The mode of the inhibition of binding between HB-EGF and EGFR by HB-EGF antibody on the solid phase are schematically illustrated in FIG. 7.

An EGFR-Fc expression vector was first constructed. PCR was carried out using the following primers and using the pCV__hEGFR/mG-CSFR constructed in example 2-3-1 as the template.

```
                                            (SEQ ID NO: 90)
   EGFR-7: GTTAAGCTTCCACCATGCGACCCTCCGGGAC (SEQ ID NO: 91)
   EGFR-8: GTTGGTGACCGACGGGATCTTAGGCCCATTCGTTG
```

(94° C./30 s, 72° C./30 s: 25 cycles)

The amplified gene fragment coding for the extracellular region of EGFR was cleaved with BstEII and HindIII and was inserted between BstEII-HindIII in pMCDN2-Fc. The base sequence of the inserted gene fragment was confirmed to complete construction of a vector (pMCDN2_EGFR-Fc) expressing a fusion protein (EGFR-Fc) of the extracellular region of human EGFR and the Fc region of human IgG1. The base sequence and the amino acid sequence of the protein expressed by the expression vector, i.e., EGFR-Fc, are shown, respectively, in SEQ ID NO: 92 and SEQ ID NO: 93.

An EGFR-Fc protein-producing cell line was then established as follows. 15 µg of the EGFR-Fc expression vector (pMCDN2_EGFR-Fc) was first digested with pvuI and was then transfected by electroporation into DG44 cells. The EGFR-Fc protein produced in the culture supernatant of the G418-resistant strains was subsequently analyzed by Western blotting. Thus, 10 µL of the particular culture supernatant was separated by SDS-PAGE; blotted to a PVDF membrane; and the target protein was detected with HRP-labeled anti-human IgG antibody (Amersham, NA933V). The clone providing the highest production level was selected and run through expansion culture and the culture supernatant was recovered.

Purification of the EGFR-Fc protein was carried out as follows. The culture supernatant from the obtained EGFR-Fc-producing strain was adsorbed at a flow rate of 1 mL/min on a HiTrap Protein G HP 1 mL column (Amersham Biosciences #17-0404-01). After washing with 20 mL 20 mM phosphate buffer (pH 7.0), the protein was eluted with 3.5 mL 0.1 M glycine-HCl (pH 2.7). To identify the fraction containing the target protein 10 µL of each of the recovered fractions was separated by SDS-PAGE followed by Western blotting and staining with Coomassie Brilliant Blue (CBB). The buffer was replaced to PBS(-) using a PD-10 column (Amersham Biosciences #17-0851-01). The purified protein was passed through a 0.22 µm filter (Millipore #SLGV033RS) and was stored at 4° C.

3-4-1-2. Analysis of Binding Between HB-EGF and EGFR Using ELISA

Figure 8:
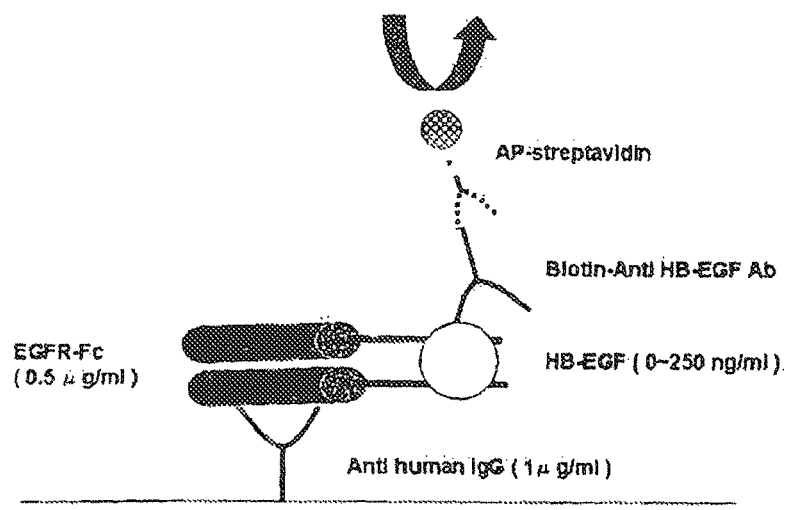
FIG. 8 is a schematic illustration showing an ELISA-based analysis model for the EGFR/HB-EGF binding mode.
Figure 9:
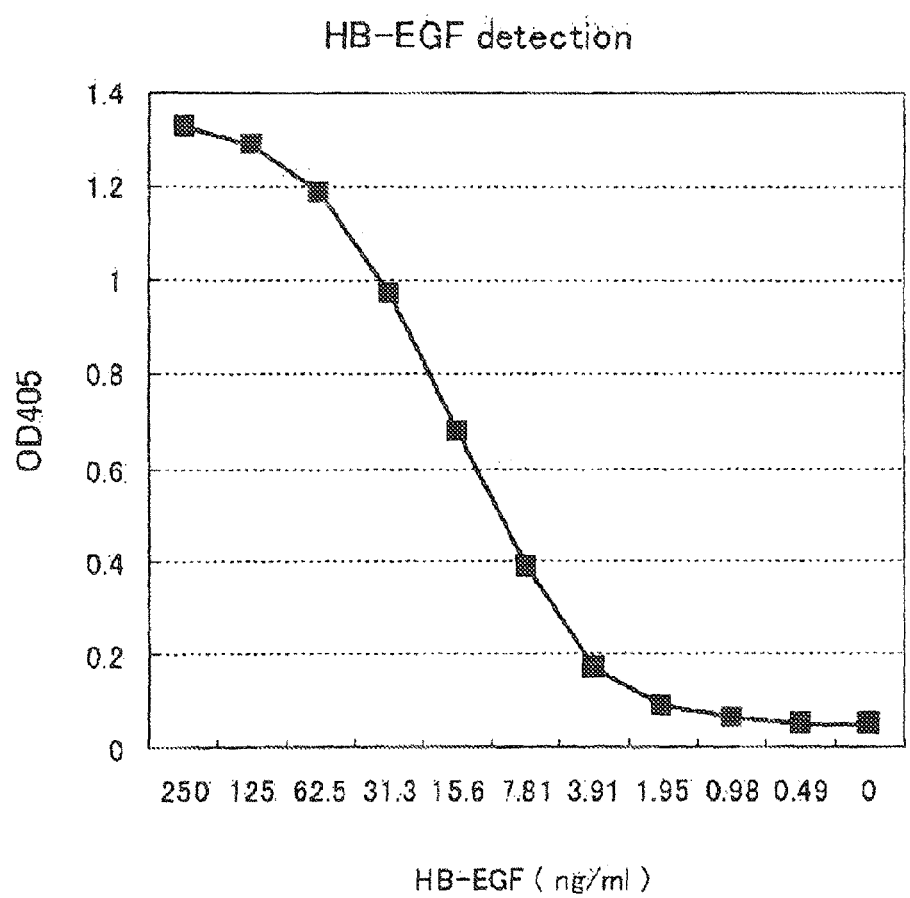
FIG. 9 is a graph that shows the concentration curve for HB-EGF detected in the ELISA-based analysis model for the EGFR/HB-EGF binding mode.

The purified EGFR-Fc was reacted at 0.5 µg/mL for 1 hour in ELISA plates coated with anti-human IgG antibody. 0 to 250 ng/mL HB-EGF (R&D Systems, Inc., 259-HE) was reacted for 1 hour, followed by detection of the HB-EGF protein bound to the EGFR-Fc with biotin-labeled anti-HB-EGF antibody (R&D Systems, Inc., BAF259) and AP-labeled streptavidin (Zymed, #43-8322). The model for analyzing the EGFR/HB-EGF binding mode using ELISA is shown in FIG. 8. The results showed that HB-EGF binding to EGFR could be detected with the solid-phase system beginning at a concentration of about 4 ng/mL (FIG. 9).

Figure 10:
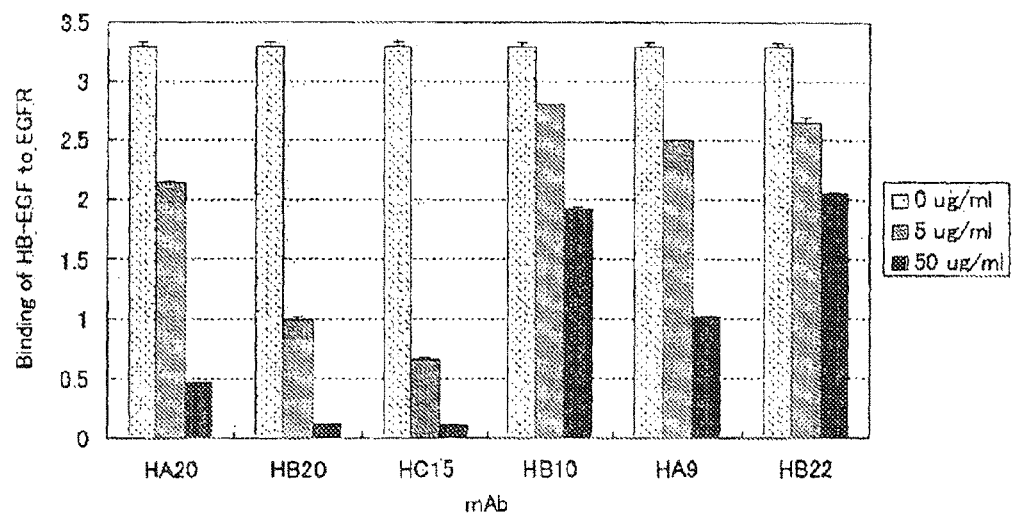
FIG. 10 is a graph that shows the inhibition of binding of HB-EGF to EGFR by antibodies HA-20, HB-20, and HC-15.

3-4-1-3. Analysis of the Antibody-Mediated Inhibitory Activity on HB-EGF/EGFR Binding The solid-phase system described in the preceding was used to analyze the inhibitory activity on HB-EGF/EGFR binding by the antibodies obtained in 2-4-2. The individual antibody and HB-EGF (50 ng/mL) were added to ELISA plates on which EGFR-Fc had been immobilized and a reacted for one hour at room temperature. The plates were washed with TBS-T and the HB-EGF bound to the EGFR was detected by the previously described procedure (FIG. 10).

A concentration-dependent ability to inhibit binding was observed for all the antibodies, and a particularly strong binding inhibition was recognized for HA-20, HB-20, and HC-15.

3-4-2. Growth Inhibiting Activity on EGFR_Ba/F3 Cells

The neutralizing activity on the HB-EGF-dependent growth of EGFR_Ba/F3 cells was compared for HA-20, HB-20, and HC-15. As above, the EGFR_Ba/F3 cells were seeded to 96-well plates at $2\times10^4$ cells/well in the presence of HB-EGF (80 ng/mL) and the particular purified antibody was added. After cultivation for 3 days, the cell count was measured using WST-8 (Cell Counting Kit-8) and a growth curve was constructed. The antibody concentration at 50% of the maximum inhibitory effect ($EC_{50}$ value) was calculated based on the obtained results.

Figure 11:
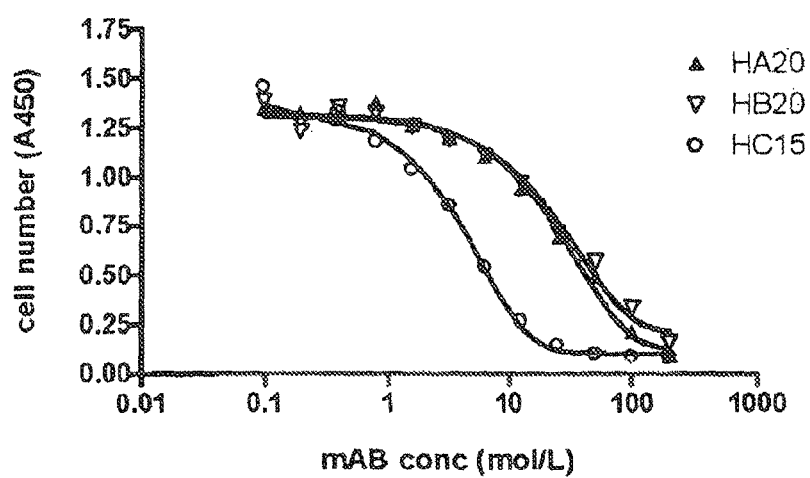
FIG. 11 is a graph that compares the inhibition of the growth of EGFR_Ba/F3 cells by antibodies HA-20, HB-20, and HC-15.

According to the results, the strongest growth inhibiting effect on EGFR_Ba/F3 cells was exhibited by HC-15 ($EC_{50}$=3.8 nM) followed by HA-20 ($EC_{50}$=32.6 nM) and HB-20 ($EC_{50}$=40.3 nM) (FIG. 11).

[Table 3]

$ED_{50}$ values exhibited by HA-20, HB-20, and HC-15 antibodies for the growth-inhibiting effect on EGFR_Ba/F3 cells

|  | HA-20 | HB-20 | HC-15 |
| --- | --- | --- | --- |
| EC50 (nM) | 32.6 | 40.3 | 3.8 |

3-4-3. Growth Inhibiting Activity for RMG-1 Cells

The neutralizing activity on RMG-1 cells was analyzed as follows. RMG-1 cells ($6\times10^3$ cells/well) were seeded into Ham's F12 medium containing 8% or 2% FCS in 96-well plates and the particular antibody was then added. After cultivation for one week, the cell count was measured using the WST-8 reagent.

Figure 12A:
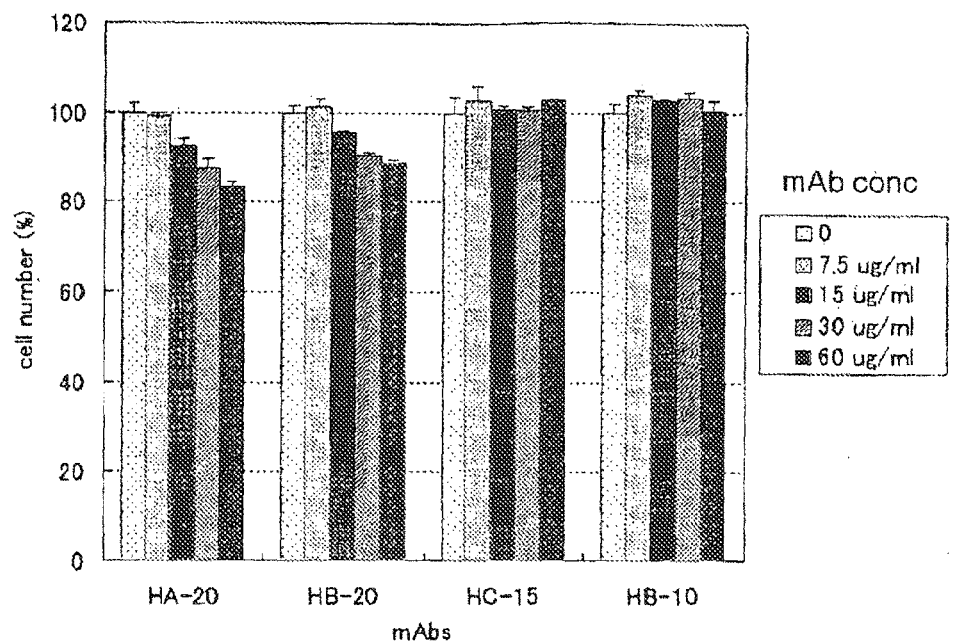
FIG. 12a is a graph that shows the inhibition of growth of the ovarian cancer cell line RMG-1 by the antibodies HA-20, HB-20, and HC-15 in a medium containing 8% FCS.
Figure 12B:
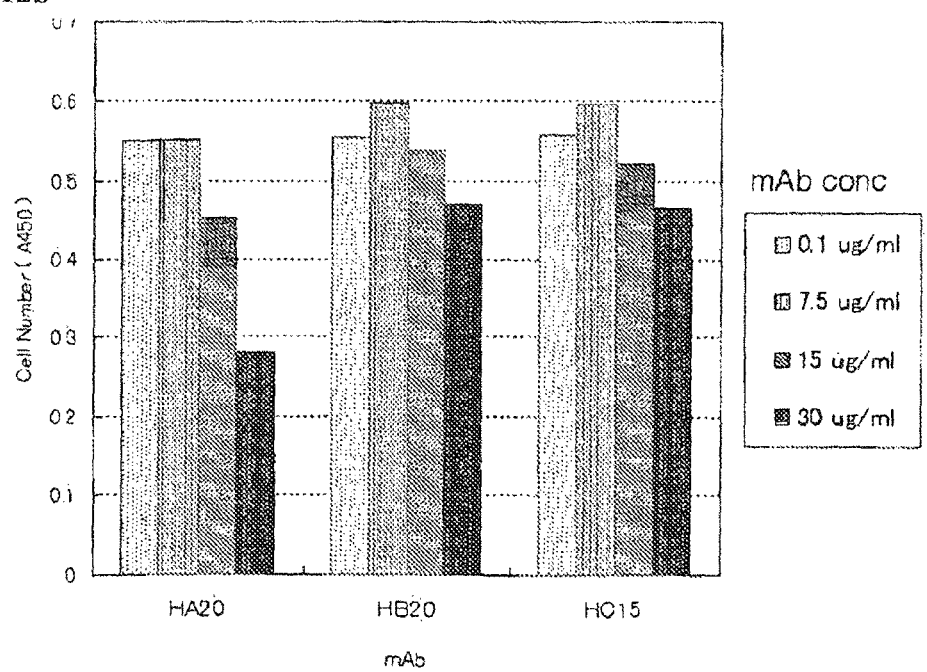
FIG. 12b is a graph that shows the inhibition of growth of the ovarian cancer cell line RMG-1 by the antibodies HA-20, HB-20, and HC-15 in a medium containing 2% FCS.

According to the results, HA-20 inhibited the growth of RMG-1 cells in an antibody concentration-dependent manner (FIG. 12). The growth inhibiting activity was particularly significant at a 2% FCS concentration.

What is claimed is:

1. An isolated monoclonal antibody that has a neutralizing activity on HB-EGF, which does not bind to the HB-EGF protein on the cell surface of cells that express HB-EGF having SEQ ID NO:60 wherein the antibody binds to the secreted forth of HB-EGF, which comprises the heparin-binding domain and the EGF-like domain of the HB-EGF protein, and wherein the antibody binds to an epitope that is the same as the epitope of the antibody comprising a heavy chain variable region having the amino acid sequence of SEQ ID NO:2 as CDR1, the amino acid sequence of SEQ ID NO:4 as CDR2, and the amino acid sequence of SEQ ID NO:6 as CDR3 and comprising a light chain variable region having the amino acid sequence of SEQ ID NO:12 as CDR1, the amino acid sequence of SEQ ID NO:14 as CDR2, and the amino acid sequence of SEQ ID NO:16 as CDR3.

2. The monoclonal antibody according to claim 1, wherein the cell that expresses HB-EGF having SEQ ID NO:60 is selected from RMG-1, and Ba/F3, DG44, and SKOV-3 that recombinantly expresses HB-EGF having SEQ ID NO:60.

3. The monoclonal antibody according to claim 1, wherein the antibody is a low molecular weight antibody.

4. An anti-cancer agent comprising the monoclonal antibody according to claim 1 as an active ingredient.

5. The anti-cancer agent according to claim 4, wherein the cancer is pancreatic cancer, liver cancer, esophageal cancer, melanoma, colorectal cancer, gastric cancer, ovarian cancer, bladder cancer, or a brain tumor.

6. A cell proliferation inhibitor comprising the monoclonal antibody according to claim 1 as an active ingredient.

7. The cell proliferation inhibitor according to claim 6, wherein the cells are pancreatic cancer cells, liver cancer cells, esophageal cancer cells, melanoma cells, colorectal cancer cells, gastric cancer cells, ovarian cancer cells, bladder cancer cells, or brain tumor cells.

8. An isolated antibody selected from the following (a) to (h):
   (a) an antibody comprising a heavy chain variable region having the amino acid sequence of SEQ ID NO:2 as CDR1, the amino acid sequence of SEQ ID NO:4 as CDR2, and the amino acid sequence of SEQ ID NO:6 as CDR3 and comprising a light chain variable region having the amino acid sequence of SEQ ID NO:12 as CDR1, the amino acid sequence of SEQ ID NO:14 as CDR2, and the amino acid sequence of SEQ ID NO:16 as CDR3;
   (b) an antibody according to (a) that has the amino acid sequence of SEQ ID NO:8 as CH;
   (c) an antibody according to (a) that has the amino acid sequence of SEQ ID NO:10 as CH;
   (d) an antibody according to (a) that has the amino acid sequence of SEQ ID NO:18 as CL;
   (e) an antibody according to (a) that has the amino acid sequence of SEQ ID NO:20 as CL;
   (f) an antibody comprising the heavy chain according to (b) and the light chain according to (d);
   (g) an antibody comprising the heavy chain according to (c) and the light chain according to (e); and
   (h) an antibody that binds to an epitope that is the same as the epitope of HB-EGF protein that is bound by the antibody according to any of (a) to (g).

9. The monoclonal antibody according to claim 8, wherein the antibody is a low molecular weight antibody.

10. An anti-cancer agent comprising the monoclonal antibody according to claim 8 as an active ingredient.

11. The anti-cancer agent according to claim 10, wherein the cancer is pancreatic cancer, liver cancer, esophageal cancer, melanoma, colorectal cancer, gastric cancer, ovarian cancer, bladder cancer, or a brain tumor.

12. A cell proliferation inhibitor comprising the monoclonal antibody according to claim 8 as an active ingredient.

13. The cell proliferation inhibitor according to claim 12, wherein the cells are pancreatic cancer cells, liver cancer cells, esophageal cancer cells, melanoma cells, colorectal cancer cells, gastric cancer cells, ovarian cancer cells, bladder cancer cells, or brain tumor cells.

* * * * *